US008163523B2

(12) United States Patent
Bilsel et al.

(10) Patent No.: US 8,163,523 B2
(45) Date of Patent: Apr. 24, 2012

(54) CELL-BASED SYSTEMS FOR PRODUCING INFLUENZA VACCINES

(75) Inventors: Pamuk Bilsel, Madison, WI (US); Yoshihiro Kawaoka, Middleton, WI (US); Gabriele Neumann, Madison, WI (US)

(73) Assignee: Flugen, Inc., Madison, WI (US)

(*) Notice: Subject to any disclaimer, the term of this patent is extended or adjusted under 35 U.S.C. 154(b) by 58 days.

(21) Appl. No.: 12/481,402

(22) Filed: Jun. 9, 2009

(65) Prior Publication Data

US 2010/0021499 A1     Jan. 28, 2010

Related U.S. Application Data

(60) Provisional application No. 61/060,653, filed on Jun. 11, 2008, provisional application No. 61/169,548, filed on Apr. 15, 2009.

(51) Int. Cl.
     *C12P 19/34*      (2006.01)
(52) U.S. Cl. ..... 435/91.1; 435/358; 435/325; 424/209.1
(58) Field of Classification Search ........................ None
See application file for complete search history.

(56) References Cited

U.S. PATENT DOCUMENTS

| | | | |
|---|---|---|---|
| 7,176,021 B2 | 2/2007 | Kawaoka | |
| 7,504,248 B2 * | 3/2009 | Marzio et al. | 435/235.1 |
| 2008/0254065 A1 * | 10/2008 | Podda et al. | 424/206.1 |

FOREIGN PATENT DOCUMENTS

| | | |
|---|---|---|
| EP | 1 103 610 A | 5/2001 |
| WO | WO 2007/110776 A | 10/2007 |

OTHER PUBLICATIONS

Kumlin et al., Sialic acid tissue distribution and influenza virus tropism, 2008, Influenza and Other Respiratory Viruses, vol. 2, No. 5, pp. 147-154.*
Nicholls et al., Sialic acid receptor detection in the human respiratory tract: evidence for widespread distribution of potential binding sites for human and avian influenza viruses, 2007, Respiratory Research, vol. 8, No. 73, pp. 1-10.*
Khanna et al., Emerging infl uenza virus: A global threat, 2008, Journal of Biosciences, vol. 33, pp. 475-482.*
Narasaraju et al., Adaptation of human influenza H3N2 virus in a mouse pneumonitis model: insights into viral virulence, tissue tropism and host pathogenesis, 2009 (published Oct. 17, 2008 online), Microbes and Infection, vol. 11, pp. 2-11.*
Genzel et al., Metabolism of MDCK cells during cell growth and influenza virus production in large-scale microcarrier culture, 2004, Vaccine, vol. 22, pp. 2202-2208.*
Halperin et al., Safety and immunogenicity of a trivalent, inactivated, mammalian cell culture-derived influenza vaccine in healthy adults, seniors, and children, 2002, Vaccine, vol. 20, pp. 1240-1247.*
GenBank Accession # NM_032528, Homo sapiens ST6 beta-galactosamide alpha-2,6-sialyltranferase 2 (ST6GAL2), mRNA, 2008.*
GenBank Accession # BC040009.1, Homo sapiens ST6 beta-galactosamide alpha-2,6-sialyltranferase 1, mRNA (cDNA clone MGC:48859 Image:5557868), complete cds, 2006.*
"Avery's Drug Treatment Principles and Practice of Clinical Pharmacology and Therapeutics", Third Edition, (1987), pp. 1-4, ADIS Press, Ltd., Williams and Wikins, Third Ed., Baltimore, MD.
"Cell Communication and Signallng" (2009), 1 page, 7(Suppl. 1):A14, BioMed Central Ltd.
Berkow et al., "The Merck Manual of Diagnosis and Therapy—Viral Diseases", *The Merck Manual*, 15 Edition, (1987), pp. 173-174,Ch. 12, Merck & Co., Rahway, N.J.
Ehrhardt et al., "Bivalent role of the phosphatidylinositol-3-kinase (PI3K) during influenza virus infection and host cell defence", *Cellular Microbiology*, Mar. 29, 2006, pp. 1336-1348, vol. 8, No. 8, Blackwell Publishing Ltd.
Fukuta et al., "Genetic engineering of CHO cells producing human interferon-γ by transfection of sialytransferases" *Glycoconjugate Journal*, (2000), pp. 895-904, vol. Kluwer Academic Publishers, The Netherlands.
Goodman et al., eds. "Goodman and Gilman's The Pharmacological Basis of Therapeutics", $8^{th}$ Edition, *Antiviral Agents*, (1990), p. 1196, Ch. 51, Pergamon Press, Inc., Elmsford, N.Y.
Govorkova et al., "African Green Monkey Kidney (Vero) Cells Provide an Alternative Host Cell System for Influenza A and B Viruses", *Journal of Virology*, Aug. 1996, pp. 5519-5524, vol. 70, No. 8, American Society for Microbiology, USA.
Hatakeyama et al., "Enhanced Expression of an α2,6-Linked Sialic Acid on MDCK Cells Improves Isolation of Human Influenza Viruses and Evaluation of Their Sensitivity to a Neuraminidase Inhibitor", *Journal of Clinical Microbiology*, Aug. 2005, pp. 4139-4146, vol. 43, No. 8, American Society for Microbiology, USA.
Jayapal et al., "Recombinant Protein Therapeutics from CHO Cells-20 Years and Counting", *Chemical Engineering Progress*, CHO Consortium, SBE Special Section, Oct. 2007, pp. 40-47, Society for Biological Engineering, An AlChE Technological Community.
Katzung ed. "Table 52-7 (cont'd.). Nonsurgical antimicrobial phophylaxis of documented benefit or in common use", and "Table II-1. Materials commonly used for active immunization", *Basic and Clinical Pharmacology*, Fifth Edition, (1992), pp. 710, 944-945, Appleton and Lange, Norwalk, CN.
Kilbourne, "Future Influenza Vaccines and the Use of Genetic Recombinants", *Bull. Wld Hlth Org.*, (1969), pp. 643-645, vol. 41, World Health Organization, Geneve.
Kistner et al., "A novel mammalian cell (Vero) derived influenza virus vaccine: Development, characterization and industrial scale production", *Wien Klin Wochenschr*, Mar. 1999, pp. 207-214, vol. 111, issue 5, Winer klinisch Wochenschrift, Austria.

(Continued)

*Primary Examiner* — Benjamin P Blumel
(74) *Attorney, Agent, or Firm* — Foley & Lardner LLP

(57) ABSTRACT

The present invention relates to a cell-based method for producing influenza virus vaccines by enriching the population of surface-bound α2,6-sialic acid receptors on a cell surface, such as on a Chinese Hamster Ovary (CHO) cell surface. The host cell therefore presents numerous binding sites to which an influenza virus can bind via its hemagglutinin spike protein and infect the host cell. In contrast to wild-type CHO cells, the surface of the mutated CHO cells of the present invention contains an enriched population of α2,6-sialic acid receptors which makes the inventive CHO cells highly susceptible to viral infection, and therefore safe, effective, and highly efficient cells for rapidly producing influenza vaccines.

16 Claims, 35 Drawing Sheets

OTHER PUBLICATIONS

Figure 1:
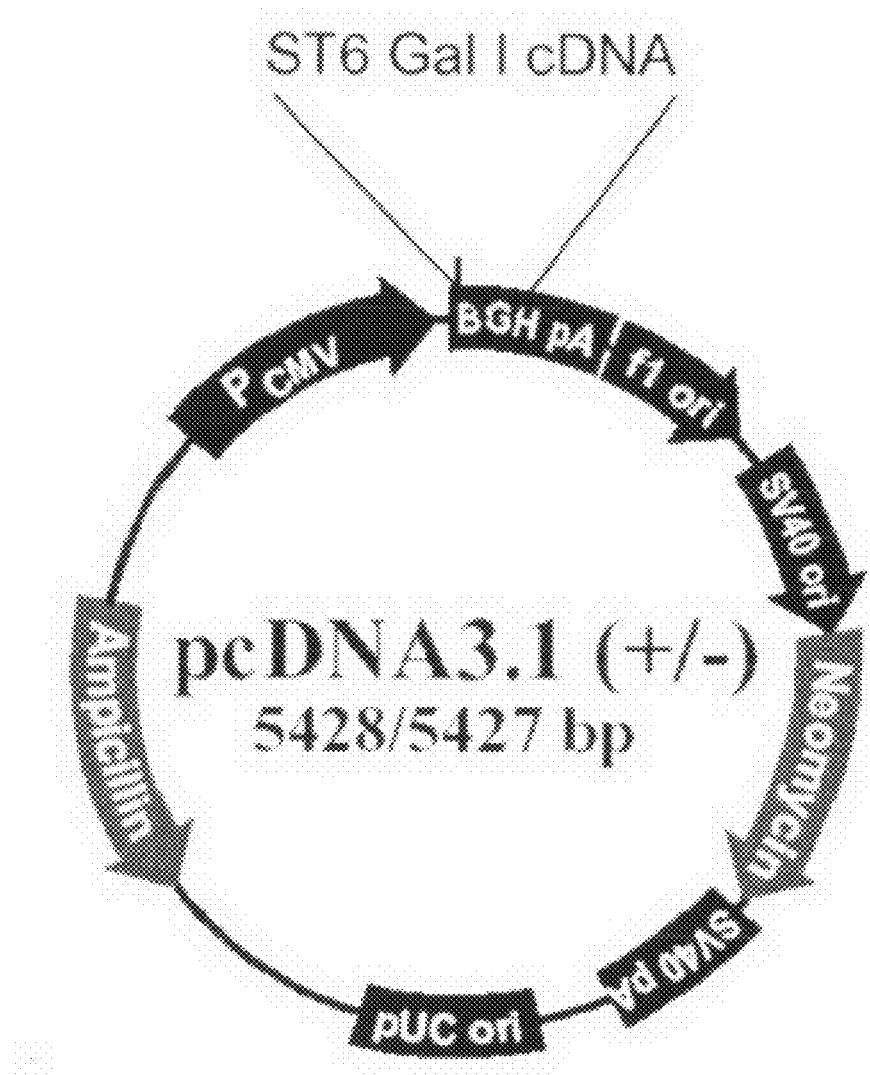
Figure 2:
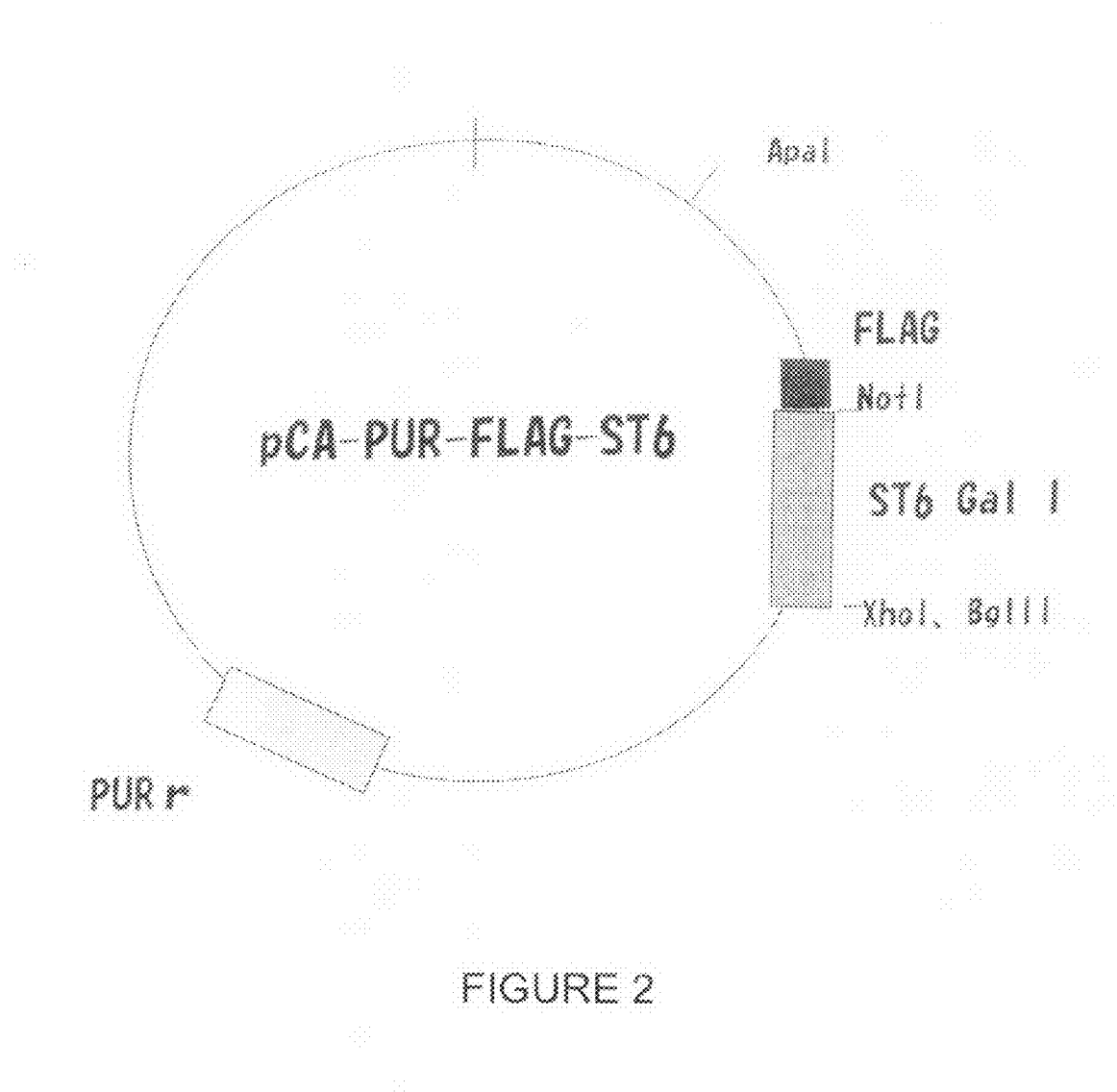
Figure 4A:
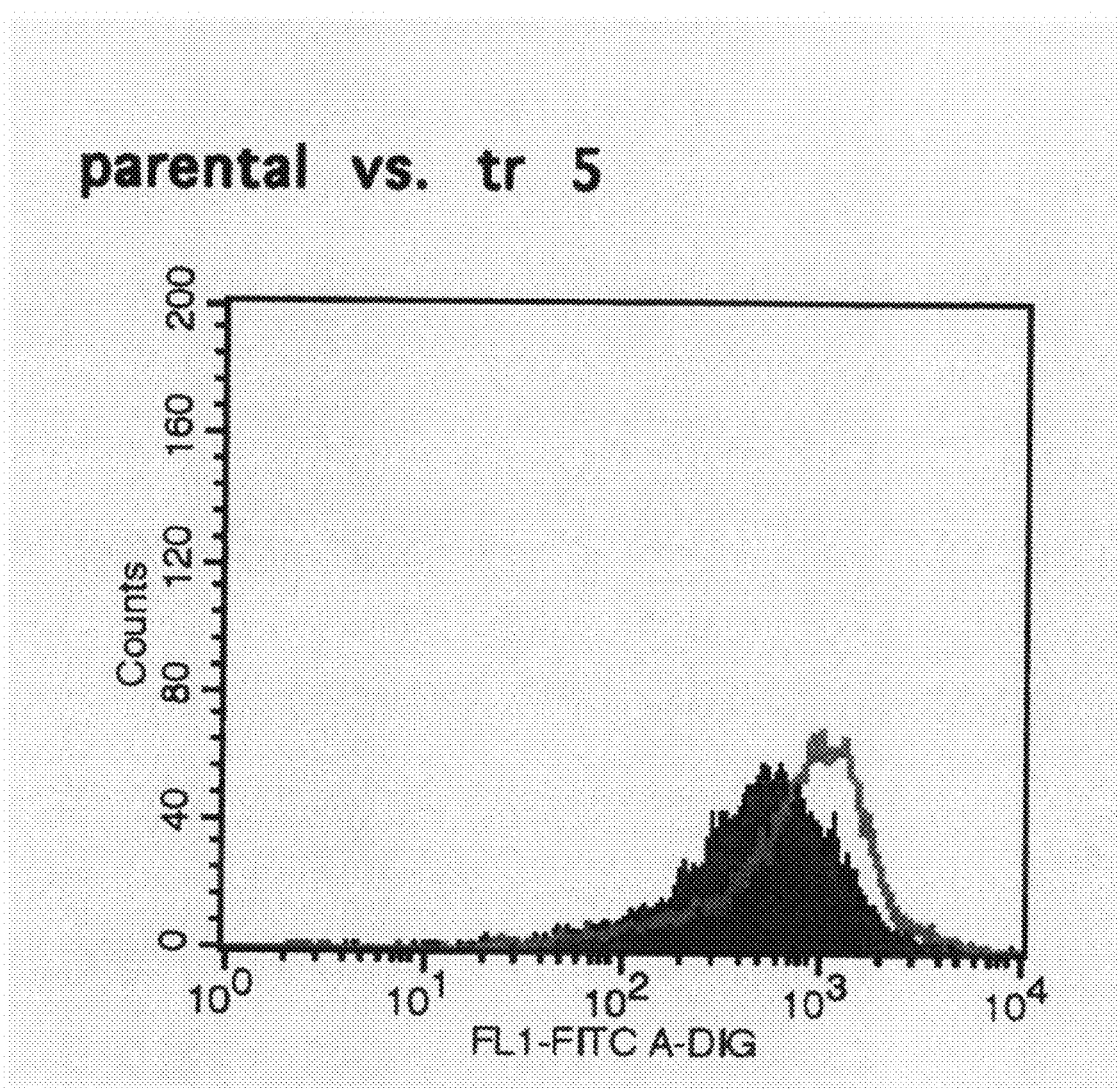
Figure 4B:
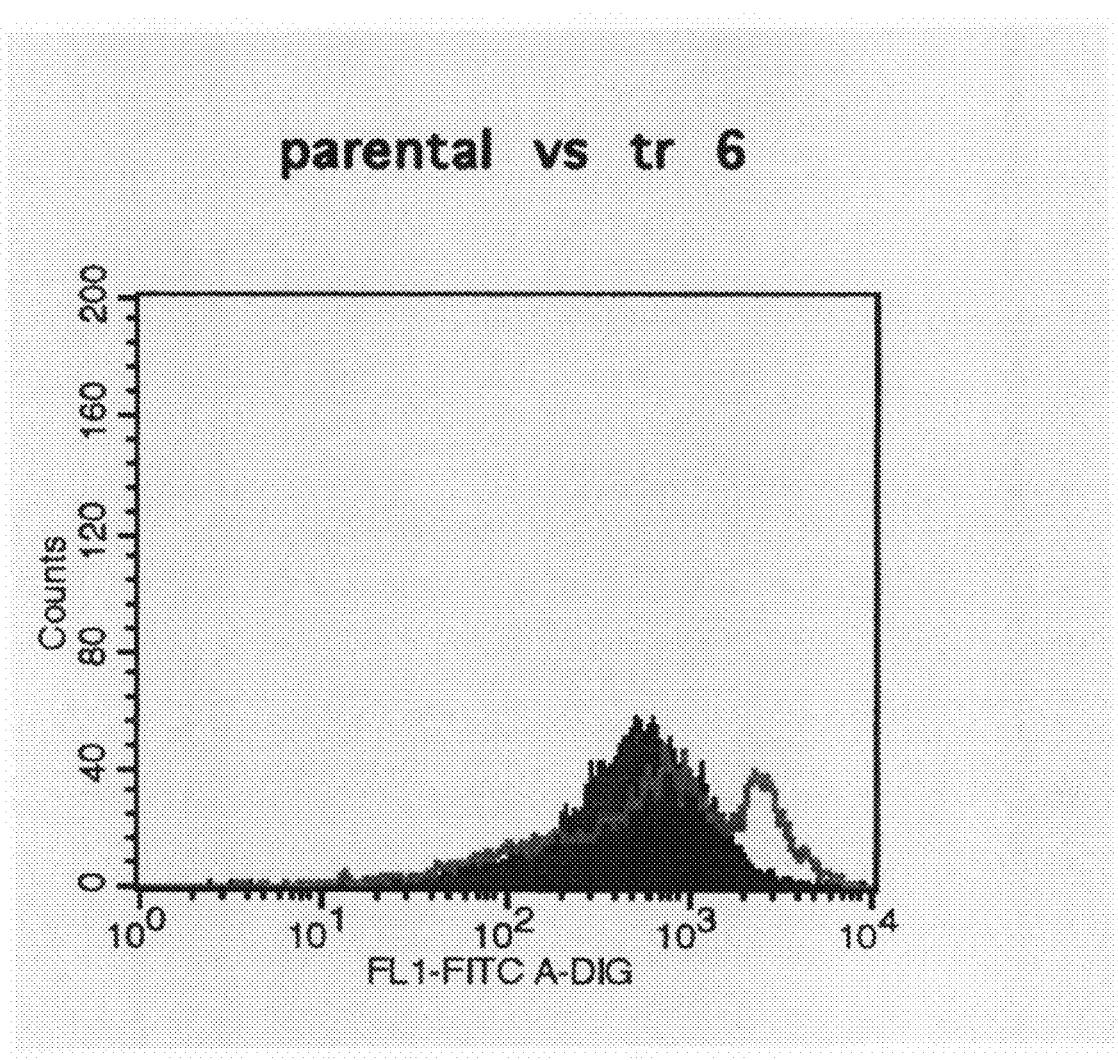
Figure 4C:
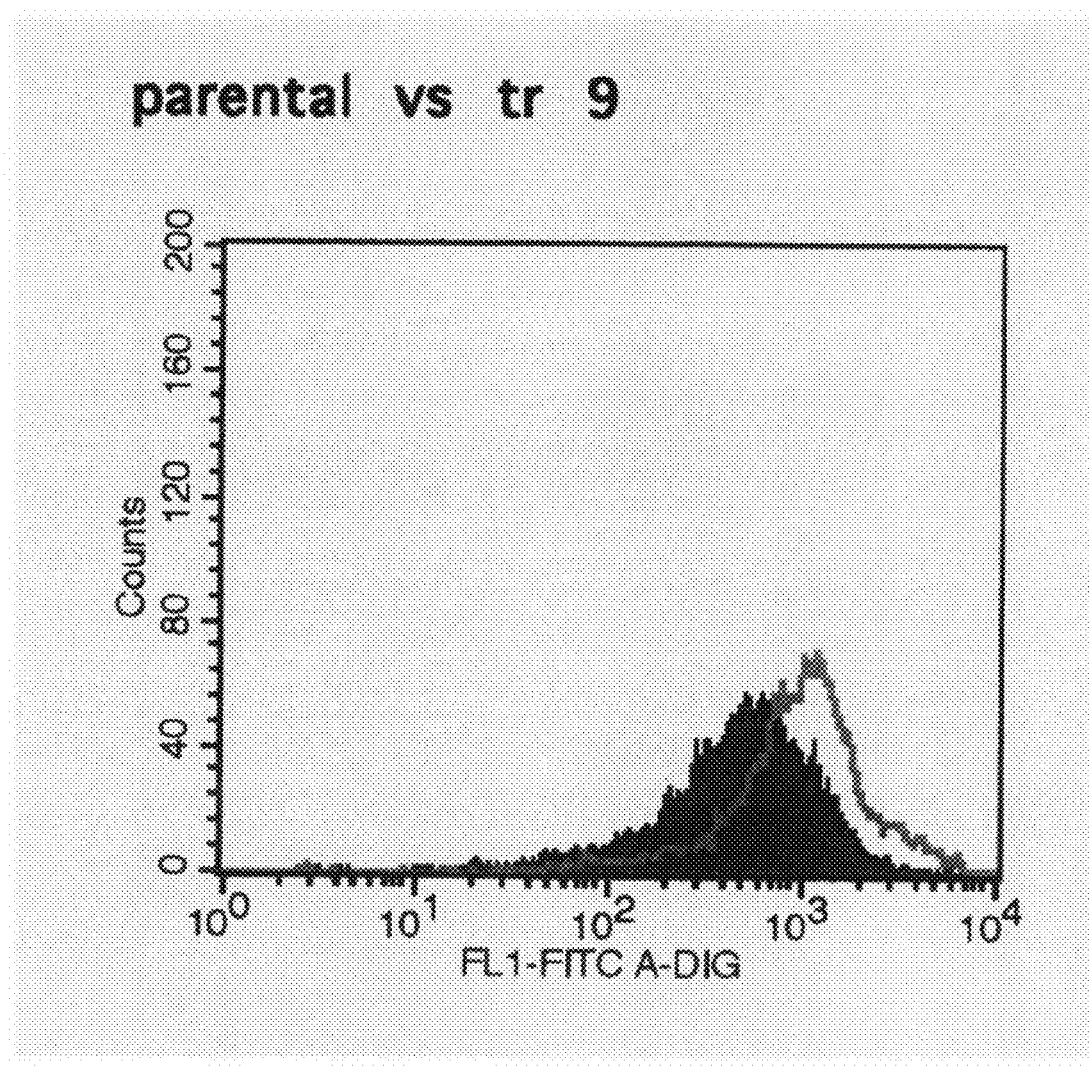
Figure 4D:
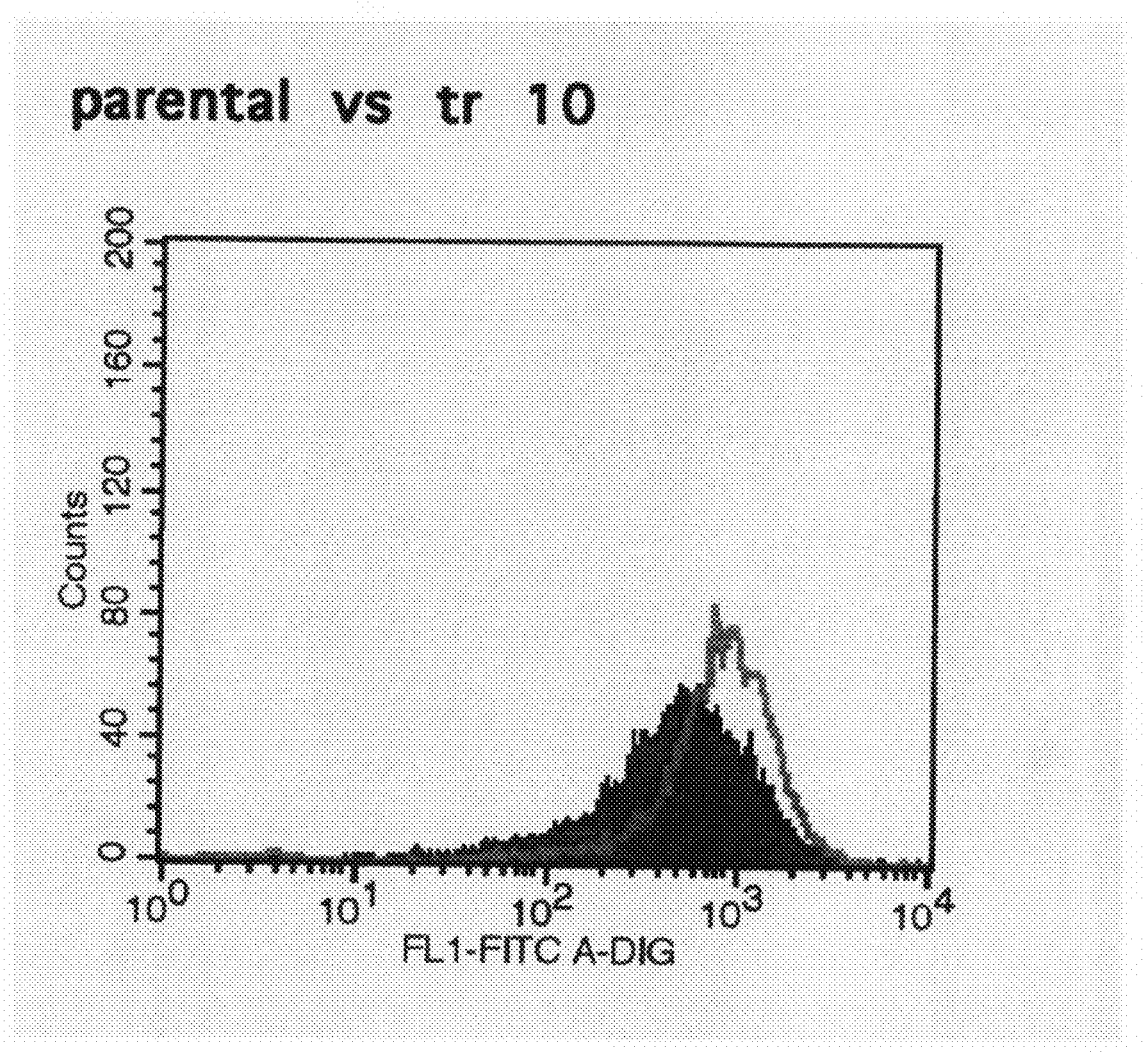
Figure 4E:
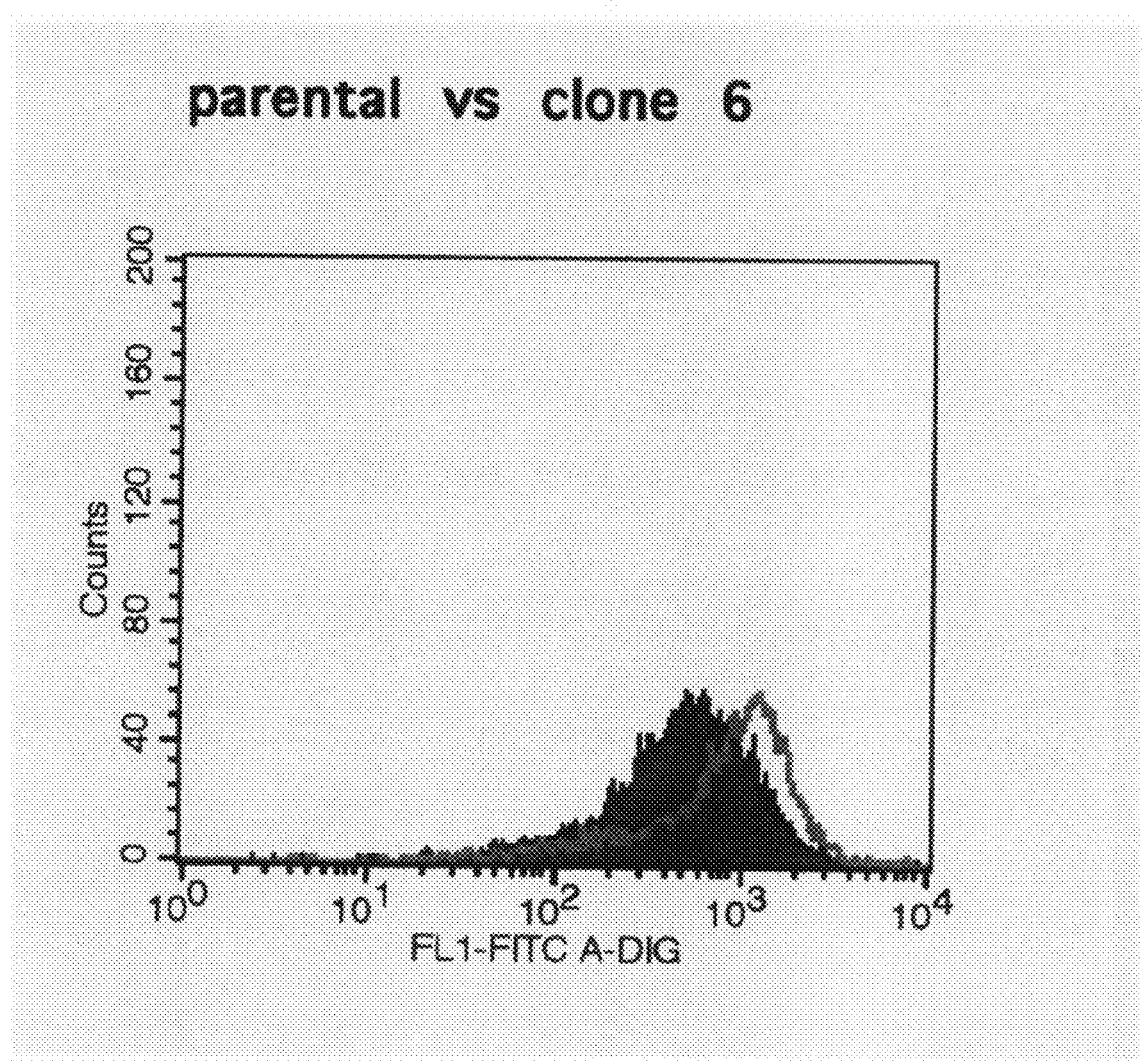
Figure 5A:
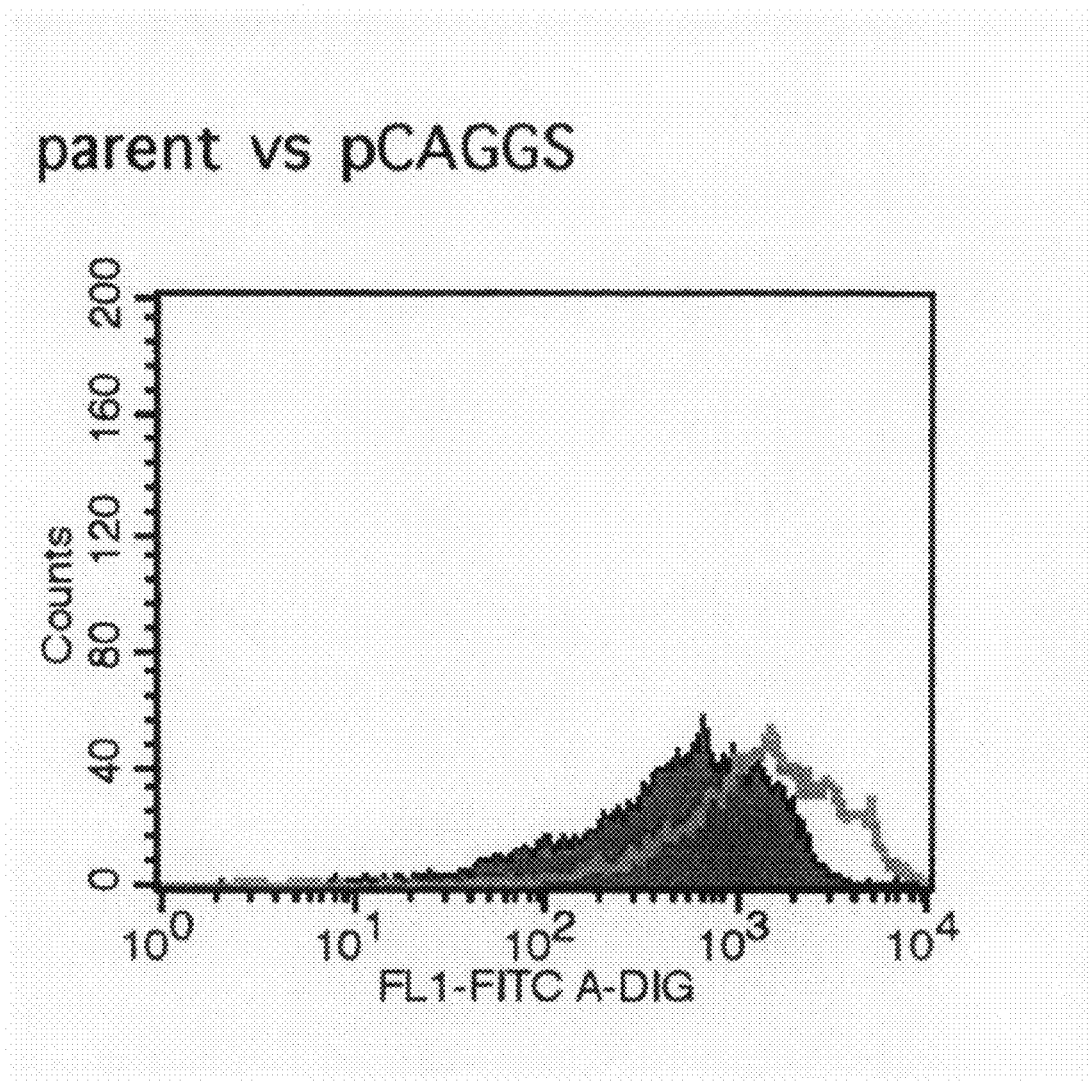
Figure 5B:
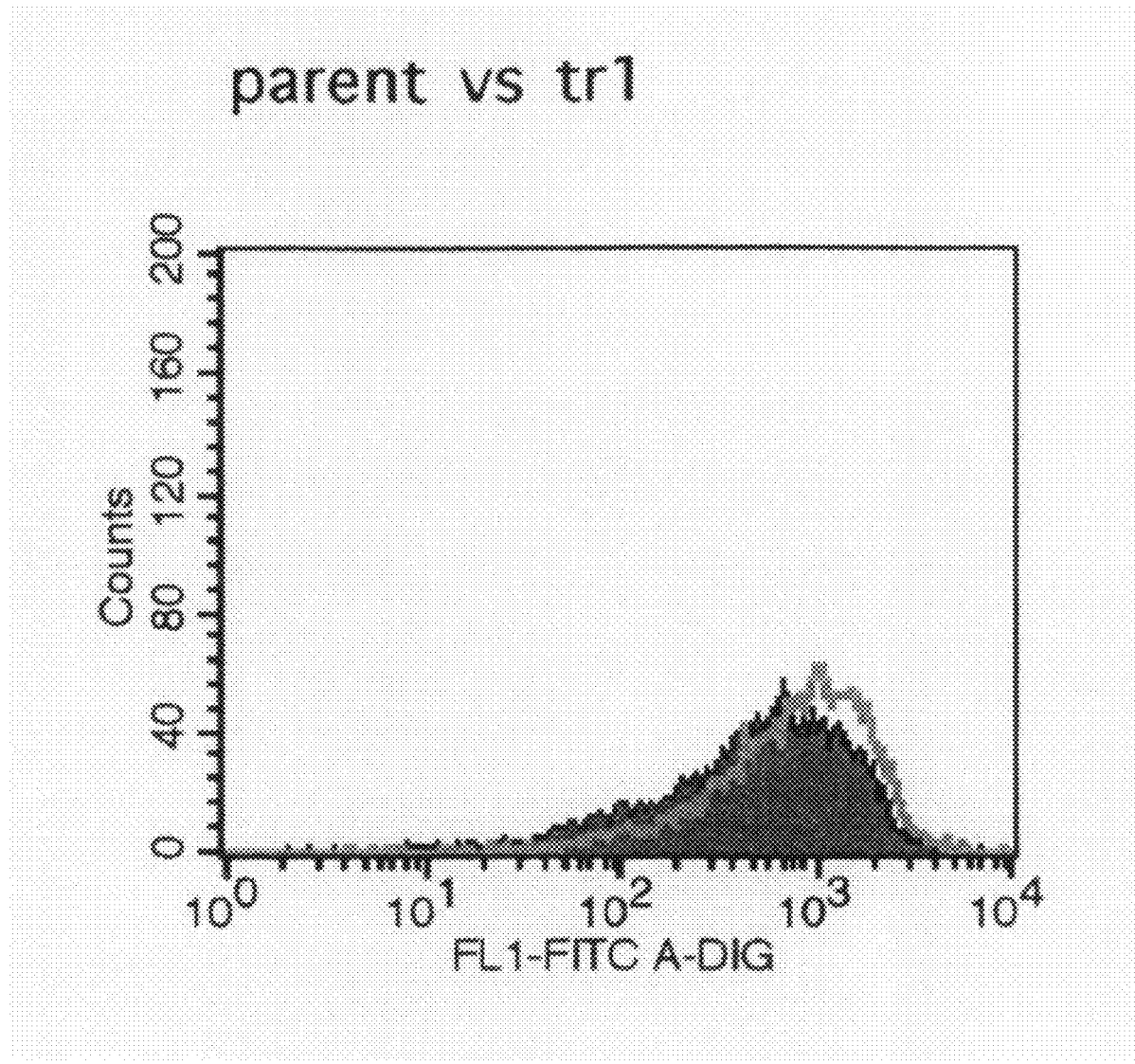
Figure 5C:
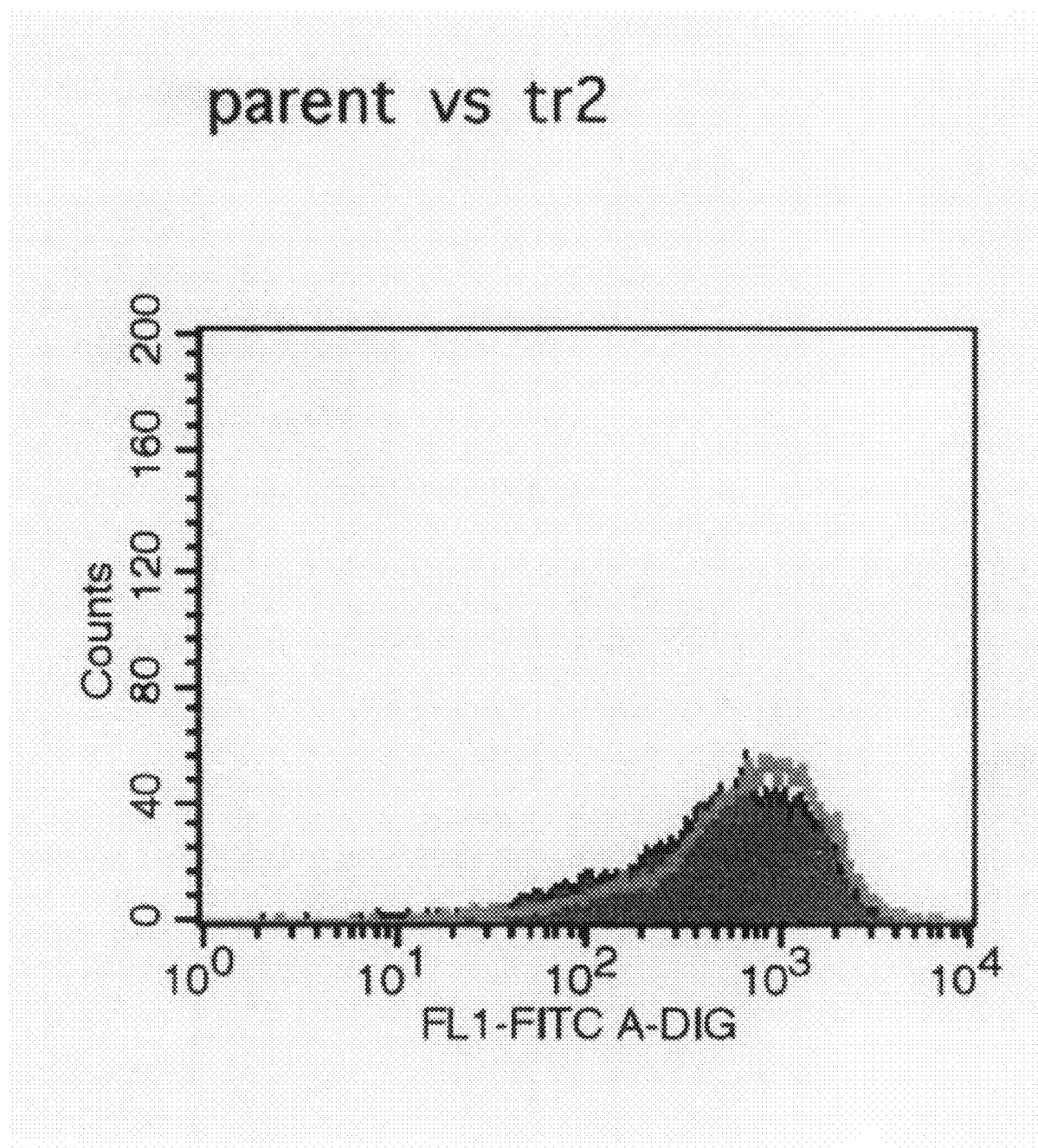
Figure 5D:
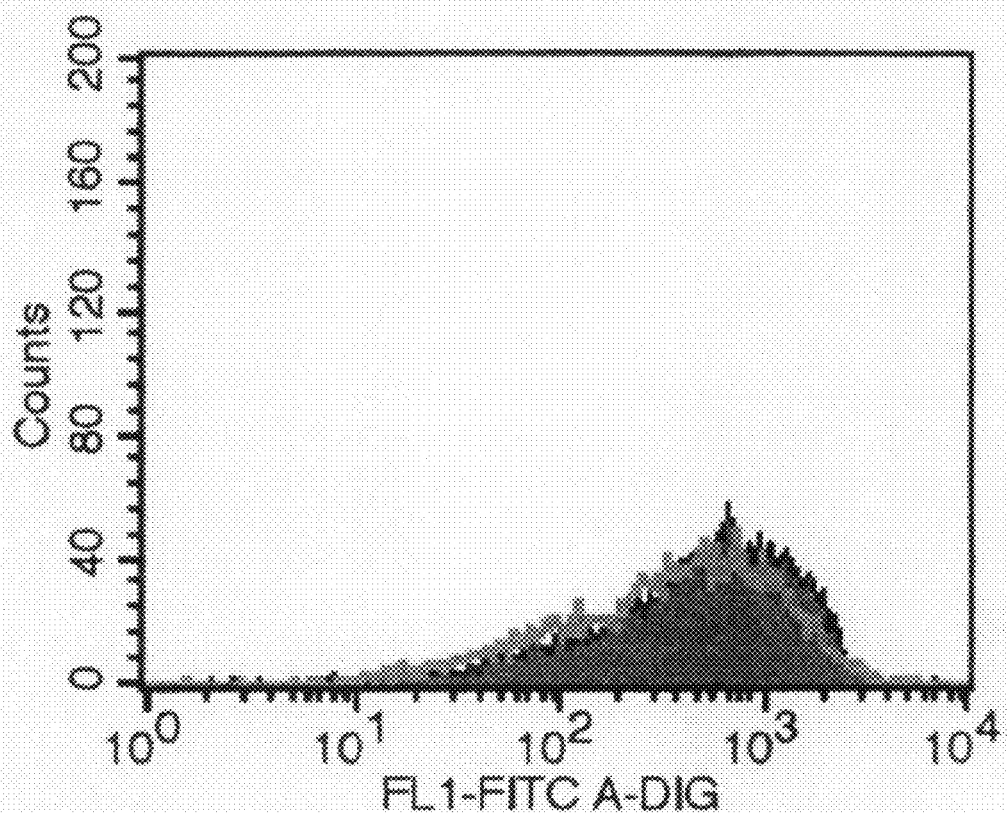
Figure 5E:
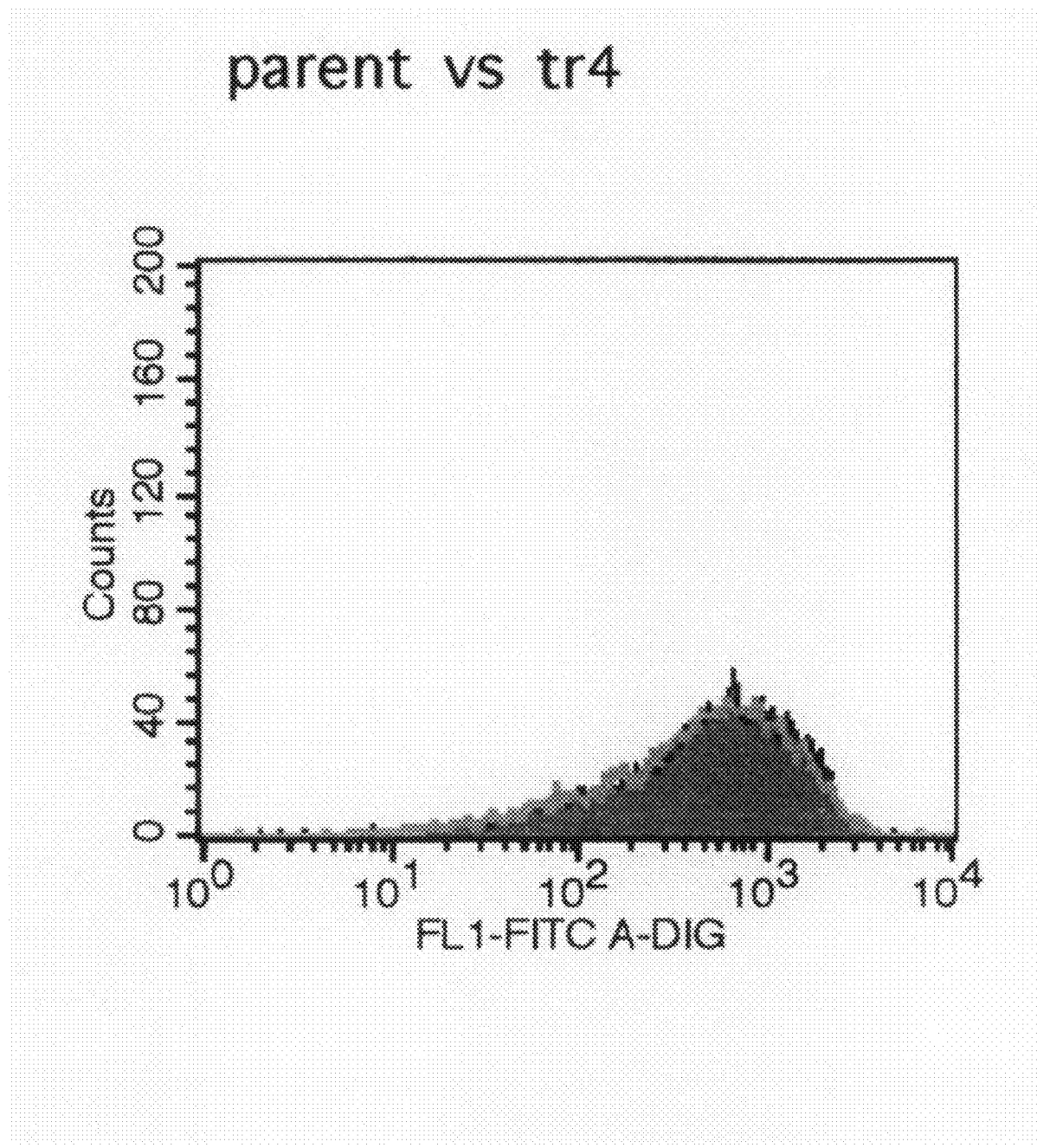
Figure 6A:
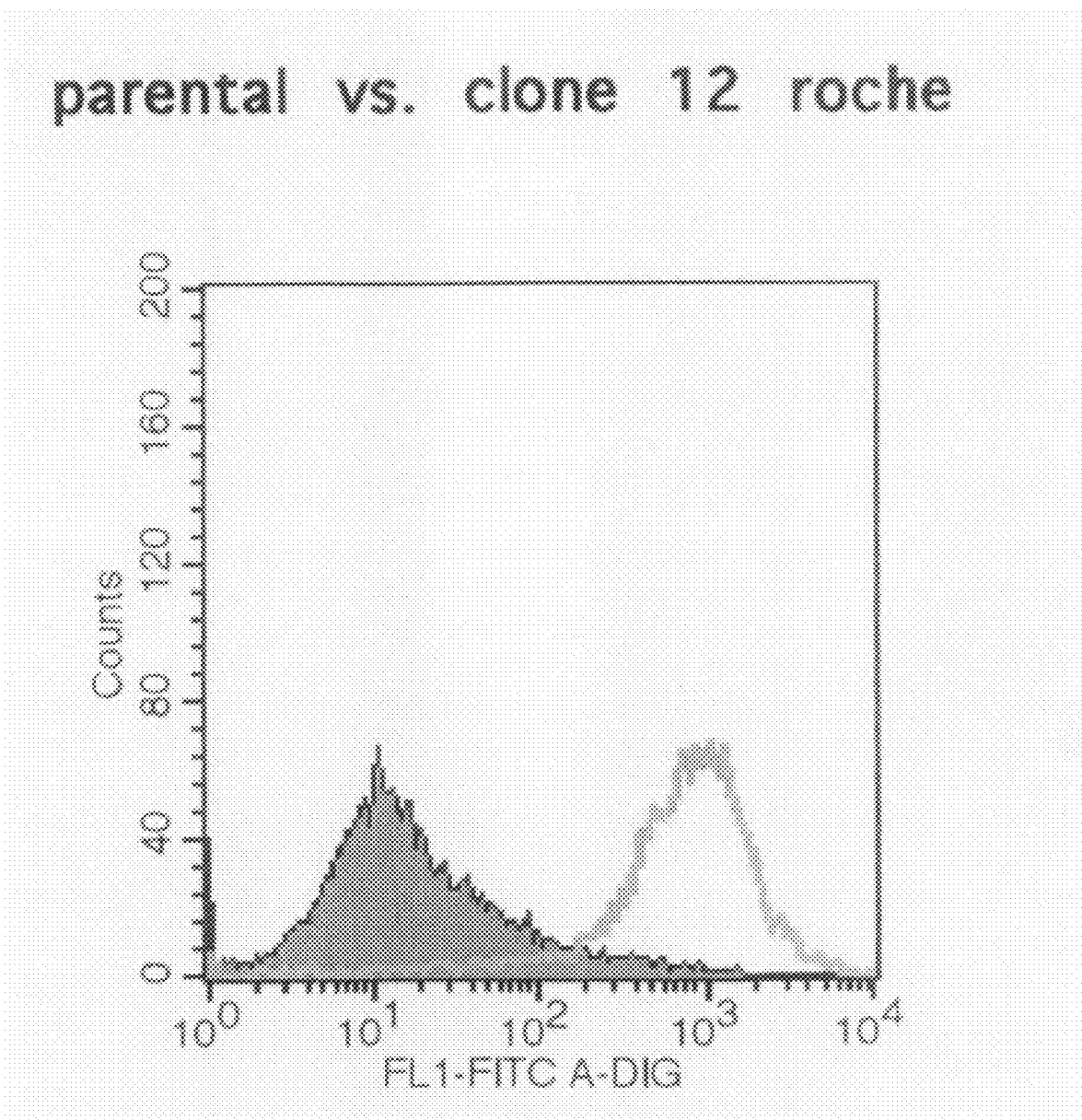
Figure 6B:
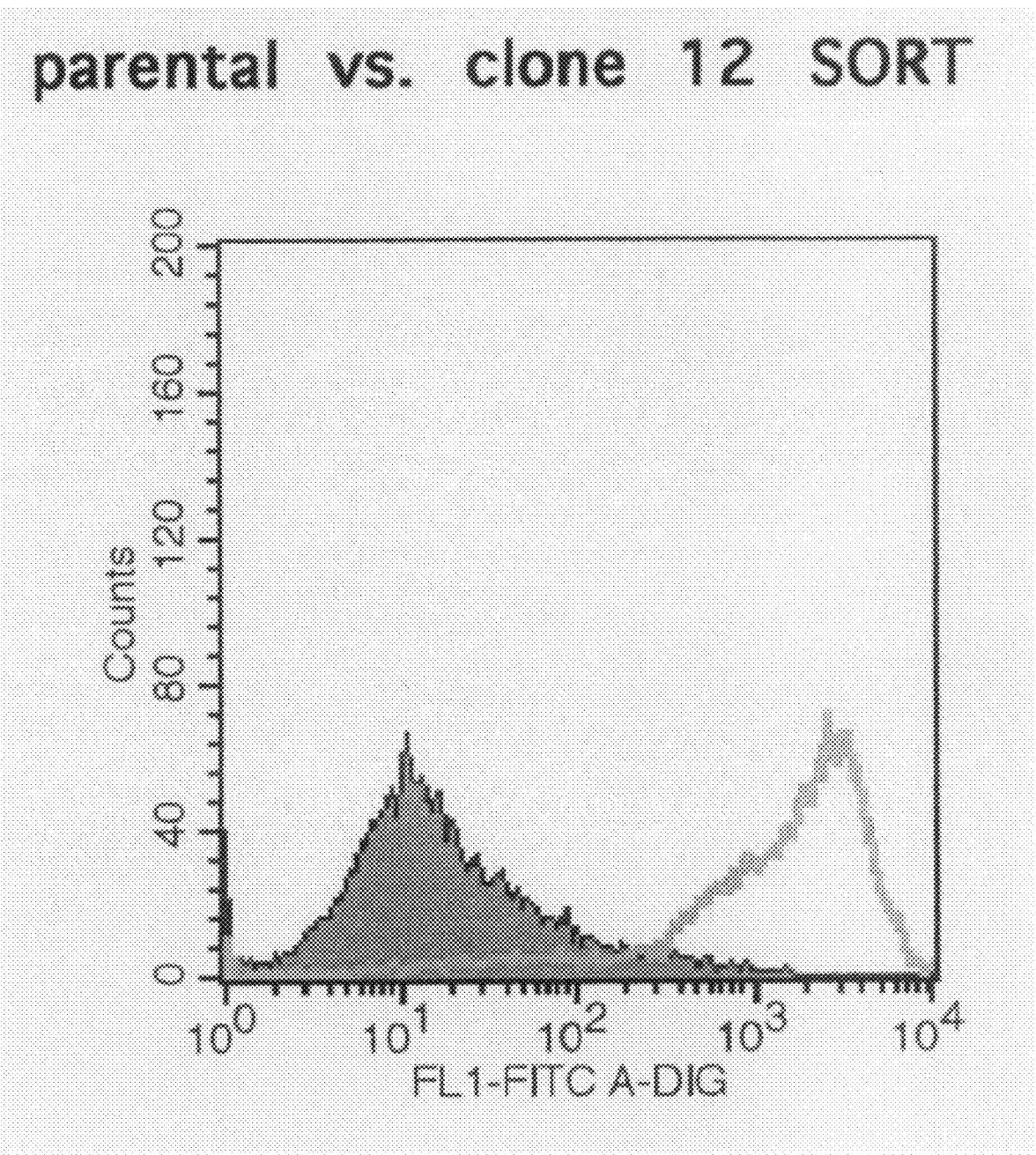
Figure 6C:
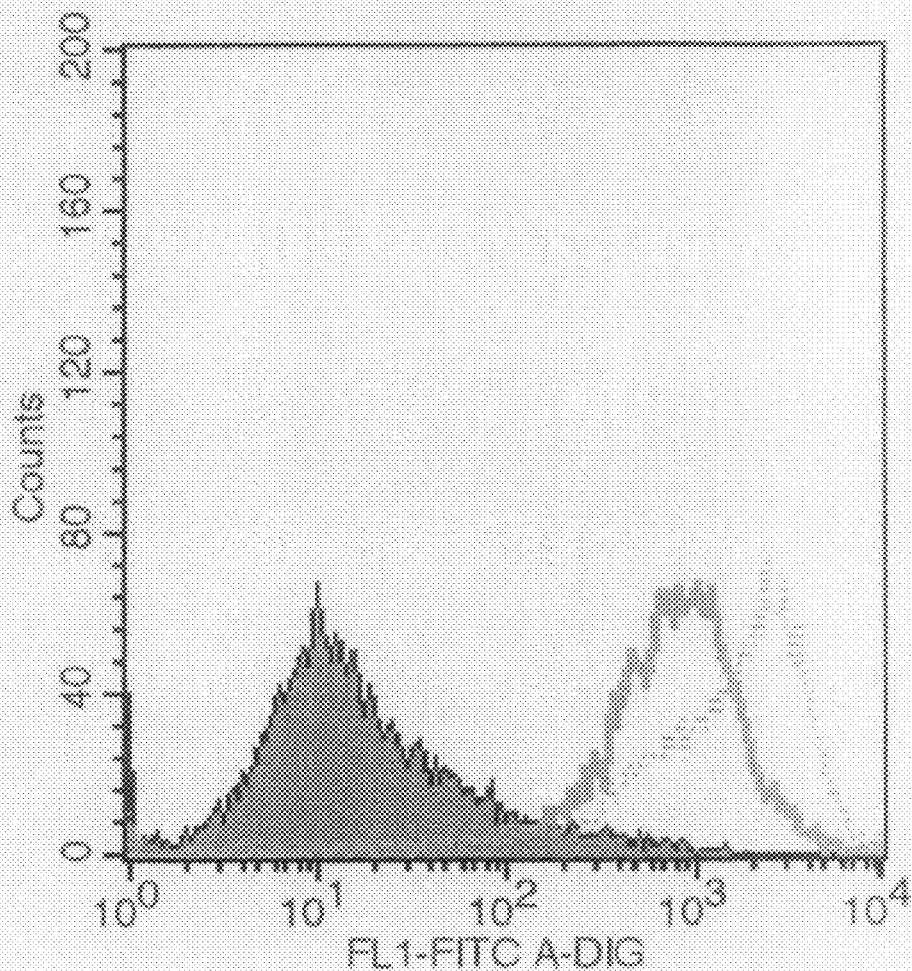

Kistner et al., "Development of a Vero Cell-Derived Influenza Whole Virus Vaccine", *Dev Biol Stand*, (1999), pp. 101-110, vol. 98, Karger.

Kumari et al., "Receptor binding specificity of recent human H3N2 influenza viruses", *Virology Journal*, May 9, 2007, pp. 1-12, vol. 4, No. 42, BioMed Central Ltd.

Lau et al., "Abortive Infection of Vero Ceils by an Influenza A Virus (FPV)", *Virology*, (1995), pp. 212-225, The Academic Press, Inc.

Lee et al., "Alteration of Terminal Glycosylation Sequences on N-Linked Oligosaccharides of Chinese Hamster Ovary Cells by Expression of β-Galactoside α2,6-Sialyltransferase", *The Journal of Biological Chemistry*, Aug. 1989, pp. 13848-13855, vol. 264, No. 23, The American Society of Biochemistry and Molecular Biology, Inc., USA.

Lubinieck, "Historical reflections on celll culture engineering", *Cytotechnology*, (1998), pp. 139-145, vol. 28, Kluwer Academic Publishers, The Netherlands.

Matrosovich et al., "Overexpression of the α2,6-Sialyltransferase in MDCK Cells Increases influenza Virus Sensitivity to Neuraminidase Inhibitors", *Journal of Virology*, Aug. 2003, pp. 8418-8425, vol. 77, No. 15, American Society for Microbiology, USA.

Monaco et al., "Genetic Engineering of α2,6-sialyltransferase in recombinant CHO cells and its effects on the sialylation of recombinant Interferon-γ", *Cytotechnology*, (1996), pp. 197-203, vol. 22, Kluwer Academic Plublishers, The Netherlands.

Murphy, "Use of Live Attenuated Cold-Adapted Influenza a Reassortant Virus Vaccines in Infants Children, Young Adults, and Elderly Adults", *Infect. Dis. Clin. Pract.*, (1993), pp. 174-181, vol. 2, No. 3, Williams & Wilkins, USA.

Nakamura et al., "Protein Synthesis in Vero Cells Abortively Infected with Influenza B Virus", *J. gen. Virol.*, (1981), pp. 199-202, vol. 56.

Patriarca, P.A., "Use of Cell Lines for the Production of Influenza Virus Vaccines; An Appraisal of Technical, Manufacturing, and Regulatory Considerations", *Biologics Consulting Group, Inc.*, Apr. 10, 2007, pp. 1-12, Initiative for Vaccine Research, World Health Organization, Geneva, Switzerland.

Pavelka et al., "Cell-Cell and Cell-Martix Contacts, Tight Junctions and Gap Junctions", *Functional Ultrastructure: An Atlas of Tissue Biology and Pathology*, (2005), pp. 156-159, Springer-Verlag/Wien, Austria.

Robertson et al., "High Growth Reassortant Influenza Vaccine Viruses: New Approaches to their Control", *Biologicals*, (1992), pp. 213-220, vol. 20.

Russell et al., "Avian and human receptor binding by hemagglutinins of influenza A viruses", *Glycoconj J.*, (2006), pp. 85-92, vol. 23, Springer Science+Business Media, LLC.

Shi et al., "The Teteaspanin CD9 Associated with Transmembrane TGFα and Regukates TGF-α-induced EGF Receptor Activation and Cell Proliferation", *The Jounal of Cell Biology*, Feb. 7, 2000, pp. 591-601, vol. 148, No. 3, The Rockefeller Univ. Press.

Wiebe et al., "A Multifaceted Approach to Assure that Recombinant tPA is Free of Adventitious Virus", *Advances in Animal Cell Biology and Technology*, (1989), pp. 68-71, Butterworth-Heinemann, Great Britain.

Zhang et al., "Stable expression of human α-2,6-sisalytransferase in Chinese hamster ovary cells: functional consequences for human erythropetin expression and bioactivity", *Bichimica et Biophysica Acta*, (1998), pp. 441-452, vol. 1425, Elsevier Science B.V.

PCT Notification of Transmittal of the International Search Report and The Written Opinion of the International Searching Authority, or the Declaration, dated Oct. 2, 2009, 3 pages.

PCT International Search Report, dated Oct. 29, 2009, 6 pages.

PCT Written Opinion of the International Searching Authority, dated Oct. 29, 2009, 9 pages.

\* cited by examiner

PB clone 1 vs parental
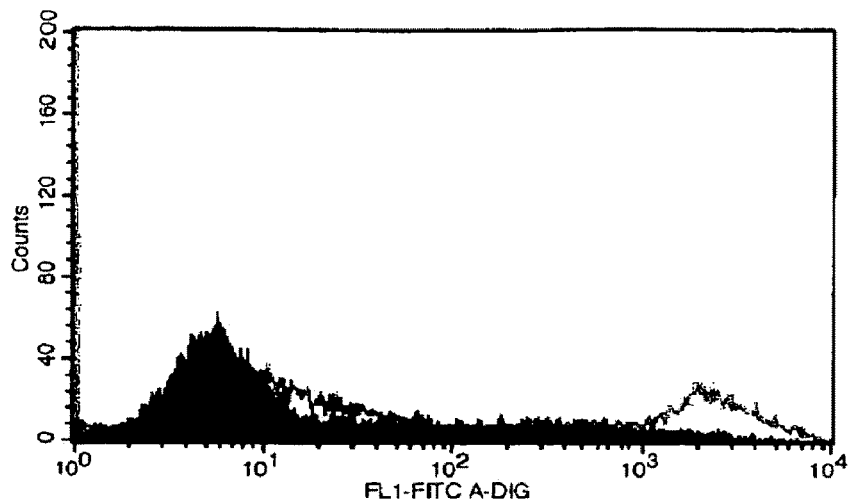
clone 1 vs parental
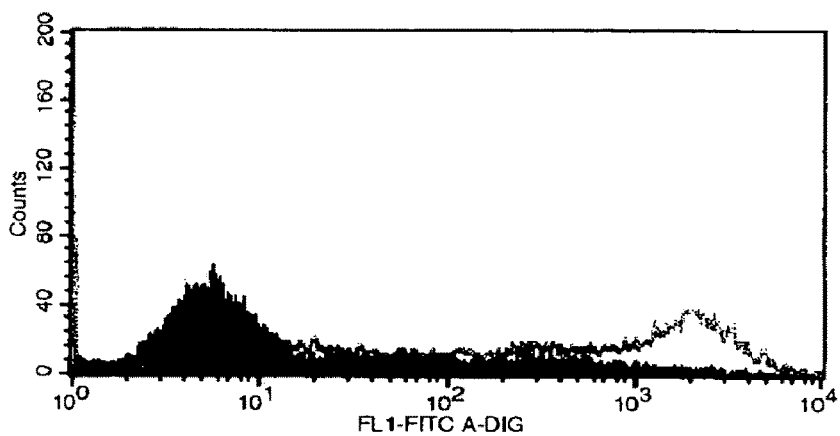
clone 3 vs parental
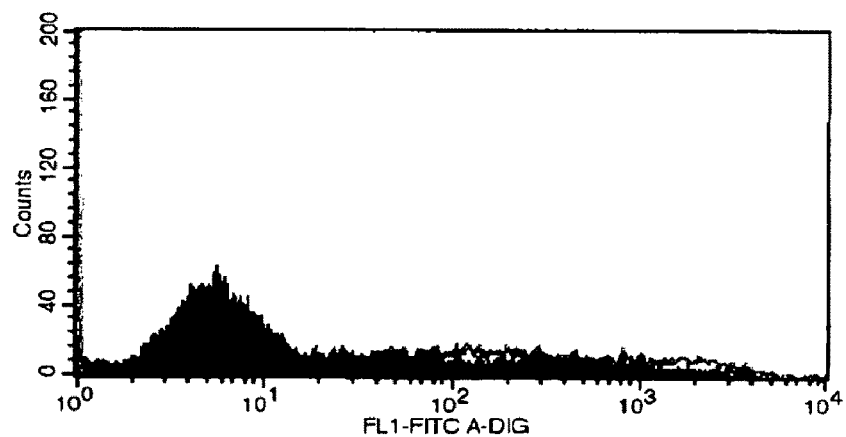
FIGURE 3

(A)
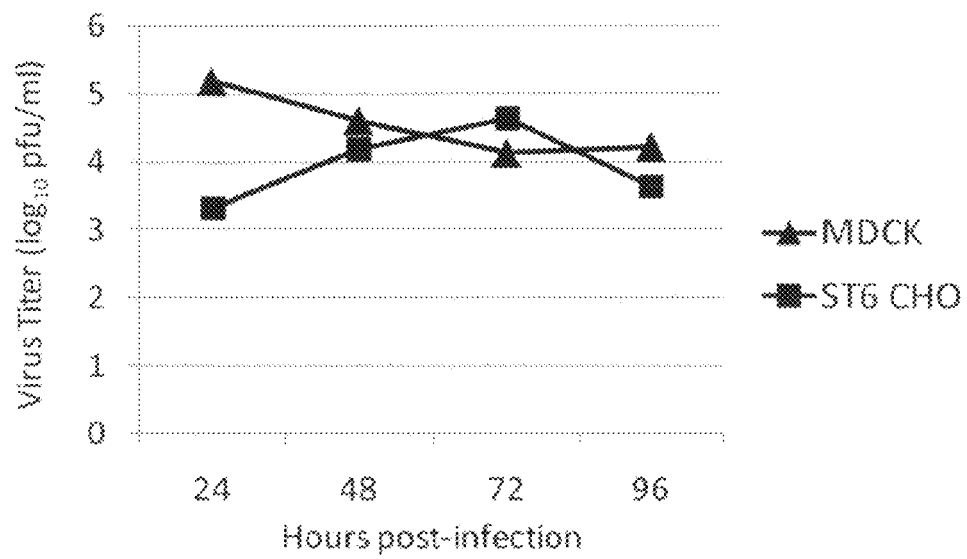
(B)
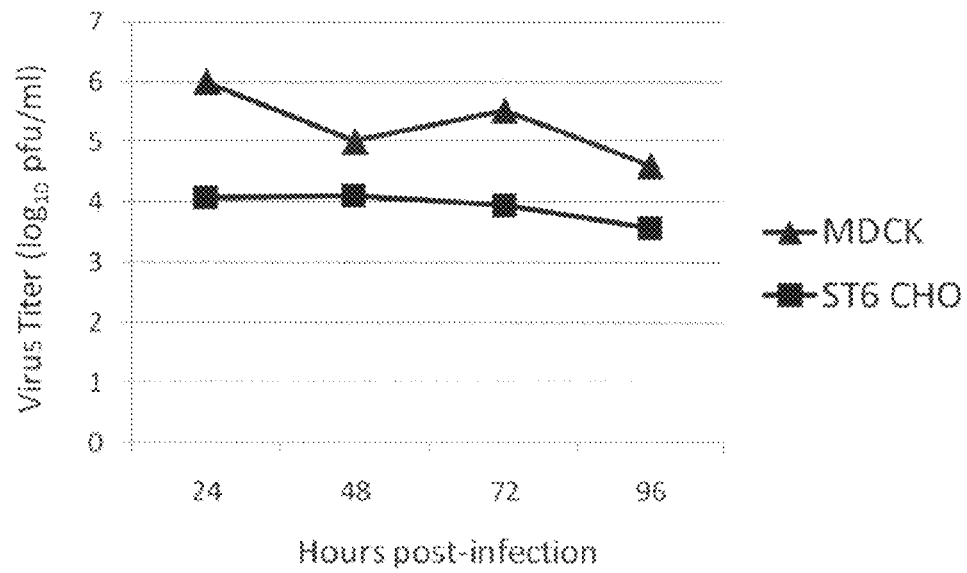
FIGURE 9 A & B

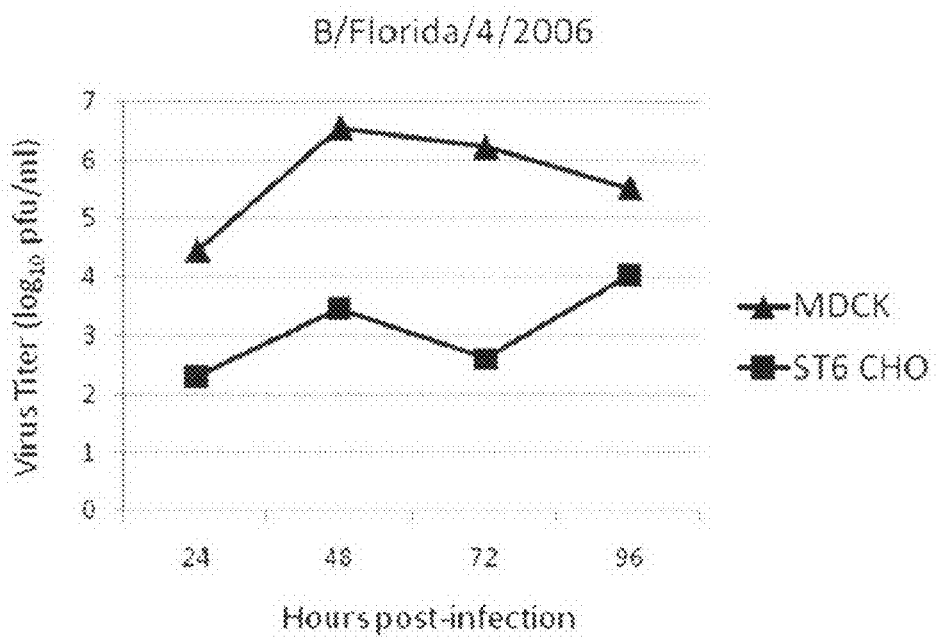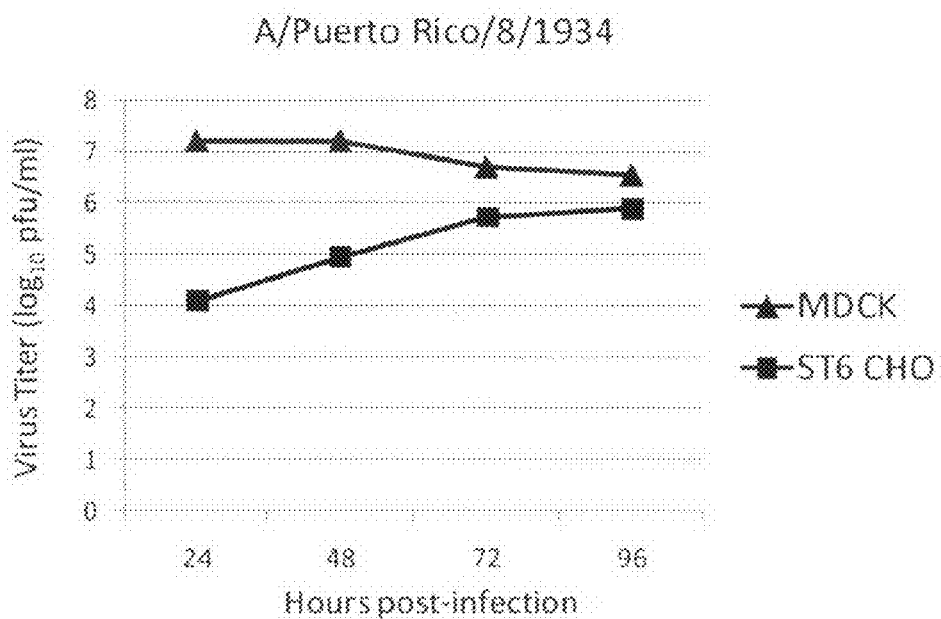
FIGURE 9 C & D

SEQUENCE LISTING

<160> NUMBER OF SEQ ID NOS: 9

<210> SEQ ID NO 1
<211> LENGTH: 1272
<212> TYPE: DNA
<213> ORGANISM: Homo sapiens
<220> FEATURE:
<221> NAME/KEY: modified_base
<222> LOCATION: (4)..(4)
<223> OTHER INFORMATION: a, c, g, t, unknown or other
<220> FEATURE:
<221> NAME/KEY: modified_base
<222> LOCATION: (6)..(6)
<223> OTHER INFORMATION: a, c, g, t, unknown or other
<220> FEATURE:
<221> NAME/KEY: modified_base
<222> LOCATION: (1269)..(1269)
<223> OTHER INFORMATION: a, c, g, t, unknown or other
<220> FEATURE:
<221> NAME/KEY: modified_base
<222> LOCATION: (1272)..(1272)
<223> OTHER INFORMATION: a, c, g, t, unknown or other

<400> SEQUENCE: 1

```
cgancncgtt acttagcttg ccgccccatg attcacacca acctgaagaa aaagttcagc      60
tgctgcgtcc tggtctttct ctgtttgca gtcatctgtg tgtggaagga aaagaagaaa      120
gggagttact atgattcctt taaattgcaa accaaggaat tccaggtgtt aaagagtctg     180
gggaaattgg ccatggggtc tgattcccag tctgtatcct caagcagcac ccaggacccc     240
cacaggggcc gccagaccct cggcagtctc agaggcctag ccaaggccaa accagaggcc     300
tccttccagg tgtggaacaa ggacagctct tccaaaaacc ttatccctag gctgcaaaag     360
atctggaaga attacctaag catgaacaag tacaaagtgt cctacaaggg gccaggacca     420
ggcatcaagt tcagtgcaga ggccctgcgc tgccacctcc gggaccatgt gaatgtatcc     480
atggtagagg tcacagattt tcccttcaat acctctgaat gggagggtta tctgcccaag     540
gagagcatta ggaccaaggc tgggccttgg ggcaggtgtg ctgttgtgtc gtcagcggga     600
tctctgaagt cctcccaact aggcagagaa atcgatgatc atgacgcagt cctgaggttt     660
aatggggcac ccacagccaa cttccaacaa gatgtgggca caaaaactac cattcgcctg     720
atgaactctc agttggttac cacagagaag cgcttcctca agacagtttt gtacaatgaa     780
```

```
ggaatcctaa ttgtatggga cccatctgta taccactcag atatcccaaa gtggtaccag      840
aatccggatt ataatttctt taacaactac aagacttatc gtaagctgca ccccaatcag      900 ccctttttaca tcctcaagcc ccagatgcct tgggagctat gggacattct tcaagaaatc    960
tccccagaag agattcagcc aaaccccca tcctctggga tgcttggtat catcatcatg     1020
atgacgctgt gtgaccaggt ggatatttat gagttcctcc catccaagcg caagactgac    1080
gtgtgctact actaccagaa gttcttcgat agtgcctgca cgatgggtgc ctaccacccg    1140
ctgctctatg agaagaattt ggtgaagcat ctcaaccagg gcacagatga ggacatctac    1200
ctgcttggaa aagccacact gcctggcttc cggaccattc actgctaact cgagtcagag    1260
gccgtaacng cn                                                         1272
```

```
<210> SEQ ID NO 2
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
aagcttgccg ccaccatgat tcacaccaac                                       30

<210> SEQ ID NO 3
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
cggcgcctcg agttagcagt gaatggt                                          27

<210> SEQ ID NO 4
<211> LENGTH: 415
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: Any amino acid

<400> SEQUENCE: 4

Arg Xaa Arg Tyr Leu Ala Cys Arg Pro Met Ile His Thr Asn Leu Lys
1               5                   10                  15

Lys Lys Phe Ser Cys Cys Val Leu Val Phe Leu Leu Phe Ala Val Ile
            20                  25                  30

Cys Val Trp Lys Glu Lys Lys Gly Ser Tyr Tyr Asp Ser Phe Lys
        35                  40                  45

Leu Gln Thr Lys Glu Phe Gln Val Leu Lys Ser Leu Gly Lys Leu Ala
    50                  55                  60

Met Gly Ser Asp Ser Gln Ser Val Ser Ser Ser Thr Gln Asp Pro
65                  70                  75                  80

His Arg Gly Arg Gln Thr Leu Gly Ser Leu Arg Gly Leu Ala Lys Ala
                85                  90                  95

Lys Pro Glu Ala Ser Phe Gln Val Trp Asn Lys Asp Ser Ser Ser Lys
            100                 105                 110

Asn Leu Ile Pro Arg Leu Gln Lys Ile Trp Lys Asn Tyr Leu Ser Met
        115                 120                 125
```

```
Asn Lys Tyr Lys Val Ser Tyr Lys Gly Pro Gly Pro Gly Ile Lys Phe
            130                 135                 140

Ser Ala Glu Ala Leu Arg Cys His Leu Arg Asp His Val Asn Val Ser
145                 150                 155                 160

Met Val Glu Val Thr Asp Phe Pro Phe Asn Thr Ser Glu Trp Glu Gly
                165                 170                 175

Tyr Leu Pro Lys Glu Ser Ile Arg Thr Lys Ala Gly Pro Trp Gly Arg
                180                 185                 190

Cys Ala Val Val Ser Ser Ala Gly Ser Leu Lys Ser Ser Gln Leu Gly
            195                 200                 205

Arg Glu Ile Asp Asp His Asp Ala Val Leu Arg Phe Asn Gly Ala Pro
210                 215                 220

Thr Ala Asn Phe Gln Gln Asp Val Gly Thr Lys Thr Thr Ile Arg Leu
225                 230                 235                 240

Met Asn Ser Gln Leu Val Thr Thr Glu Lys Arg Phe Leu Lys Asp Ser
                245                 250                 255

Leu Tyr Asn Glu Gly Ile Leu Ile Val Trp Asp Pro Ser Val Tyr His
                260                 265                 270

Ser Asp Ile Pro Lys Trp Tyr Gln Asn Pro Asp Tyr Asn Phe Phe Asn
            275                 280                 285

Asn Tyr Lys Thr Tyr Arg Lys Leu His Pro Asn Gln Pro Phe Tyr Ile
290                 295                 300

Leu Lys Pro Gln Met Pro Trp Glu Leu Trp Asp Ile Leu Gln Glu Ile
305                 310                 315                 320

Ser Pro Glu Glu Ile Gln Pro Asn Pro Pro Ser Ser Gly Met Leu Gly
                325                 330                 335

Ile Ile Ile Met Met Thr Leu Cys Asp Gln Val Asp Ile Tyr Glu Phe
                340                 345                 350

Leu Pro Ser Lys Arg Lys Thr Asp Val Cys Tyr Tyr Gln Lys Phe
            355                 360                 365

Phe Asp Ser Ala Cys Thr Met Gly Ala Tyr His Pro Leu Leu Tyr Glu
            370                 375                 380

Lys Asn Leu Val Lys His Leu Asn Gln Gly Thr Asp Glu Asp Ile Tyr
385                 390                 395                 400

Leu Leu Gly Lys Ala Thr Leu Pro Gly Phe Arg Thr Ile His Cys
                405                 410                 415

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
tggtatcaga agccagacta c                                             21

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
ccctcattga gatgcttcac c                                             21
```

```
<210> SEQ ID NO 7
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
tcatgaagtg tgacgttgac atccgt                                           26

<210> SEQ ID NO 8
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
cttagaagca ttagcggtgc acgatg                                           26

<210> SEQ ID NO 9
<211> LENGTH: 8
<212> TYPE: PRT
<213> ORGANISM: Homo sapiens
<220> FEATURE:
<221> NAME/KEY: MOD_RES
<222> LOCATION: (7)..(8)
<223> OTHER INFORMATION: Any amino acid

<400> SEQUENCE: 9

Leu Glu Ser Glu Ala Val Xaa Xaa
1               5
```

CELL-BASED SYSTEMS FOR PRODUCING INFLUENZA VACCINES

The present application claims priority to U.S. Provisional Application No. 61/169,548, filed Apr. 15, 2009, and U.S. Provisional Application No. 61/060,653, filed on Jun. 11, 2008, both of which are incorporated herein by reference in their entirety.

FIELD OF THE INVENTION

The present invention relates to a cell-based method for producing influenza virus vaccines by enriching the population of surface-bound α2,6-sialic acid receptors on a cell surface, such as on a Chinese Hamster Ovary cell surface.

BACKGROUND

Influenza vaccines have been manufactured for over 70 years using a process that involves infecting embryonated chicken eggs with influenza virus. The process is difficult to automate, labor-intensive, costly and creates significant risk of contamination. The entire production process requires detailed planning that begins up to 8 months prior to vaccine delivery and leaves little room for error. For instance, the 2004 worldwide influenza vaccine shortage was the result of contamination at a flu vaccine manufacturing facility. As highly pathogenic strains continue to emerge and spread, the shortcomings of egg-based manufacturing are becoming even more apparent.

Another significant drawback to current vaccine manufacturing is poor virus yield. Vaccine production includes a significant fixed cost component, reaching 90% of the total early stage manufacturing costs. Once many of the fixed costs have been recovered, however, substantial long-term variable costs still remain. It is estimated that with current egg-based production methods variable costs can run as high as 37% of the price per vaccine dose depending on the volume produced. Hence, even a two-fold increase in virus yield could have substantial impact on the cost of manufacturing and the availability of supply. Rapid increases in supply would be particularly important during a regional or worldwide pandemic.

To address the issues of contamination, production time and yield, influenza vaccine manufacturers are developing cell-based manufacturing systems, such as viral production in MDCK (Madin-Darby Canine Kidney) cells, Vero (African green monkey kidney) cells and PER-C6® (embryonic human retinal) cells. A 2007 report commissioned by the Initiative for Vaccine Research at the World Health Organization recognized these as the "three leading candidates (Vero, PER.C6 and MDCK)" of "mammalian cell lines that have been documented to support sufficient replication of influenza viruses." See "Use of Cell Lines for the Production of Influenza Virus Particles," Peter A. Patriarca, M.D., Biologics Consulting Group, Inc., USA, commissioned by WHO, Apr. 10, 2007.

However, MDCK cells are inherently tumorigenic, while Vero and PER-C6® cells have low virus yields and can have problematic side effects. For instance, the 2007 WHO report indicated that phase II/III trials of a whole-virion influenza vaccine produced in Vero cells was "suspended due to a higher-than-expected rate of fever and associated symptoms among trial participants." See footnote 1 at page 5 of the WHO/Patriarca report. Thus, as of 2007, government authorities recognized that the mechanism for immortalization of Vero and MDCK cells was unknown, and that therefore a vaccine developer would have to "make every effort to detect any unknown agent that could potentially be oncogenic." See WHO/Patriarca report at page 10. Accordingly, Europe and the United States expect rigorous testing of the viral seed for extraneous agents in accordance with both Ph. Eur. monograph 2.6.16 and 21 C.F.R. §630.35. Development of a safe, high yielding mammalian cell line, therefore, would be a significant improvement to existing influenza vaccine manufacturing practices.

SUMMARY OF THE INVENTION

An aspect of the present invention is a cell culture-based method for producing influenza virus, comprising (A) infecting a Chinese Hamster Ovary cell (CHO) with an influenza virus, wherein the CHO cell (i) expresses at least one copy of a 2,6-sialyltransferase gene (ST6GAL 1), and (ii) has an increased cell surface expression of 2,6-linked sialic acids; and (B) isolating influenza viruses produced from the CHO cell. In one embodiment, the 2,6-sialyltransferase gene is a mammalian 2,6-sialyltransferase gene. In one embodiment, the 2,6-sialyltransferase gene is from a human, primate, mouse, rat, pig, cattle, sheep, dog, cat, horse, guinea pig, or rodent. In one embodiment, the 2,6-sialyltransferase gene is a human 2,6-sialyltransferase gene. A CHO cell that expresses at least one 2,6-sialyltransferase gene may be referenced herein as CHO-ST6GAL1 or as described in the Detailed Description below. In one embodiment, the CHO cell is transformed with one or more ST6GAL 1 genes. In another embodiment, the CHO cell is mutagenized to express more 2,6-linked sialic acid receptors than a non-mutagenized CHO cell.

In another embodiment, the susceptibility of the CHO cell, which expresses ST6GAL 1, to influenza virus infection is greater than a CHO cell which does not express the ST6GAL 1 gene. The present invention is not limited to the expression of a ST6GAL 1 gene in CHO cells only. One or more copies of a ST6GAL 1 gene may be integrated into other cell types, such as into MDCK cells, Vero cells, and PER-C6® cells.

In another embodiment, the CHO cell yields a higher pfu/ml titer of influenza virus compared to a CHO cell which does not express the ST6GAL 1 gene. In one embodiment, the pfu/ml titer of influenza virus is at least about 2 times higher than the pfu/ml titer obtainable from a CHO cell which does not express the ST6GAL 1 gene. In another embodiment, the pfu/ml titer of influenza virus is at least about 3 times higher, at least about 4 times higher, at least about 5 times higher, at least about 6 times higher, at least about 7 times higher, at least about 8 times higher, at least about 9 times higher, at least about 10 times higher, at least about 20 times higher, at least about 30 times higher, at least about 40 times higher, at least about 50 times higher, at least about 60 times higher, at least about 70 times higher, at least about 80 times higher, at least about 90 times higher, at least about 100 times higher, or more than at least about 100 times higher than the pfu/ml titer obtainable from a CHO cell which does not express the ST6GAL 1 gene.

In another embodiment, the ratio of virus yield titers (pfu/ml) between a recombinant CHO cell that expresses an 2,6-sialyltransferase gene to a wild type CHO cell is at least about: 2:1, 3:1, 4:1, 5:1, 6:1, 7:1, 8:1, 9:1, or 10:1, or more than 10:1. That is a recombinant CHO cell of the present invention that expresses an 2,6-sialyltransferase gene yields at least about 2-fold greater titer (pfu/ml) in virus particles than a wild type CHO cell.

In another embodiment, the method further comprises formulating the isolated influenza viruses into a vaccine.

Another aspect of the present invention is a Chinese Hamster Ovary cell (CHO) comprising cell-surface bound 2,6-linked sialic acids. In one embodiment, the CHO cell is grown in suspension or adherent monolayer in the presence of media with and without fetal bovine serum, or in serum-free media. In another embodiment, the CHO cell surface expresses little if any 2,3-linked sialic acids. In one embodiment, there are more 2,6-linked sialic acid receptors on the surface of the CHO-ST6GAL1 cell than there are on the cell surface of a wild-type CHO cell. In one embodiment, the majority of the CHO cell surface comprises 2,6-linked sialic acids.

In one embodiment, the genome of the CHO cell expresses at least one ST6GAL 1 gene. In another embodiment, the genome of the CHO cell expresses at least one human ST6GAL 1 gene. In another embodiment, multiple copies of the ST6GAL 1 gene, such as multiple copies of a human ST6GAL 1 gene, are expressed from the CHO cell genome.

Another aspect of the present invention is a stable cell line established from any of the ST6GAL 1-expressing CHO cells described herein. In one embodiment, such a CHO cell can be used for detection, analysis, and preparation of seed virus in addition to vaccine production.

Another aspect of the present invention is a cell culture-based method for producing influenza virus vaccine, comprising (A) infecting any of the ST6GAL 1-expressing CHO cells described herein with an influenza virus, and (B) isolating influenza viruses produced from the CHO cell; and (C) formulating the isolated influenza viruses into an influenza virus vaccine.

In one embodiment, a method of producing influenza vaccines according to the present invention further comprises incubating the CHO cells with lectins against 2,3-sialic acid receptors.

In one embodiment, the generation time for producing the influenza vaccine is about 12 weeks, about 13 weeks, about 14 weeks, about 15 weeks, about 16 weeks, about 17 weeks, about 18 weeks, about 19 weeks, about 20 weeks, about 21 weeks, about 22 weeks, or more than about 22 weeks, from the time of viral infection of the CHO cells. In another embodiment, the generation time for producing the influenza vaccine is about 12 weeks-16 weeks. In another embodiment, the generation time for producing the influenza vaccine is about 12 weeks-14 weeks. In another embodiment, the generation time for producing the influenza vaccine is about 12 weeks-13 weeks.

In another embodiment, a method of the present invention permits the infection of 2,500 to 10,000 liters, or more, of ST6GAL 1-expressing CHO cells with influenza virus. In one embodiment, about 2,500-9,000 liters of CHO cells are infected with virus. In another embodiment, about 2,500-8,000 liters of CHO cells are infected with virus. In another embodiment, about 2,500-6,000 liters of CHO cells are infected with virus. In another embodiment, the present invention is applicable to smaller volumes of CHO cell cultures, such as those used in disposable, one-time assays and tests. Thus, in another embodiment, a method of the present invention permits the infection of at least about 1, 2, 3, 4, 5 liters or more than 5 liters of ST6GAL 1-expressing CHO cells with influenza virus. In one embodiment, about 5-500 liters of CHO cells are infected with virus.

Another aspect of the present invention is an influenza virus produced from any of the cell culture-based method described herein.

Another aspect of the present invention is an influenza vaccine, comprising any of the influenza viruses produced by the cell culturing methods disclosed herein, such as via expression and production in ST6GAL 1-expressing CHO cells. In one embodiment, an influenza vaccine includes but is not limited to live viruses, inactivated viruses, whole viruses, split viruses, virosomal viruses, and viral surface antigens. In another embodiment, a vaccine of the present invention may include an adjuvant.

Figure 8:
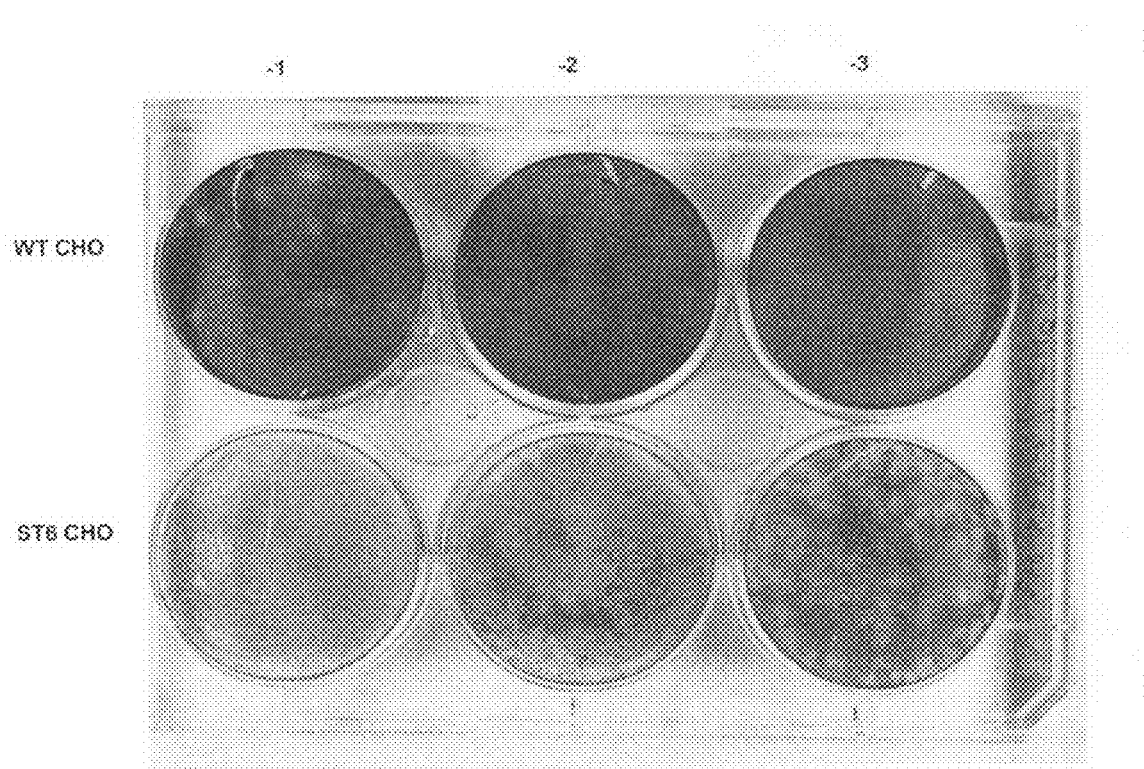
Figure 10A:
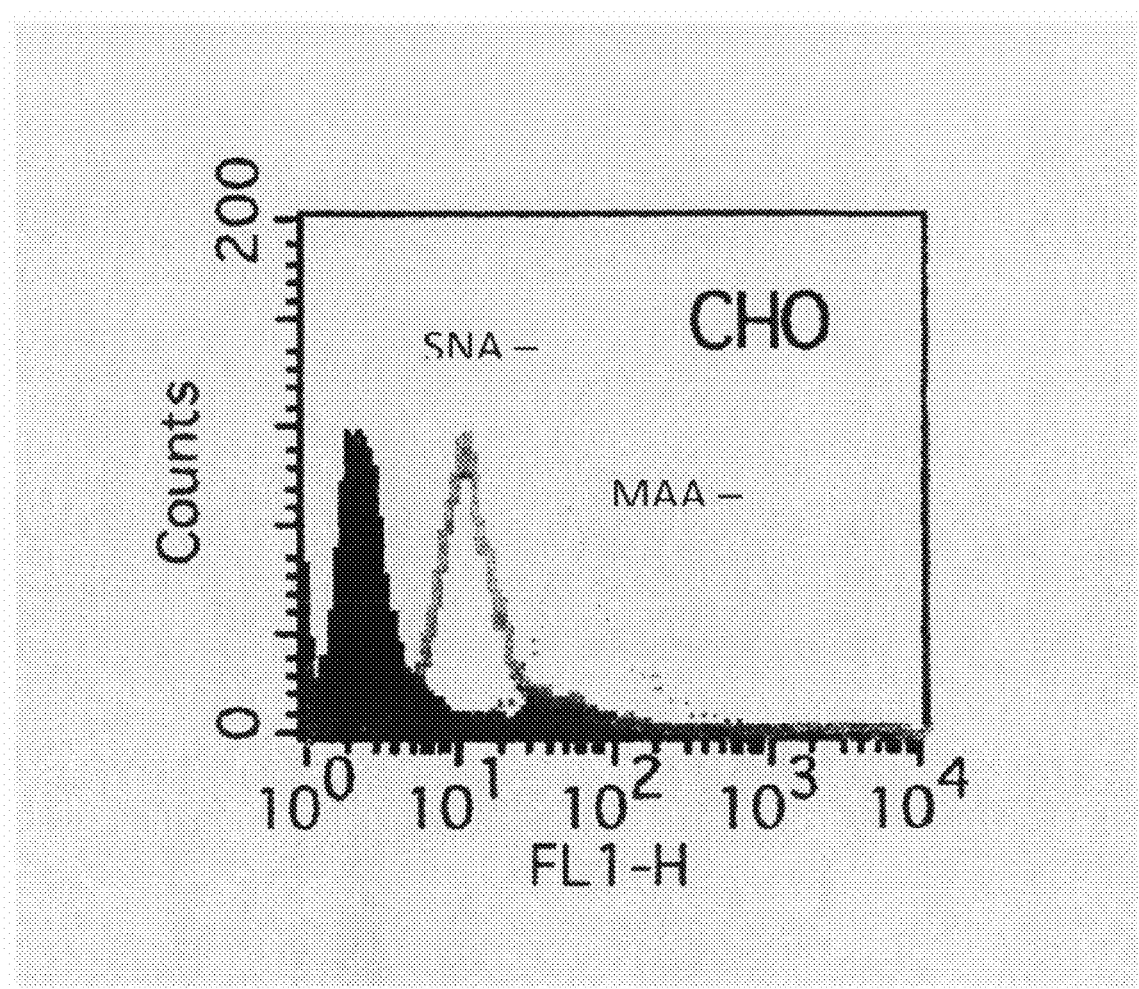
Figure 10B:
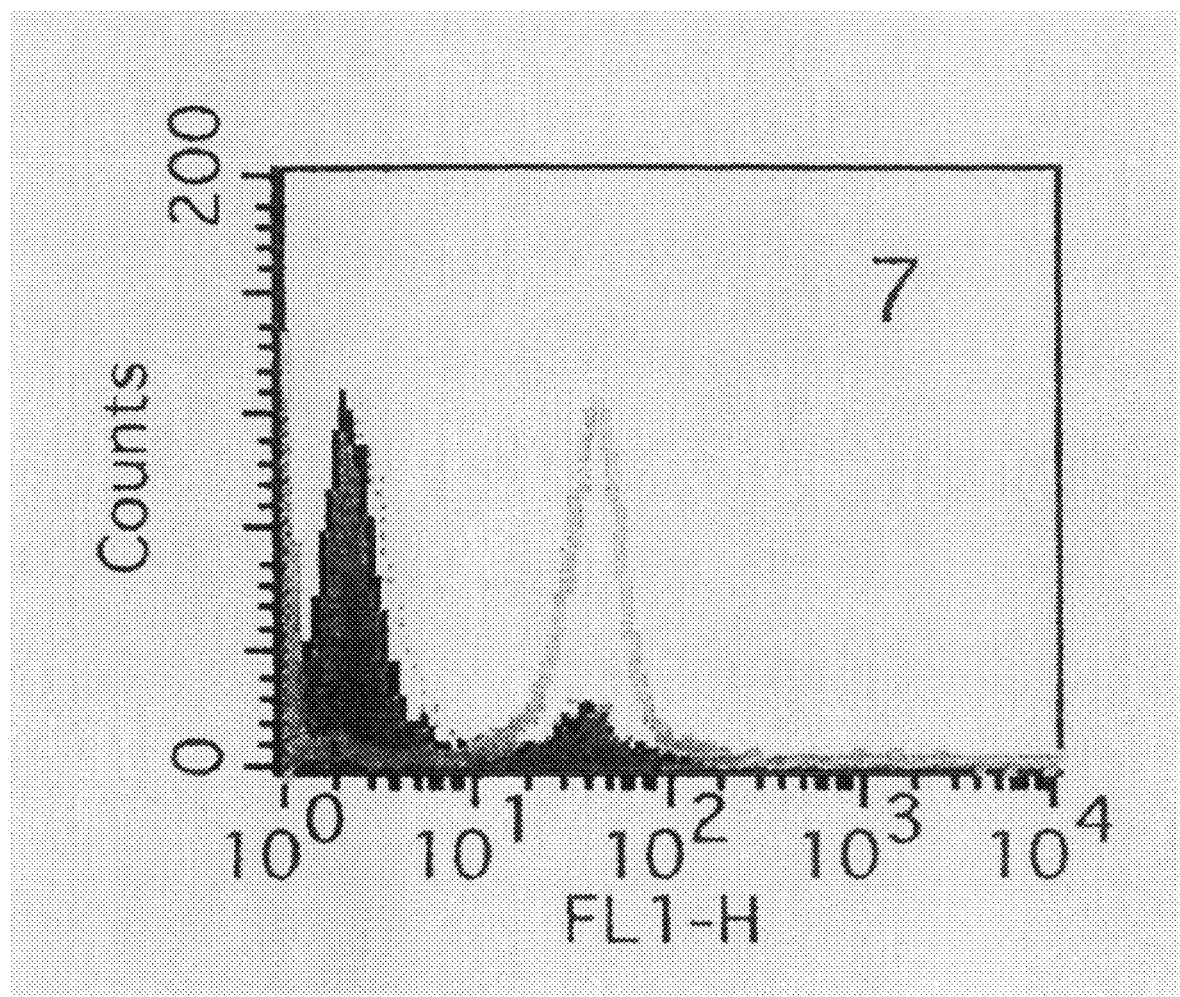
Figure 10C:
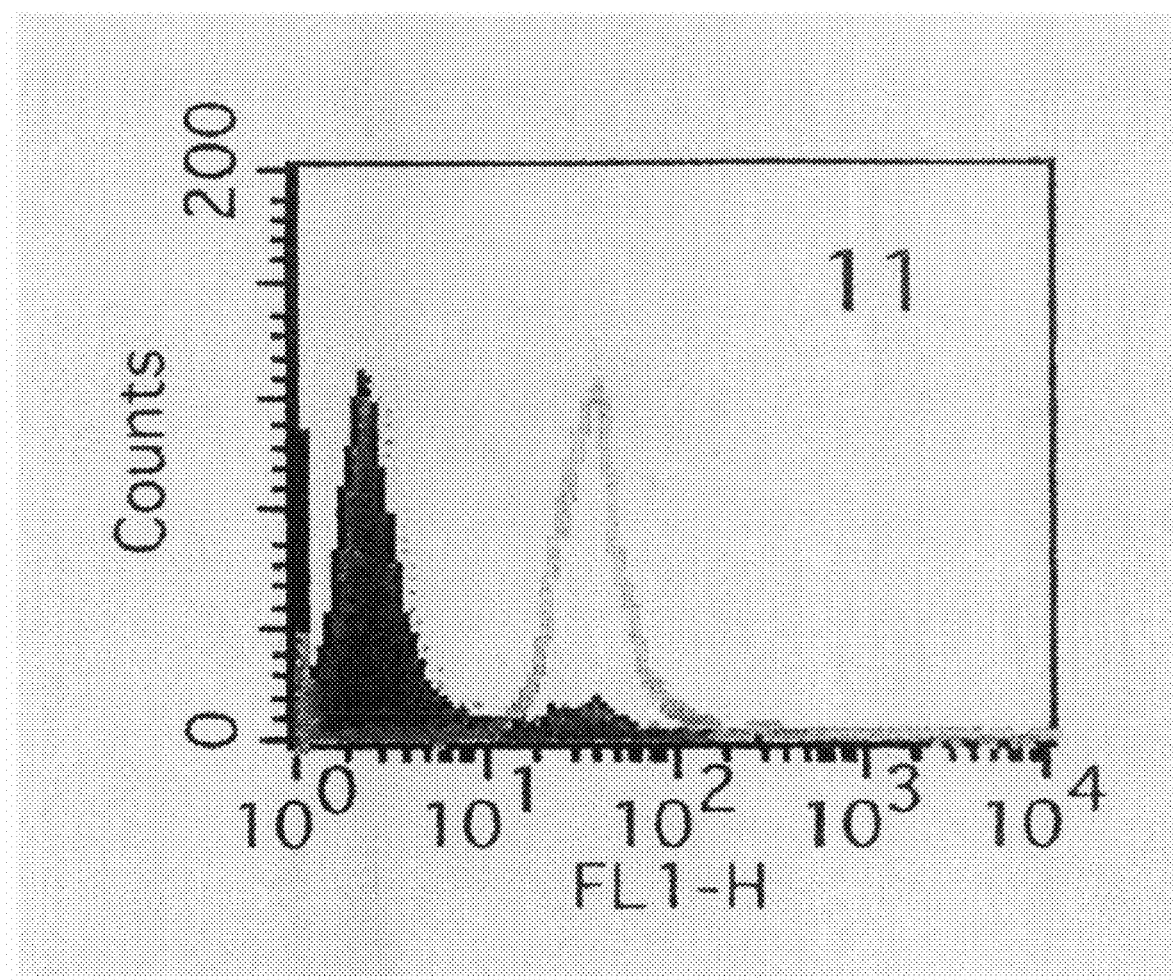
Figure 10D:
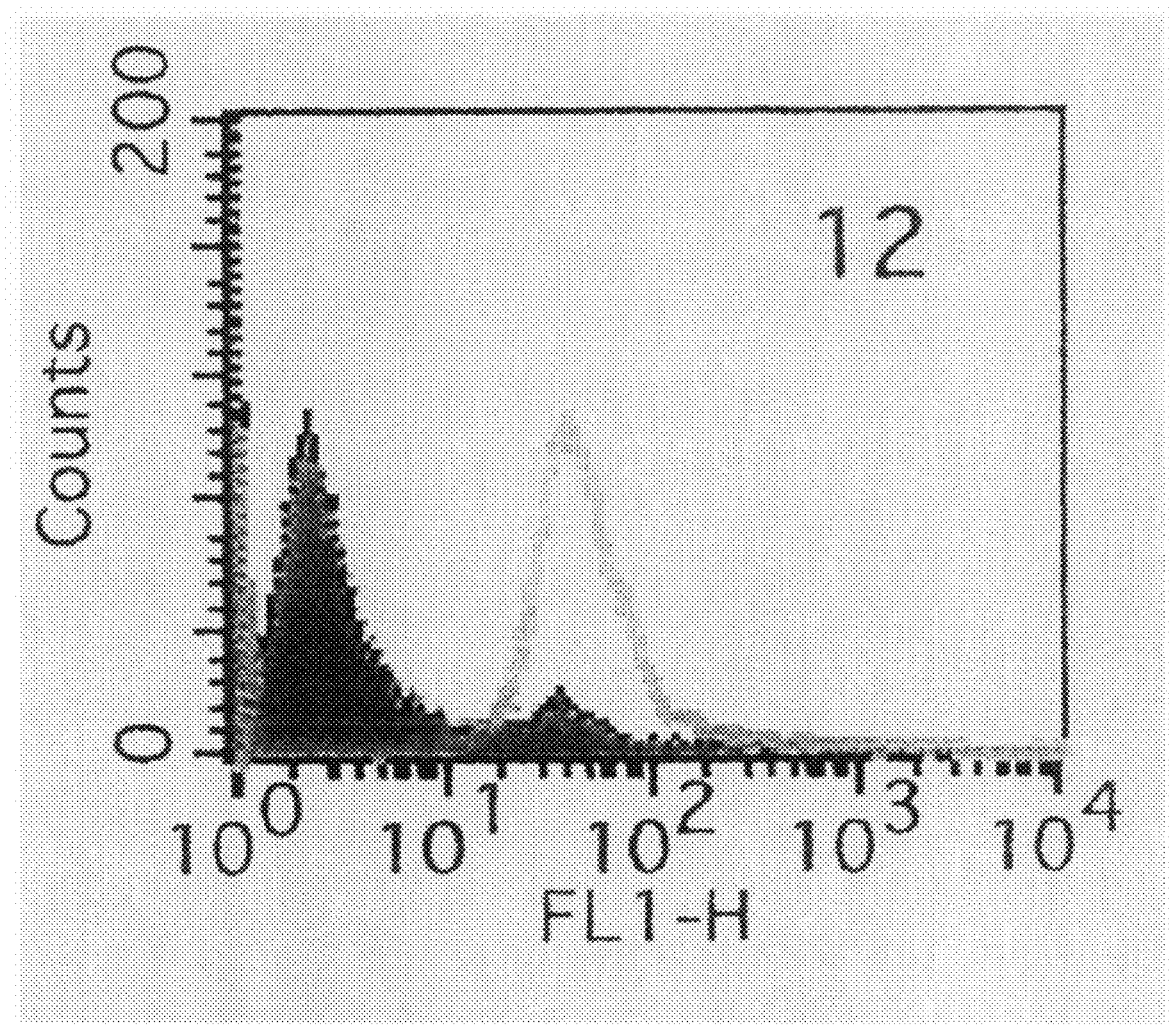
Figure 10E:
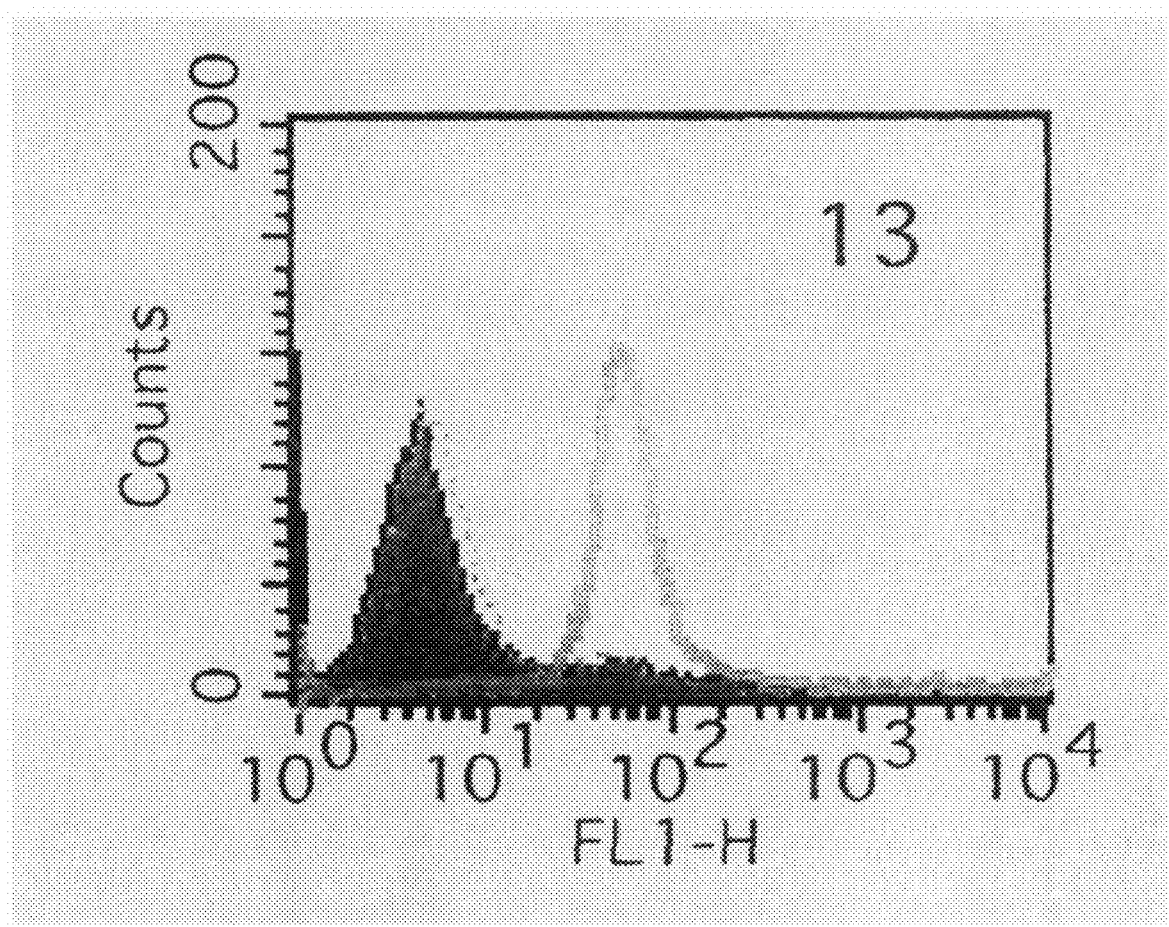
Figure 10F:
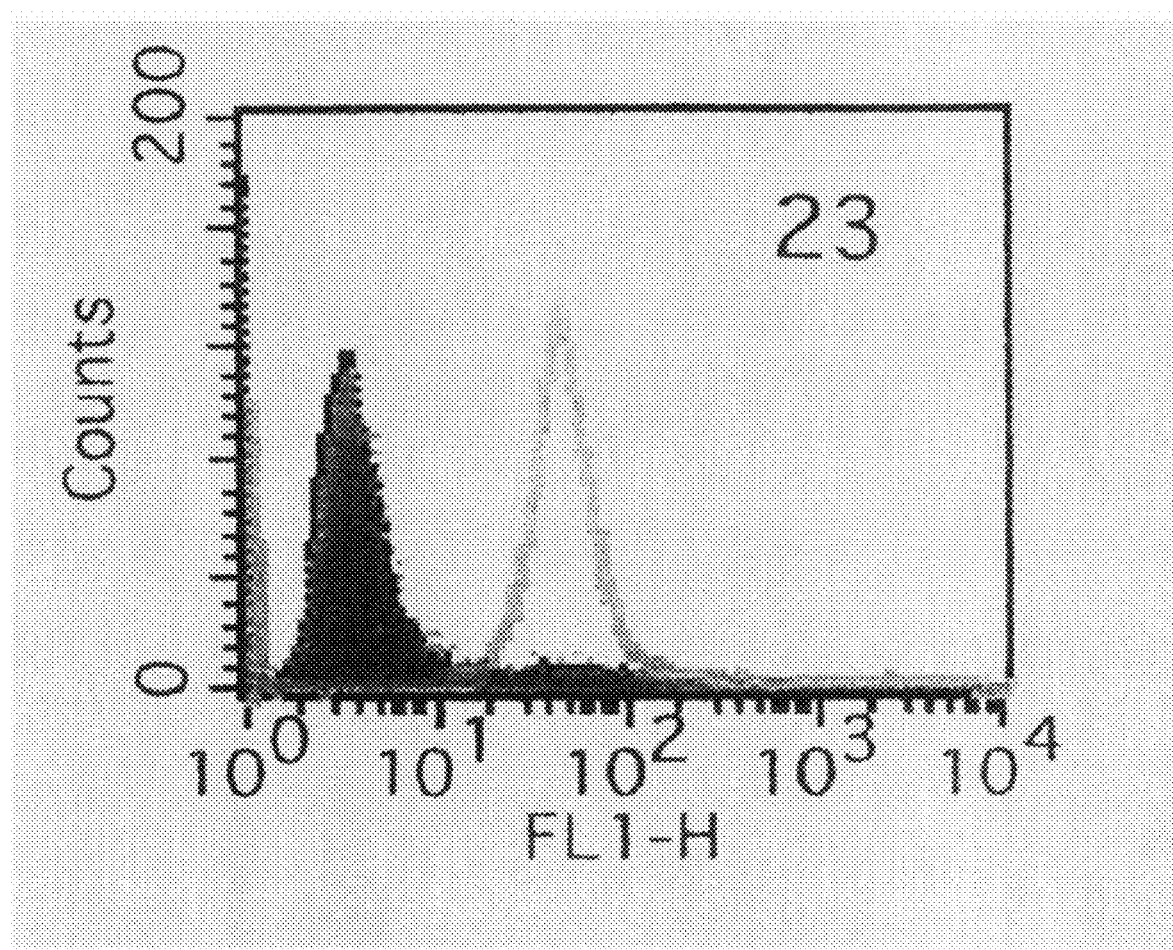
Figure 10G:
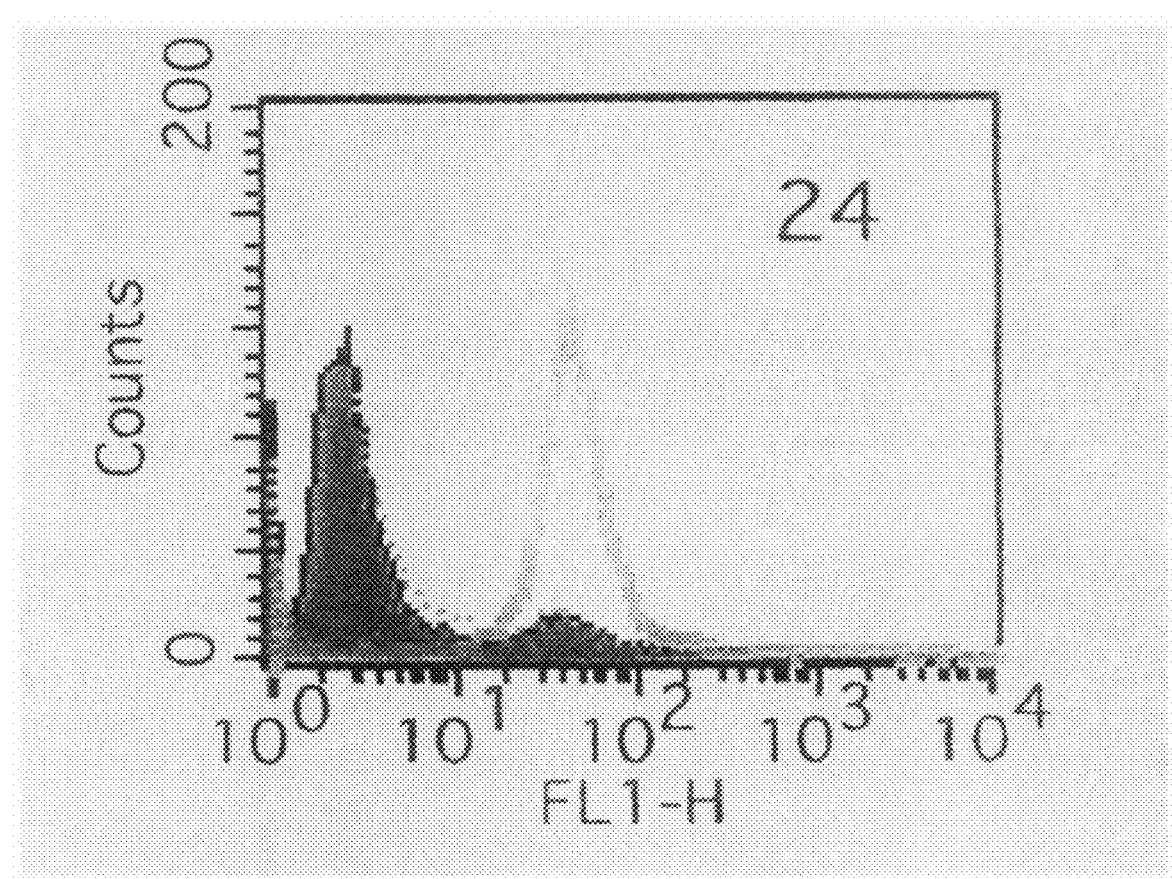
Figure 10H:
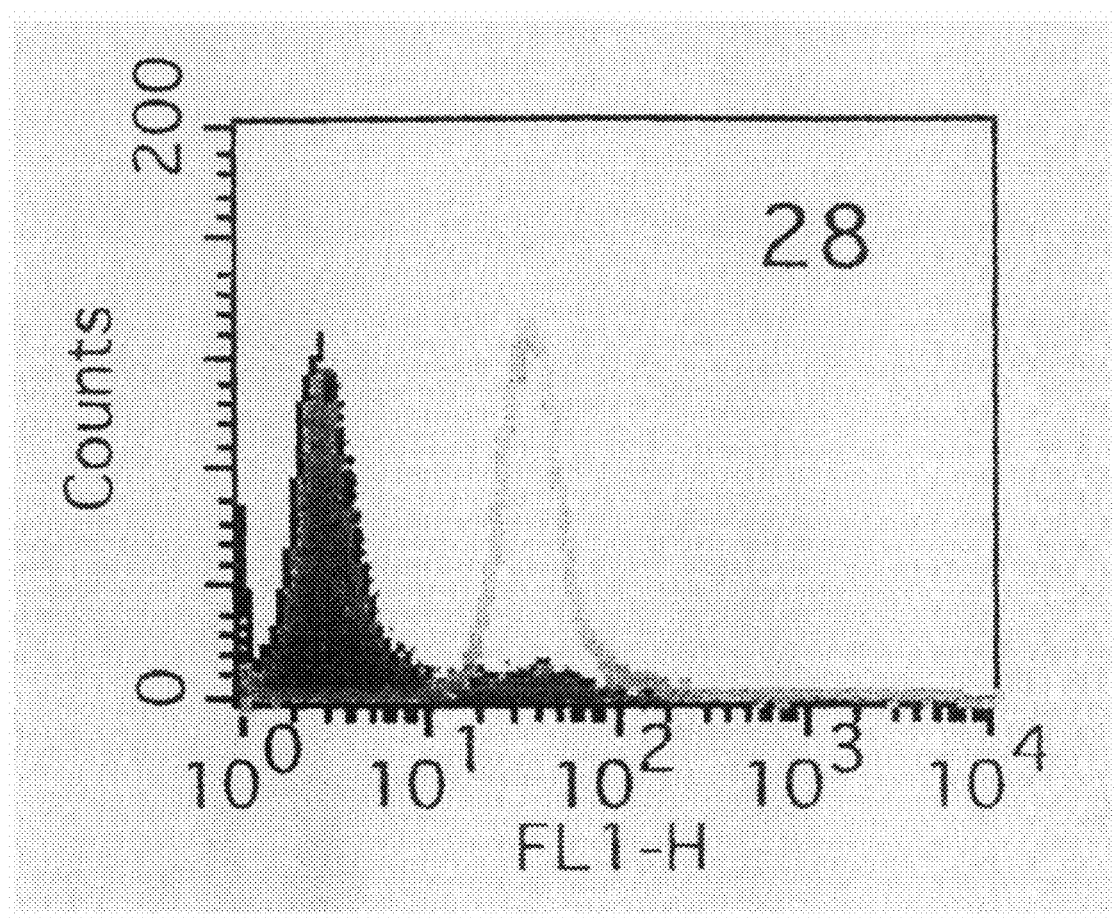
Figure 10I:
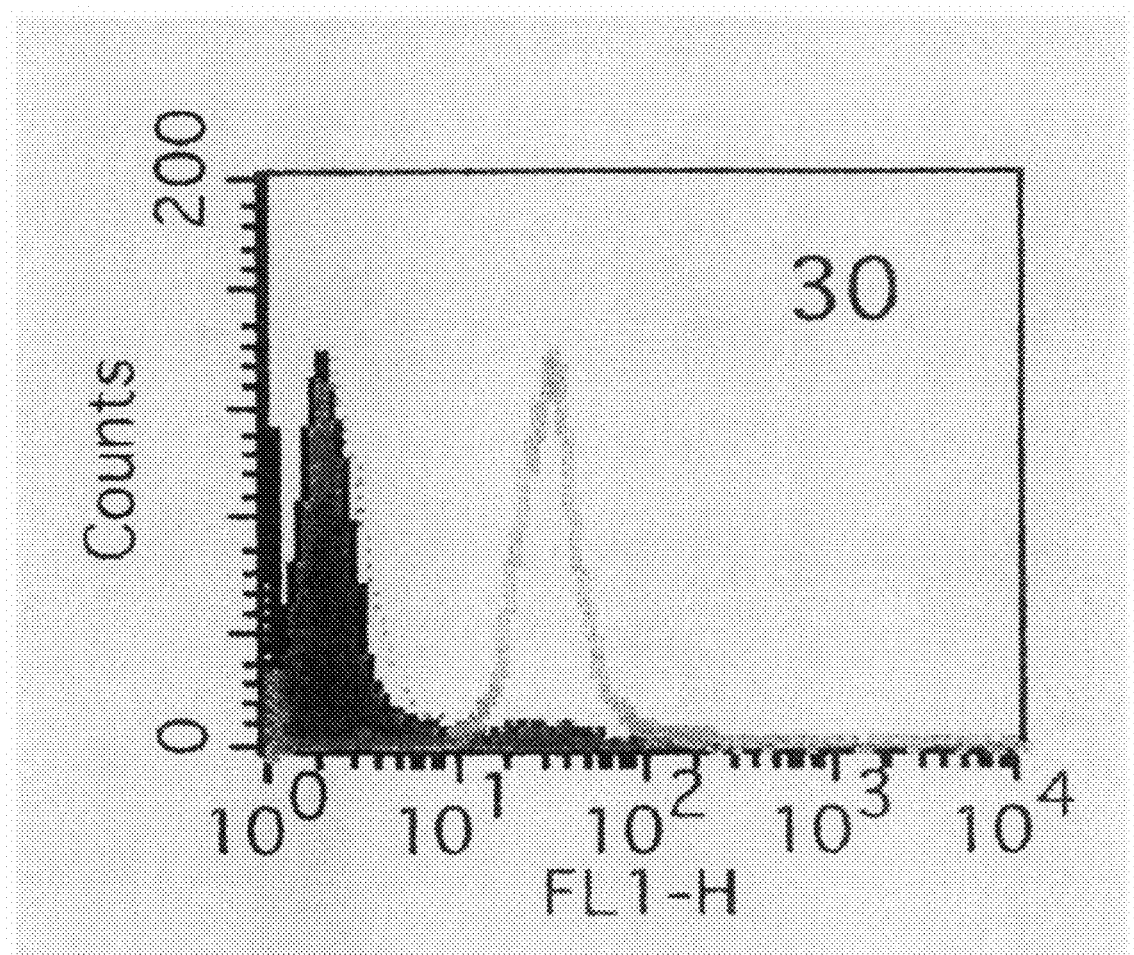
Figure 10J:
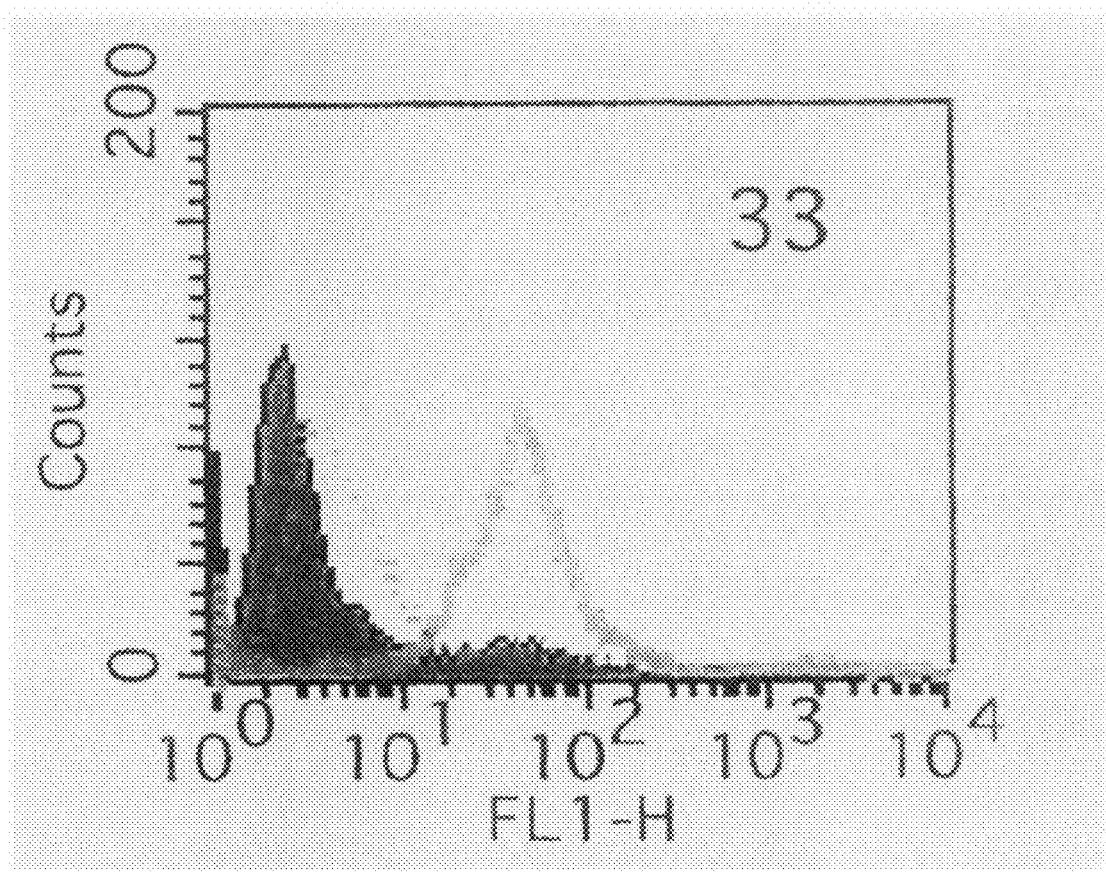
Figure 10K:
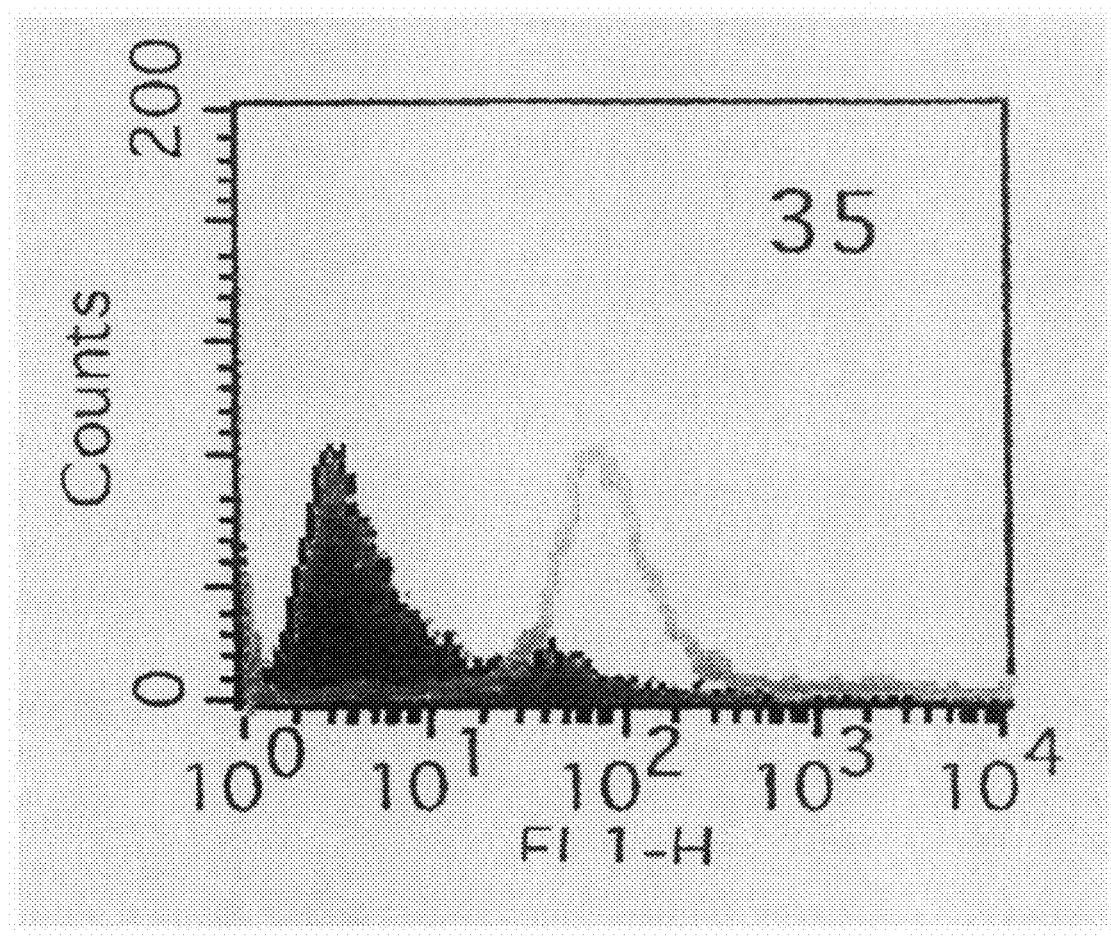
Figure 10L:
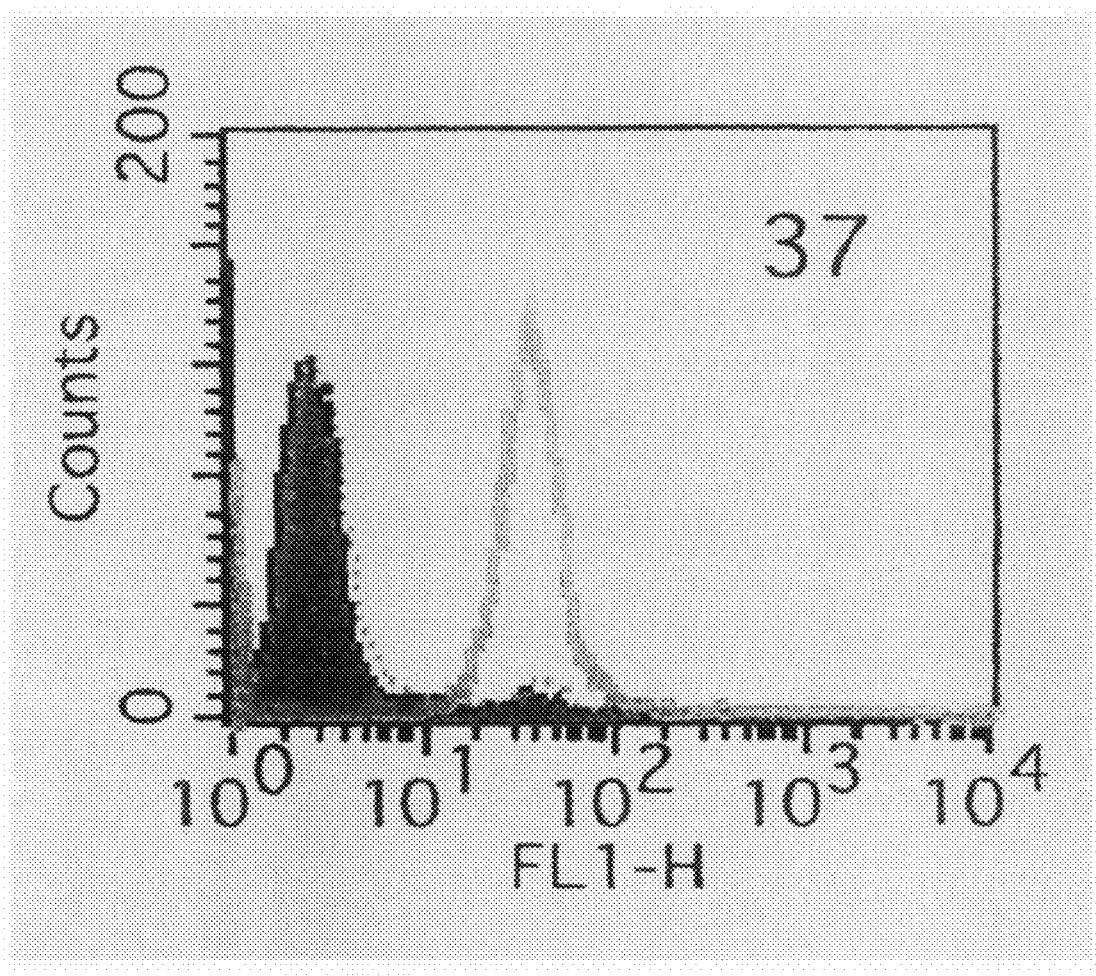
Figure 10M:
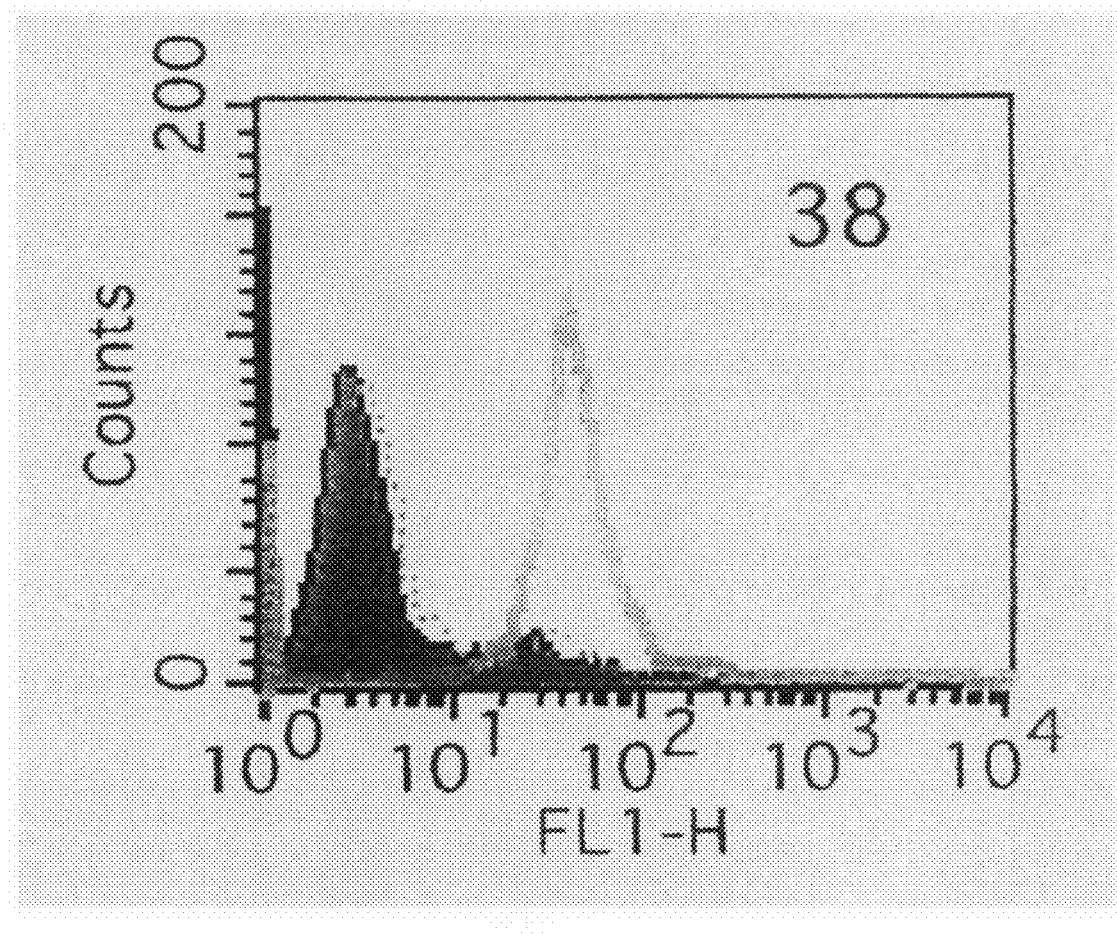

Another aspect of the present invention is a method for identifying an agent that binds to 2,6-sialic acid receptors. In one embodiment, an agent is provided to a ST6GAL 1-expressing cell, and it is determined whether the agent binds to the 2,6-sialic acid receptor. That is, it is possible to identify agents that bind to 2,6-sialic acid receptors, which may prove to be useful agents for blocking the binding of virus HA components to 2,6-sialic acid receptors thereby preventing or minimizing influenza virus infection of a human cell in vivo.

Another aspect of the present invention is a method for selecting a CHO cell susceptible to influenza virus, comprising (A) exposing a CHO cell to ICR191; (B) infecting the CHO cell with a virus which binds to 2,3-sialic acid receptors; (C) isolating and growing cells that survive virus infection; and (D) identifying the sialic acid receptor content on the surface of the surviving CHO cells, wherein a surviving CHO cell that contains elevated levels of 2,6-sialic acid receptors compared to a wild-type CHO cell is selected as a CHO cell that is susceptible to influenza virus that has 2,6-receptor specificity.

Another aspect of the present invention is a cell culture-based method for producing influenza virus, comprising (A) infecting a Chinese Hamster Ovary cell (CHO) with an influenza virus, wherein the CHO cell is transformed to (i) express an epidermal growth factor receptor gene, and (ii) has an increased cell surface expression of 2,6-linked sialic acids compared to an untransformed cell; and (B) isolating influenza viruses produced from the CHO cell.

BRIEF DESCRIPTION OF THE DRAWINGS

FIG. 1: Schematic of pcDNA3.1 ST6 plasmid

FIG. 2: Schematic of pCAGGSST6 plasmid

FIG. 3: Flow cytometry data on transfected CHO cells (a) pcDNA3.1. Reactivity of 2,6-specific sialic acid lectin with ST6Gal I-expressing (ST6 CHO) or wildtype (WT CHO) CHO cells. Cells were incubated with digoxigenin labeled *S. nigra* agglutinin (SNA), specific for 2,6-linked sialic acids followed by the anti-digoxigenin-fluorescein conjugated antibody, and then analyzed by flow cytometry. The mean fluorescence intensity of WT CHO indicates that WT CHO do not contain 2,6-linked sialic acids on the cell surface. ST6 CHO cells expressing the human ST6Gal 1 gene however contain increased levels of 2,6-linked sialic acids as shown by the curve shift to the right (increased mean fluorescence intensity).

FIG. 4 (A through E): Flow cytometry data on transfected MDCK cells. (a) pcDNA3.1; (b) pCAGGS (as described for FIG. 3).

FIG. 5 (A through E): Flow cytometry data on transfected Vero cells (a) pcDNA3.1; (b) pCAGGS (as described for FIG. 3).

FIG. 6 (A through C): Sorting of VeroST6 to obtain pure population of 2,6 sialic acid expressing cells. (a) VeroST6 transfectant relative to parent before sorting; (b) VeroST6 transfectant relative to parent after cell sorting; (c) overlay of pre-sort and post-sort relative to parent Vero to demonstrate enrichment of 2,6 expressing population (shift to right).

FIG. 7. Graph showing growth and increased viral titers over time (up to 96 hours post-infection) in wild type CHO cells and CHO cells engineered to express a 2,6-sialyltransferase gene.

FIG. 8. Titers of PR8 virus from t=72 hpi from wt CHO vs ST6 CHO determined on MDCK cells stained with crystal violet: Aliquots were taken from supernatants of infected CHO and ST6 CHO at time intervals ranging from t=24 hours post infection (hpi) to t=72 hpi and titers determined on MDCK cells. Representative timepoint t=72 hpi is shown. Plaques are seen on the crystal violet stained wells in 10-1 dilution for WT CHO whereas >35 plaques are present in the 10-3 dilution in ST6 CHO wells.

FIG. 9(A through D): Growth curve data for different influenza viruses that demonstrate that the inventive ST6 CHO cells support efficient influenza virus replication compared to growth curves generated from MDCK viral infections. ST66 CHO cells were exposed to (A) A/Nanching/933 (H3N2); (B) A/Texas/36/91 (H1N1); (C) B/Florida/4/2006; and (D) A/Puerto Rico/8/1934.

FIG. 10 (A through M): Flow data showing the relative intensities of 2,3-linked sialic acid expression and of 2,6-linked sialic acid expression in ICR 191-mutagenized CHO cells.

Figure 11:
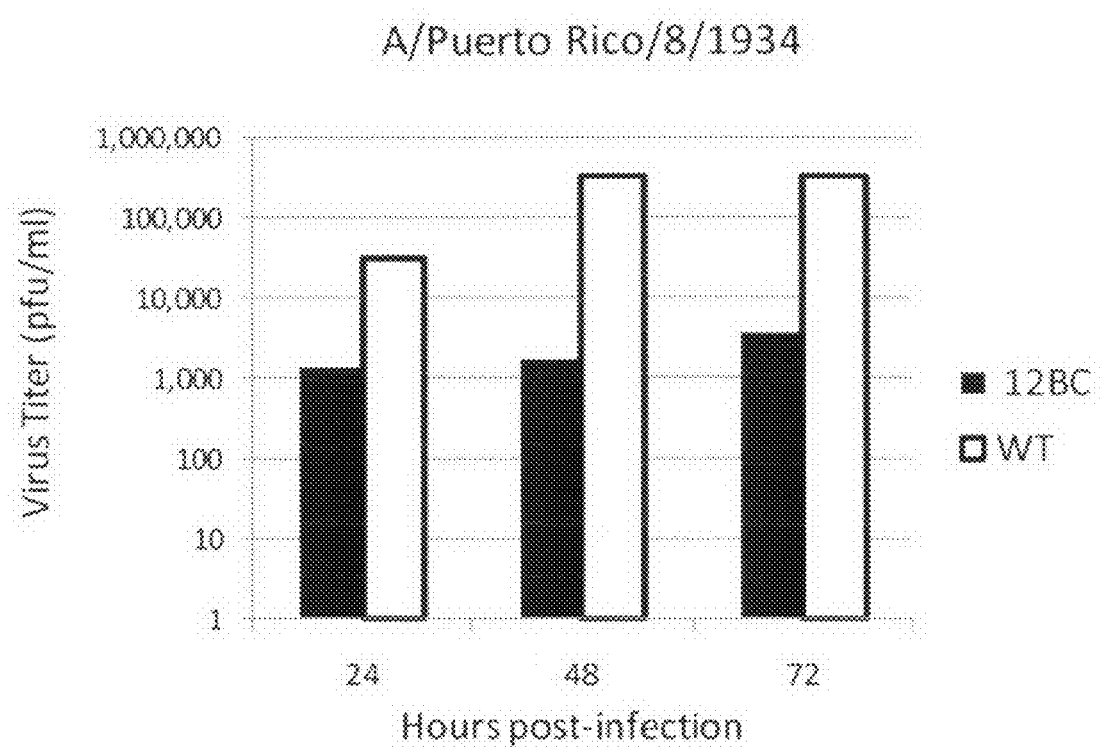

FIG. 11. Viral titers (pfu/ml) taken from 24 to 72 hours showing the yield of A/Puerto Rico/8/1934-infected mutagenized CHO cell clone 12BC.

Figure 12:
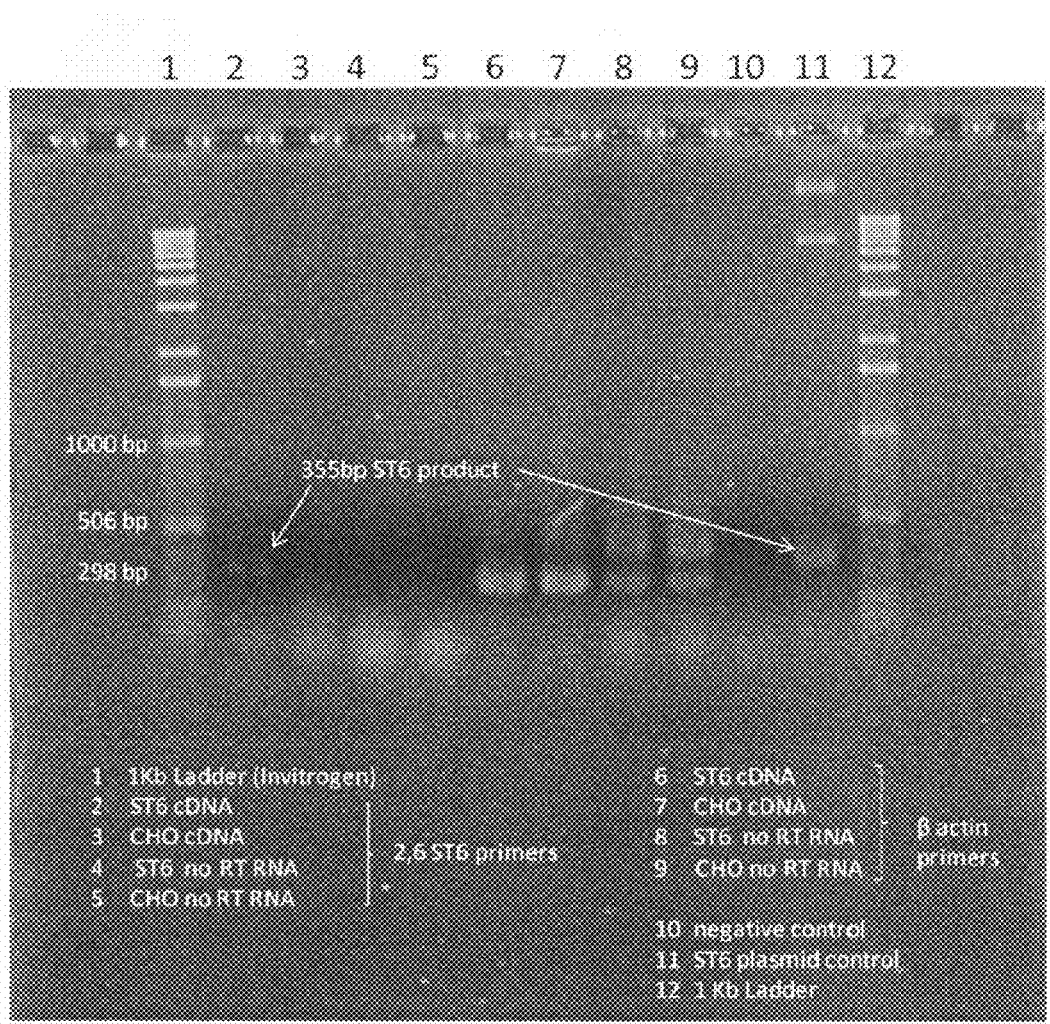

FIG. 12. Gel photograph of PCR analysis of RNA extracted from 2,6-transformed CHO cells confirming the expression of the 2,6-sialyltransferase gene in those transformants.

DETAILED DESCRIPTION

A novel aspect of the present invention is to exploit well-defined cell systems to generate increased influenza vaccine virus yields by increasing human-specific influenza receptors on the cell surface. This cell culture-based method for producing influenza vaccines avoids the delay, cost, low yield, tumorigenicity, and contamination risks that are inherent in existing egg-based vaccine manufacturing procedures and currently existing cell systems. The present invention reveals that 2,6-enriched CHO cells are excellent cells for manufacturing viruses. See Table 1 and also Example 1, which relate the increased influenza virus production in CHO cells that have been engineered to express a 2,6-sialyltransferase gene.

The present inventive methods and cells therefore exploit the way in which influenza viruses bind and infect cells. To explain, influenza viruses possess two surface spike proteins, hemagglutinin (HA) and neuraminidase (NA). The HA protein, a trimeric type I membrane protein, is responsible for binding to sialyloligosaccharides (oligosaccharides containing terminal sialic acid linked to galactose) on host cell surface glycoproteins or glycolipids. This protein is also responsible for fusion between viral and host cell membranes, following virion internalization by endocytosis.

Neuraminidase (NA), a tetrameric type II membrane protein, is a sialidase that cleaves terminal sialic acid residues from the glycoconjugates of host cells and the HA and NA, and thus is recognized as receptor-destroying enzyme. This sialidase activity is necessary for efficient release of progeny virions from the host cell surface, as well as prevention of progeny aggregation due to the binding activity of viral HAs with other glycoproteins. Thus, the receptor-binding activity of the HA and the receptor-destroying activity of the NA likely act as counterbalances, allowing efficient replication of influenza virus, e.g., influenza A virus. See U.S. Pat. No. 7,176,021, which is incorporated herein by reference.

Accordingly, influenza infection of mammalian cells is mediated by the hemagglutinin (HA) glycoprotein present on influenza virus binding to the sialic acid (SA) receptors on the target cell membrane. Human influenza viruses bind strongly to 2,6-linked sialic acids but do not bind to 2,3-linked sialic acids. The problem however is that Chinese Hamster Ovary (CHO) cells do not express the 2,6-linked sialic receptors on their cell surface.

By contrast, the present invention expressly entails the creation of a novel Chinese Hamster Ovary (CHO) cell which does express one or more copies of a 2,6-sialyltransferase gene, and which presents those receptors on the CHO cell membrane surface. This gene, although it does exist in the CHO cell genome, is not apparently transcriptionally expressed in CHO cells, which means the surface of the cell does not express the corresponding receptor, i.e., the α2,6-sialic acid receptor, to which influenza viruses bind. Thus, CHO cells synthesize oligosaccharides that are terminated in α2,3-linked sialic acid but lack β-galactoside α2,6-sialyltransferase. Hence, a lectin specifically recognizing α2,6-linked sialic acid does not bind to the cell surface or intracellular structures such as Golgi apparatus and lysosomes of CHO cells. See Margit Pavelka and Jürgen Roth, "Cell-Type-Related Differences in Oligosaccharide Structure" in FUNCTIONAL ULTRASTRUCTURE: AN ATLAS OF TISSUE BIOLOGY AND PATHOLOGY, XVI, 326 p. 157 illus. (2005) (ISBN: 978-3-211-83564-7); Monaco et al., "*Genetic engineering of* α2,6-*sialyltransferase in recombinant CHO cells and its effects on the sialylation of recombinant interferon*-γ," Cytotechnology 22:197-203 (1996), and Paulson, "*Alteration of Terminal Glycosylation Sequences on N-linked Oligosaccharides of Chinese Hamster Ovary cells by expression of* β-*galactoside* α2,6-*sialyltransferase*," J Biol Chem 264:13848-13855 (1989) which are all incorporated herein by reference.

Thus, by increasing the availability of α2,6-sialic acid receptors on the surface of CHO cells, the inventive method creates a new CHO cell line that is now amenable to efficient and predictable infection of CHO cells by human influenza virus. That is, the efficiency and specificity of viral infection is related to the number of sialic acid receptors available on the cell surface for viral attachment. Hence, once the influenza virus has "docked" with the CHO cell surface via HA/2,6-SA receptor binding, the virus is then engulfed by the cell membrane, and viral RNA molecules are released into the cell. Consequently, for the first time, CHO cells are now available as a cell culture-based method for manufacturing high yields of influenza viruses and particles thereof, which can be formulated into influenza vaccines.

I. The ST6GAL 1 Gene and 2,6-Sialic Acid Receptors

The present invention creates a genetically modified CHO cell which has been transformed so as to express at least one copy of a 2,6-sialyltransferase I (ST6Gal I) gene. ST6Gal I encodes an enzyme which catalyzes the α-2,6-sialylation of N-acetyllactosamine moieties of glycoproteins and glycolipids. This ultimately results in the presentation of α2,6-sialic acid receptors on the cell surface. Any 2,6-sialyltransferase I gene may be used and the present invention is not limited to the expression of any particular species or isoform or allele of 2,6-sialyltransferase I. The *Homo sapiens* ST6 beta-galatosamide alpha-2,6-sialyltransferase gene sequence denoted by the accession number BC040009.1, is an example of one type of ST6Gal gene that can be integrated into and expressed by a CHO cell according to the present invention.

According to the present invention, one or more copies of a polynucleotide that encodes a functional ST6Gal I gene product can be engineered into a cell of the present invention. That is, the present invention provides cells which have been stably transformed to express 1, 2, 3, 4, 5, 6, 7, 8, 9, 10, 11, 12, or more than 12 copies of a ST6Gal I gene. A single expression cassette may include one or more copies of the ST6Gal I gene to be expressed, which is operably linked to regulatory elements, such as promoters, enhancers, and terminator and polyadenylation signal sequences, to facilitate the expression of the ST6Gal I gene or its copies. Alternatively, a single expression cassette may be engineered to express one copy of an ST6Gal I gene, and multiple expression cassettes integrated into a host cell genome. Accordingly, the present invention provides for the integration of at least one ST6Gal I gene into the genome of a host cell, such that the cell expresses the ST6Gal I gene and its enzymatic protein product. Depending on the copy number, a single host cell may express many functional ST6Gal I gene proteins.

Suitable vectors for cloning and transfecting and producing stable cell lines include the pcDNA3.1 vectors (Invitrogen). Example 10 and FIG. 12 concern PCR amplification experiments that were performed on CHO cells transformed with the ST6Gal I gene corroborating the presence of 2,6-sialyltransferase gene RNA that corresponds to the presence of 2,6-receptors on the surface of the CHO cell membrane as evidenced by the Flow Data provided herein.

The present invention is not limited to the expression of only the ST6Gal I gene and its corresponding 2,6-sialic acid receptors on the surface of CHO cells. Any protein, polypeptide, glycoprotein, or any such receptor, to which an influenza virus may bind can be expressed and presented on the surface of a CHO cell; and expressed in a CHO cell that does not normally express that receptor or its encoding polynucleotide. For instance, an aspect of the present invention is the expression of a gene that encodes a cell surface receptor which is recognized by the influenza hemagglutinin and which therefore effectively acts as a docking locus like the 2,6-sialic acid receptor, enabling the influenza virus to bind to the CHO cell. Thus, along these lines, there is evidence that signal transmitting receptors may also play a role in viral uptake. It has been shown, for instance, that epidermal growth factor receptor (EGFR) contributes to efficient entry of influenza A viruses into cells (Cell Communication and Signaling 2009, 7 (1):A14; Cell Microbiol 2006, 8(8):1336-1367). EGFR is not expressed in CHO cells (J. Cell Biol. 2000, 148: 591-601) and therefore overexpression of EGFR by generating stably transfected ST6 CHO cells may result in increased viral yields, as shown herein as evidenced by the increased viral yields obtained for CHO cells transformed with the ST6Gal I gene.

II. Host Cells and Cell Lines

The present invention provides a safer, cheaper, faster, and greater yielding, cell-based production system for making influenza vaccines. One aspect of the present invention is therefore based on a permanent diploid and non-tumorigenic cell line, such as CHO. A cell line of the present invention therefore can be made from, for instance a CHO cell that has been engineered to express at least one copy of the ST6Gal I gene. Methods for creating stable immortalized cell lines are well known. See for instance the protocol provided in the manufacturer's instructions (Invitrogen) for the pcDNA3.1 cloning and transfection system, which are essentially based on successive selection of cells that survive and grow on antibiotic medium.

Such a cell line can be identified that generates high titers of influenza virus and used to initiate a master cell bank (MCB), which can then be formally qualified as meeting certain criteria established by the U.S. Food and Drug Administration (FDA), the International Conference on Harmonization, and the World Health Organization (WHO), for producing vaccines for administration to humans. Testing of the MCB for adventitious agents is a critical step in developing a qualified source of cells for producing a vaccine for human use. After successful validation of the MCB, a cell line of the present invention can be scaled-up to establish maintenance of the increased yields at a commercially viable scale. Furthermore, the qualified MCB can be used to produce, for instance, live attenuated vaccine candidates for both pandemic and seasonal influenza.

The Chinese Hamster Ovary (CHO) cell line is the most widely used mammalian cell line for manufacture of biopharmaceuticals. It is used to produce about 70 percent of all pharmaceutically important recombinant DNA proteins. See Jayapal et al., "Recombinant Protein therapeutics from CHO cells-20 Years and Counting," Chemical Engineering Progress (October 2007), which is incorporated herein by reference. Indeed, over two thirds of all recombinant protein therapeutics produced today are generated using CHO cells, and over $30 billion can be attributed to the sales of biologics produced with these well-characterized cells. CHO cells are very well received by regulatory authorities worldwide and have over 20 years of manufacturing history. Thus, CHO cells have been used for two decades in studies of genetics, toxicity screening, nutrition and gene expression; particularly expression of recombinant proteins including tissue plasminogen activator, erythropoietin, and monoclonal antibodies. See Lee et al., "Alteration of terminal glycosylation sequences on N-linked oligosaccharides of Chinese Hamster Ovary cells by expression of β-Galactoside α2,6-sialyltransferase," J. Biol. Chem., 264:13848-13855 (1989); Wiebe et al., "A multifaceted approach to assure that recombinant tPA is free of adventitious virus In: Advances in animal cell biology and technology," Butterworth-Heinemann, London, pp. 68-71 (1989); and Fukuta et al., "Genetic engineering of CHO cells producing human interferon-γ by transfection of sialyltransferases," Glyco Jour 17:895-904 (2000), which are all incorporated herein by reference.

As a host for expression of recombinant proteins, CHO cells have become the mammalian equivalent of bacterial expression systems in current research and biotechnology, primarily because of their stability of gene expression and because they are extremely adaptable and can grow to high densities in suspension cultures that are readily scalable. Any CHO cell may be used and transformed according to the present invention so as to be a manufacturing tool for producing influenza viral particles useful for preparing vaccines, such as those CHO cells that are commercially available. Such commercially available CHO cells which can be used according to the present invention include, but are not limited to, those available from Invitrogen (CHO-S), the ATCC (CHO-K1 (CCL-61) and related derivatives or mutants), and the ECACC (CHO and related derivatives or mutants).

Figure 7:
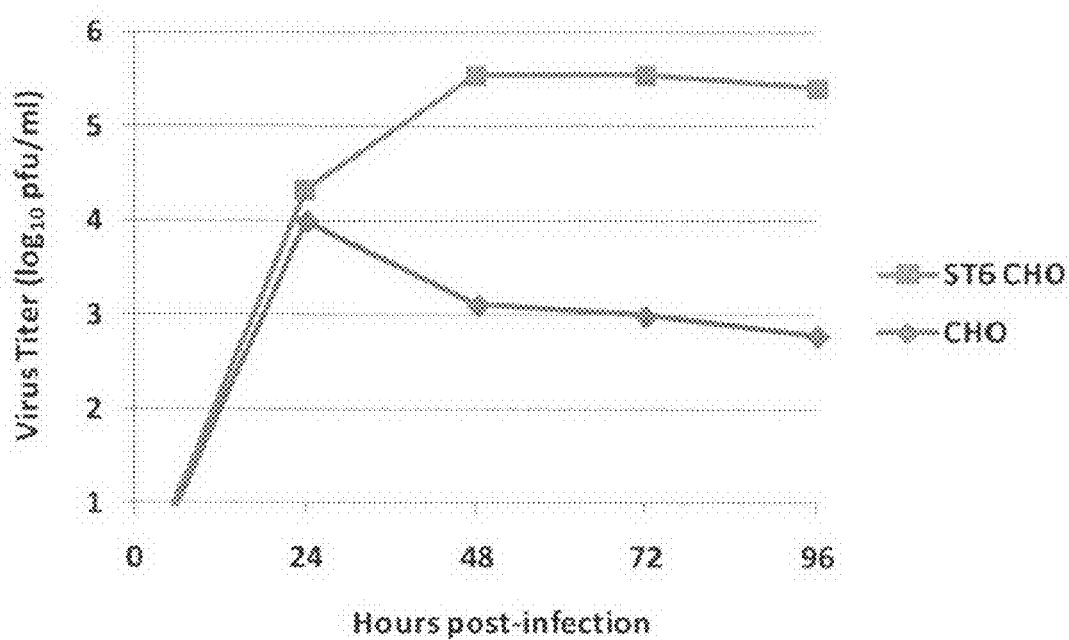

CHO cells have various advantageous industrial characteristics, such as proliferation in bioreactors as high cell density suspension cultures, growth in serum-free media (SFM), absence of in vivo tumorigenicity, and government regulatory acceptance. With respect to the latter two points, CHO cells have a proven track record for producing proteins and biologics that are safe and bioactive in humans. One of the early concerns in recombinant protein production was that cultured mammalian cells were presumably derived through perturbation of oncogenes, and thus, could proliferate without the effects of senescence. However, CHO cells have since been proven safe, with the value of products being generated from them considerably outweighing any associated risks. Furthermore, downstream processes for CHO cell products have matured to a stage where they can be purified to contain sub-picogram levels of contaminating CHO DNA per dose of the product (Jayapal (2007) supra). It is related herein that CHO cells that have been transformed to express the human ST6Gal 1 gene display an increased level of 2,6-linked sialic acids. See FIG. 4 and Example 2, particularly section D. CHO cells of the present invention may therefore be referred to herein as "2,6-enriched cells," or "cells expressing an α2,6-sialyltransferase gene," or "2,6-CHO cells" or "ST6GAL-CHO cells" or "recombinant CHO cells" or "cells expressing 2,6-sialic acid receptors," etc. It also is related herein that these 2,6-enriched CHO cells are excellent cells for manufacturing viruses. See Table 1 and Table 2 which report the increased virus production in ST6Gal I expressing CHO cells that had been infected with A/PR/8134 influenza virus. See also Example 1 and FIG. 7, which show the boost in viral titers in the inventive ST6 CHO cells.

Along these lines, disposable bioreactor systems have been developed for mammalian cells whose benefits include faster facility setup and reduced risk of cross-contamination. The ST6 CHO cells of the present invention, for instance, can be grown up in disposable bags such as those from Stedim, Bioeaze bags from SAFC Biosciences, HybridBag™ from Cellexus Biosytems, or single use bioreactors from HyClone or Celltainer from Lonza. Bioreactors can be 1 L, 10 L, 50 L, 250 L, 1000 L size formats. The cells are maintained in suspension in optimized serum free medium, free of animal products. The system can be a fed-batch system where a culture can be expanded in a single bag from 1 L to 10 L for example, or a perfusion system that allows for the constant supply of nutrients while simultaneously avoiding the accumulation of potentially toxic by-products in the culture medium. See also Example 8 below.

Also presented here are the results of experiments that relate growth curves for the different influenza viruses, which demonstrate that ST6 CHO cells support efficient influenza virus replication. See FIG. 9 (A-D). ST6 CHO cells were exposed to four different influenza viruses: (1) A/Nanching/933 (H3N2) (FIG. 9A); (2) A/Texas/36/91 (H1N1) (FIG. 9B); (3) B/Florida/4/2006 (FIG. 9C); and (4) A/Puerto Rico/8/1934 (FIG. 9D). These results suggest that the present CHO cells that overexpress the α-2,6 sialyltransferase gene are extremely useful for producing vaccines against influenza. The present CHO-cell based influenza vaccine production system is therefore ideally suited to readily producing large quantities of vaccines in the event of pandemics or rampant infectious influenza activity in local and global communities. Thus, the present inventive cells are very useful for preparing vaccines against the so-called "swine flu" virus (H1N1sw) that has been circulating in humans in 2009. The present inventive CHO cell production method permits seed virus for the H1N1sw vaccine to be derived directly from clinical specimens, clinical isolates or from reassortants provided by the CDC, to rapidly produce H1N1sw-specific vaccines. See Example 9 below.

Thus, a benefit of the present 2,6-enriched CHO cells for producing influenza viruses is evident in the culturing of clinical isolates of virus specimens from human individuals. That is, a clinical swab or biological sample taken from a human may contain a low number of influenza viral particles, but because the CHO cell surface is enriched for 2,6-sialic acid receptors, there is more opportunity and chance for those few viral particles to infect and replicate in culture. Hence, the enriched 2,6-CHO cells are sensitive tools for ensuring satisfactory culture growth of specimen viruses.

Furthermore, the 2,6-enriched CHO cells are suitable for preparing seed viruses, which eliminates the need to use egg-adapted viruses that necessarily have to adapt from their "normal" infectious state in order to replicate and survive in the egg fluid during conventional virus vaccine manufacturing protocols.

The present invention is not limited to the expression of 2,6-sialyltransferase genes only in CHO cells, however; any mammalian cell can be transformed with any construct to express one or more 2,6-sialyltransferase genes. Any cell type can be transfected so as to express or overexpress a 2,6-sialyltransferase gene and can be selected based on considerations of various features, such as cell availability, ease of culturing, doubling time, acceptability to biopharmaceutical manufacturers and regulatory status related to human use. The concentration of 2,6-linked sialic acids in continuous cell lines that are currently used for influenza virus propagation, such as MDCK and VERO cells, is relatively low and growth of clinical influenza virus isolates in cell lines has historically been difficult. See Hatakeyama et al., "Enhanced expression of an α2,6-linked sialic acid on MDCK cells improves isolation of human influenza viruses and evaluation of their sensitivity to a neuraminidase inhibitor," J. Clin. Micro. 43:4139-4146 (2005), which is incorporated herein by reference.

Vero cells (African green monkey kidney cells), for example, have been widely used in vaccine manufacturing (i.e., to produce inactivated and oral poliovirus vaccine, and inactivated rabies vaccine) and are sensitive to infection with a large range of viruses, including influenza viruses. However, several studies indicate that influenza viruses do not replicate productively in Vero cells. See Govorkova et al., "African green monkey (Vero) cells provide an alternative host cell system for influenza A and B viruses," J. Virol. 70:5519-5524 (1996); Lau and Scholtissek, "Abortive infection of Vero cells by an influenza A virus (FPV)," Virology 212:225-231 (1995); and Nakamura and Homma, "Protein synthesis in Vero cells abortively infected with influenza B virus," J. Gen. Virol 56:199-202 (1981), which are incorporated herein by reference. This may in part be due to the fact that Vero cells, like CHO cells, do not contain sufficient receptors for human influenza viruses. Vero cells primarily contain 2,3 linked sialic acid receptors on their cell surface in contrast to MDCK cells which contain both 2,3- and 2,6-linked influenza receptors. See Matrosovich et al., "Overexpression of the α-2,6-sialyltransferase in MDCK cells increases influenza virus sensitivity to neuraminidase inhibitors," J. Virol. 77:8418-8425 (2003); and Russell et al., "Avian and human receptor binding by hemagglutinins of influenza A viruses," Glycoconj. J., 23:85-92 (2006), which are incorporated herein by reference. However, neither the MDCK or Vero cell lines contain 2,6-linked receptors in the quantities that are present in human airway epithelial cells (the target cell population for influenza infection). Although Vero cells grow indefinitely in culture, they do not form tumors in immunosuppressed rodents at the passage levels used for vaccine manufacture. Therefore, Vero cells are considered safe for vaccine production. See Lubiniecki A S, Cytotechnology, 1998—Historical Reflections on cell culture engineering 28: 139-145; and Kistner et al., "Development of a Vero cell-derived influenza whole virus vaccine," Dev Biol Stand 98:101-110 (1999), which are incorporated herein by reference. Accordingly, both Vero cells and MDCK cells can be engineered according to the present invention to express a ST6Gal I gene.

The present invention also provides other ways in which to obtain 2,6-sialic acid receptor-enriched CHO cells. For instance, another way to create a 2,6-enriched CHO cell is to add transcription protein factors or express regulatory genes in the CHO cell, or activate the α2,6-sialyltransferase gene promoter, in order to target and thereby increase the expression of the endogenous α2,6-sialyltransferase gene, which is normally transcriptionally-silent.

Another way the present invention encompasses for obtaining 2,6-sialic acid receptor-enriched CHO cells is to expose wild type CHO cells to an infectious 2,3-recognizing virus, such as avian virus, and then select those CHO cells that survive, which can then be cultured and the identity of the surviving cells' surface membrane receptor constituents determined, such as by flow cytometry. The implication is that those CHO cells that survive exposure to a 2,3-infecting virus, have fewer or abnormal or mutated 2,3-sialic acid receptors to which the 2,3-recognizing (e.g., avian) virus would have otherwise bound. Accordingly, investigation of the surviving cells could reveal a CHO cell in which the transcriptional regulation of the genomic α2,6-sialyltransferase is increased or activated compared to the wild type CHO cell transcriptional machinery. Thus, a surviving cell could express fewer 2,3 receptors but more than normal 2,6-sialic acid receptors because of the transcription and translation of the α2,6-sialyltransferase gene and corresponding RNA transcript in that cell.

Another way to identify CHO cells that have an enriched membrane surface for 2,6-sialic acid receptors, or which detectably express an α2,6-sialyltransferase gene, is to mutagenize a wild type CHO cell. For example, CHO cells can be mutagenized with some wave-source, e.g., X-rays or U.V., or chemical, or substance, e.g., ICR 191 (an acridine half-mustard that causes frameshifts) (see Example 6), prior to infection with a 2,3-recognizing virus, such as an avian virus that binds 2,3-sialic acid receptors. The cells that survive can be isolated and cultured, and the sialic acid linkages on the surviving, mutagenized CHO cells were evaluated by flow cytometry. See Example 6. Indeed the experiments presented here in Examples 6 and 7 demonstrate the identification and selection of ICR 191 mutagenized CHO cells that survive exposure to 2,3-recognizing virus, A/Mallard/New York/1978, and which have enriched 2,6-receptors on their surface (see Flow data in FIG. 10). One of those mutagenized clones, 12BC, was exposed to A/Puerto Rico/8/34 (H1N1) and subsequently shown to effectively replicate and produce virus particles. See Example 7. Clone 12BC does not have any detectable 2,3 sialic acid receptors on the cell surface, which resulted in viral titers less than the WT for viruses such as PR8 that use both 2,3 and 2,6 sialic acid receptors. These results suggest that CHO cells that express the α2,6 sialyltransferase exclusively, such as clone 12BC, are very useful for propagating primary clinical influenza isolates that can then be used as virus seed in the production of vaccines.

III. Vaccines

There are various different types of "vaccines" which can be made from the cell-based virus production system disclosed herein. The present invention includes, but is not limited to, the manufacture of live attenuated virus vaccines, inactivated virus vaccines, whole virus vaccines, split virus vaccines, virosomal virus vaccines, and viral surface antigen vaccines. Thus, there are numerous vaccines capable of producing a protective immune response specific for different influenza viruses where appropriate formulations of any of these vaccine types are capable of producing a systemic immune response. Live attenuated virus vaccines have the advantage of being also able to stimulate local mucosal immunity in the respiratory tract. More details on different types of vaccines that can be made from the influenza viruses produced from the inventive ST6Gal I-expressing cells follow below. See also U.S. Pat. No. 7,176,021, which is incorporated herein by reference.

Vaccine antigens used in the pharmaceutical compositions according to the present invention are "direct" antigens, i.e. there are not DNA encoding these antigens, but the antigens themselves; they may be a whole virus or only part of this virus, such as but not limited to viral polysaccharides, whether they are alone or conjugated to carrier elements, such as carrier proteins, live attenuated whole microorganisms, inactivated microorganisms, recombinant peptides and proteins, glycoproteins, glycolipids, lipopeptides, synthetic peptides, or ruptured microorganisms in the case of vaccines referred to as "split" vaccines.

A vaccine of the present invention may be administered via all the routes conventionally used or recommended for vaccines: parenteral route, mucosal route, and may be in various forms: injectable or sprayable liquid, formulation which has been freeze-dried or dried by atomization or air-dried, etc. It may be administered by means of a syringe or by means of a needle-free injector for intramuscular, subcutaneous or intradermal injection. It may also be administered by means of a nebulizer capable of delivering a dry powder or a liquid spray to the mucous membranes, whether they are nasal, pulmonary, vaginal or rectal.

A complete virion vaccine can be concentrated by ultrafiltration and then purified by zonal centrifugation or by chromatography. It is inactivated before or after purification using formalin or beta-propiolactone, for instance.

A subunit vaccine comprises purified glycoproteins. Such a vaccine may be prepared as follows: using viral suspensions fragmented by treatment with detergent, the surface antigens are purified, by ultracentrifugation for example. The subunit vaccines thus contain mainly HA protein, and also NA. The detergent used may be cationic detergent for example, such as hexadecyl trimethyl ammonium bromide, an anionic detergent such as ammonium deoxycholate; or a nonionic detergent such as that commercialized under the name TRITON X100. The hemagglutinin may also be isolated after treatment of the virions with a protease such as bromelin, then purified by standard methods.

A split vaccine comprises virions which have been subjected to treatment with agents that dissolve lipids. A split vaccine can be prepared as follows: an aqueous suspension of the purified virus obtained as above, inactivated or not, is treated, under stirring, by lipid solvents such as ethyl ether or chloroform, associated with detergents. The dissolution of the viral envelope lipids results in fragmentation of the viral particles. The aqueous phase is recuperated containing the split vaccine, constituted mainly of hemagglutinin and neuraminidase with their original lipid environment removed, and the core or its degradation products. Then the residual infectious particles are inactivated if this has not already been done.

Inactivated influenza virus vaccines are made by inactivating the virus using known methods, such as, but not limited to, formalin or β-propiolactone treatment. Inactivated vaccine types that can be used in the invention can include whole-virus (WV) vaccines or subvirion (SV) (split) vaccines. The WV vaccine contains intact, inactivated virus, while the SV vaccine contains purified virus disrupted with detergents that solubilize the lipid-containing viral envelope, followed by chemical inactivation of residual virus.

Live attenuated influenza virus vaccines, using the adapted virus of the invention, can also be used for preventing or treating influenza virus infection, according to known method steps. Attenuation is preferably achieved in a single step by transfer of attenuated genes from an attenuated donor virus to an isolate or reassorted virus according to known methods (see, e.g., Murphy, Infect. Dis. Clin. Pract. 2, 174 (1993)).

The virus can thus be attenuated or inactivated, formulated and administered, according to known methods, as a vaccine to induce an immune response in an animal, e.g., a mammal.

Methods are well-known in the art for determining whether such attenuated or inactivated vaccines have maintained similar antigenicity to that of the clinical isolate or a high growth strain derived therefrom. Such known methods include the use of antisera or antibodies to eliminate viruses expressing antigenic determinants of the donor virus; chemical selection (e.g., amantadine or rimantidine); HA and NA activity and inhibition; and DNA screening (such as probe hybridization or PCR) to confirm that donor genes encoding the antigenic determinants (e.g., HA or NA genes) are not present in the attenuated viruses. See, e.g., Robertson et al., Giornale di Igiene e Medicina Preventiva, 29, 4 (1988); Kilbourne, Bull. M2 World Health Org., 41, 643 (1969); and Robertson et al., Biologicals, 20, 213 (1992).

IV. Pharmaceutical Compositions

Pharmaceutical compositions of the present invention, suitable for inoculation or for parenteral or oral administration, comprise attenuated or inactivated influenza viruses, optionally further comprising sterile aqueous or non-aqueous solutions, suspensions, and emulsions. The compositions can further comprise auxiliary agents or excipients, as known in the art. See, e.g., Berkow et al., The Merck Manual, 15.sup.th edition, Merck and Co., Rahway, N.J. (1987); Goodman et al., eds., Goodman and Gilman's The Pharmacological Basis of Therapeutics, 8.sup.th edition, Pergamon Press, Inc., Elmsford, N.Y. (1990); Avery's Drug Treatment: Principles and Practice of Clinical Pharmacology and Therapeutics, 3.sup.rd edition, ADIS Press, LTD., Williams and Wilkins, Baltimore, Md. (1987); and Katzung, ed., Basic and Clinical Pharmacology, Fifth Edition, Appleton and Lange, Norwalk, Conn. (1992).

Conventional vaccines generally contain about 0.1 to 200 .mu.g, preferably 10 to 15 .mu.g, of hemagglutinin from each of the strains entering into their composition. The vaccine forming the main constituent of the vaccine composition of the invention may comprise a virus of type A, B or C, or any combination thereof, for example, at least two of the three types, at least two of different subtypes, at least two of the same type, at least two of the same subtype, or a different isolate(s) or reassortant(s). Human influenza virus type A includes H1N1, H2N2 and H3N2 subtypes.

Preparations for parenteral administration include sterile aqueous or non-aqueous solutions, suspensions, and/or emulsions, which may contain auxiliary agents or excipients known in the art. Examples of non-aqueous solvents are propylene glycol, polyethylene glycol, vegetable oils such as olive oil, and injectable organic esters such as ethyl oleate. Carriers or occlusive dressings can be used to increase skin permeability and enhance antigen absorption. Liquid dosage forms for oral administration may generally comprise a liposome solution containing the liquid dosage form. Suitable forms for suspending liposomes include emulsions, suspensions, solutions, syrups, and elixirs containing inert diluents commonly used in the art, such as purified water. Besides the inert diluents, such compositions can also include adjuvants, wetting agents, emulsifying and suspending agents, or sweetening, flavoring, or perfuming agents.

When a composition of the present invention is used for administration to an individual, it can further comprise salts, buffers, adjuvants, or other substances which are desirable for improving the efficacy of the composition. For vaccines, adjuvants, substances that augment a specific immune response, can be used. Normally, the adjuvant and the composition are mixed prior to presentation to the immune system, or presented separately, but into the same site of the organism being immunized.

Heterogeneity in a vaccine may be provided by mixing replicated influenza viruses for at least two influenza virus strains, such as from 2-50 strains, or any range or value therein. Influenza A or B virus strains having a modern antigenic composition are preferred. According to the present invention, vaccines can be provided for variations in a single strain of an influenza virus, using techniques known in the art.

A pharmaceutical composition according to the present invention may further or additionally comprise at least one chemotherapeutic compound, e.g., for gene therapy, an immunosuppressant, an anti-inflammatory agent or an immunostimulatory agent, or anti-viral agents including, but not limited to, gamma globulin, amantadine, guanidine, hydroxybenzimidazole, interferon-.alpha., interferon-.beta., interferon-.gamma., tumor necrosis factor-.alpha., thiosemicarbarzones, methisazone, rifampin, ribavirin, a pyrimidine analog, a purine analog, foscarnet, phosphonoacetic acid, acyclovir, dideoxynucleosides, a protease inhibitor, or ganciclovir. See, e.g., Katzung (1992) (supra), and the references cited therein on pages 798 800 and 680 681, respectively.

The composition can also contain variable but small quantities of endotoxin-free formaldehyde, and preservatives, which have been found safe and not contributing to undesirable effects in the organism to which the composition of the invention is administered.

V. Pharmaceutical Uses

The administration of the composition (or the antisera that it elicits) may be for either a prophylactic or therapeutic purpose. When provided prophylactically, the compositions of the invention which are vaccines are provided before any symptom of influenza viral infection becomes manifest. The prophylactic administration of the composition serves to prevent or attenuate any subsequent infection. When provided therapeutically, the attenuated or inactivated viral vaccine is provided upon the detection of a symptom of actual infection. The therapeutic administration of the compound(s) serves to attenuate any actual infection. See, e.g., Berkow et al., 1992; Goodman et al., 1990; Avery, 1987; and Katzung, 1992. An attenuated or inactivated vaccine composition of the present invention may thus be provided either before the onset of infection (so as to prevent or attenuate an anticipated infection) or after the initiation of an actual infection.

Similarly, for gene therapy, the composition comprising an adapted virus comprising a therapeutic gene may be provided before any symptom of a disorder or disease is manifested, or after one or more symptoms are detected.

A composition is said to be "pharmacologically acceptable" if its administration can be tolerated by a recipient patient. Such an agent is said to be administered in a "therapeutically effective amount" if the amount administered is physiologically significant. A composition of the present invention is physiologically significant if its presence results in a detectable change in the physiology of a recipient patient, for instance, for a vaccine, the administration of the composition to an organism that enhances at least one primary or secondary humoral or cellular immune response of that organism against at least one strain of an infectious influenza virus. The "protection" provided need not be absolute, e.g., the influenza infection need not be totally prevented or eradicated, if there is a statistically significant improvement compared with a control population or set of patients. Protection may be limited to mitigating the severity or rapidity of onset of symptoms of the influenza virus infection.

VI. Administration

A vaccine of the present invention may confer resistance to one or more influenza strains by either passive immunization or active immunization. In active immunization, an inactivated or attenuated live vaccine composition is administered prophylactically to a host (e.g., a mammal), and the host's immune response to the administration protects against infection and/or disease. For passive immunization, the elicited antisera can be recovered and administered to a recipient suspected of having an infection caused by at least one influenza virus strain.

The present invention thus includes methods for preventing or attenuating a disease or disorder, e.g., infection by at least one influenza virus strain. As used herein, a vaccine is said to prevent or attenuate a disease if its administration results either in the total or partial attenuation (i.e., suppression) of a symptom or condition of the disease, or in the total or partial immunity of the individual to the disease.

At least one inactivated or attenuated influenza virus, or composition thereof, of the present invention may be administered by any means that achieve the intended purposes, using a pharmaceutical composition as previously described. For example, administration of such a composition may be by various parenteral routes such as subcutaneous, intravenous, intradermal, intramuscular, intraperitoneal, intranasal, oral or transdermal routes. Parenteral administration can be by bolus injection or by gradual perfusion over time. A preferred mode of using a pharmaceutical composition of the present invention is by intramuscular or subcutaneous application. See, e.g., Berkow et al., 1992; Goodman et al., 1990; Avery, 1987; and Katzung, 1992.

A typical regimen for preventing, suppressing, or treating an influenza virus related pathology, comprises administration of an effective amount of a vaccine composition as described herein, administered as a single treatment, or repeated as enhancing or booster dosages, over a period up to and including between one week and about 24 months, or any range or value therein.

According to the present invention, an "effective amount" of a vaccine composition is one that is sufficient to achieve a desired biological effect. It is understood that the effective dosage will be dependent upon the age, sex, health, and weight of the recipient, kind of concurrent treatment, if any, frequency of treatment, and the nature of the effect wanted. The ranges of effective doses provided below are not intended to limit the invention and represent preferred dose ranges. However, the most preferred dosage will be tailored to the individual subject, as is understood and determinable by one of skill in the art. The dosage of an attenuated virus vaccine for a mammalian (e.g., human) or avian adult can be from about $10^3$-$10^7$ plaque forming units (PFU)/kg, or any range or value therein. The dose of inactivated vaccine can range from about 0.1 to 200, e.g., 50 .mu.g of hemagglutinin protein. However, the dosage should be a safe and effective amount as determined by conventional methods, using existing vaccines as a starting point.

EXAMPLES

Example 1

ST6 CHO Cells with Increased Levels of 2,6-Linked Sialic Acids and which Produce Increased Yields of Influenza Virus CHO cells were incubated with digoxigenin labeled *S. nigra* agglutinin (SNA), specific for 2,6-linked sialic acids followed by the anti-digoxigenin-fluorescein conjugated antibody, and then analyzed by flow cytometry. The mean fluorescence intensity of WT CHO indicates that WT CHO do not contain 2,6-linked sialic acids on the cell surface. ST6 CHO cells expressing the human ST6Gal 1 gene however contain increased levels of 2,6-linked sialic acids as shown by the curve shift to the right (increased mean fluorescence intensity). See FIG. 4.

Next, TC-24 cells were seeded with $2\times10^5$ CHO or ST6CHO cells. The confluent CHO or ST6CHO monolayers were infected with A/PR/8134 influenza virus at an MOI=1 the following day. Aliquots were taken out at 48 hours post infection and stored at $-80°$ C. Viral titers were determined on MDCK cells by plaque assay. Briefly, TC-6 culture plates were seeded with $1\times106$ MDCK cells. The next day the confluent monolayers were washed with PBS two times followed by infection with dilutions of the virus aliquot from CHO or ST6CHO cells. Unadsorbed virus was removed and a standard overlay containing 1×EMEM and 0.9% agar with 1 μg/ml trypsin/TPCK was added. After two days incubation at 37° C. in 5% $CO_2$, the plaques were stained with crystal violet.

The ST6Gal I expressing CHO cells produced a virus yield of $3.1\times10^3$ pfu/ml of virus particles. A/PR/8134 influenza virus recognizes 2,3-sialic acid receptors as well as 2,6-sialic acid receptors. Thus, the data presented herein in Table 1 also shows viral particle production in wild type CHO cells with a yield of $1.2\times10^3$ pfu/ml of virus particles. However, the ratio of virus yield reveals that the ST6Gal I expressing CHO cells of the present invention yielded more than double (2.6-fold) the amount of virus particles. That is, the viral yield from infection of ST6Gal I expressing CHO cells of the present invention was, in this experiment alone, 2.6-fold greater than that of wild type CHO cells. See also Table 2 and FIG. 7 which shows the increased viral titer yield over 96 hours post-infection between CHO cells engineered to express a 2,6-sialyltransferase gene and wild type CHO cells. After 24 hours post-infection, the "ST6 CHO" cells stably yielded more virus particles than wild type CHO over 48, 72, and 96 hours: 5.5 ($\log_{10}$ pfu/ml) for ST6 CHO compared to about 3.0 ($\log_{10}$ pfu/ml) for wild type CHO.

TABLE 1

Increased Virus Production in ST6Gal I expressing CHO Cells Infected with A/PR/8/34 Influenza Virus

| | Titer[3] (pfu/ml) | Ratio (ST6 CHO titer to WT CHO titer) |
|---|---|---|
| ST6 CHO[1] | $3.1 \times 10^3$ | 2.6 |
| WT CHO[2] | $1.2 \times 10^3$ | |

[1]ST6 CHO = ST6Gal I expressing CHO cells
[2]WT CHO = wildtype CHO cells
[3]Titers determined on MDCK cells by plaque assay

TABLE 2

The ratio of the mean fluorescence intensity between ST6Gal I-expressing CHO cells and wildtype CHO cells.

| Cells | Mean Fluorescent Intensity | Ratio of MFI (transfectant/parental) |
|---|---|---|
| CHO | 15.81 | — |
| CHO PB clone1 | 2033.94 | 128.65 |
| CHO clone 1 | 2225.77 | 140.78 |

The data and results presented in this Example were obtained and generated from the methods and materials disclosed in the following examples.

Example 2

Generate Stable CHO and Vero Cells Expressing Increased Numbers of Human Influenza Virus Specific Receptors This example concerns the stable transfection of the ST6Gal I gene, which encodes for 2,6-sialyltransferase I, into the CHO cell genome. This modification is expected to facilitate the production of vaccine virus in CHO cells.

Cell lines: CHO-S (Cat # 11619012, Invitrogen, San Diego, Calif.); Vero (ATCC CCL-81, Manassas, Va.); MDCK (ATCC CCL-34); Plasmids: ST6Gal I (ATCC, Manassas, Va.), pcDNA3.1 Onvitrogen, San Diego, Calif.); Viruses: A/Puerto Rico/8/34 (H1N1), A/Nanchang/933/95 (H3N2), A/Texas/36/91 (H1N1), B/Florida/4/06) (BEI, Manassas, Va.).

A. Construct Plasmids Expressing the ST6Gal I gene

Human (α2,6) ST6Gal I cDNA in the pSPORT vector (Invitrogen) is available from the ATCC (cat #10436251). The ST6Gal I gene was amplified by polymerase chain reaction (PCR) techniques with primers 5'-AAGCTTGCCGC-CACCATGATTCACACCAAC-3' (SEQ ID NO. 2) and 5'-CGGCGCCTCGAGTTAGCAGTGAATGGT-3' (SEQ ID NO. 3), containing HindIII and XhoI restriction sites, respectively. See Govorkova (supra), Lee (supra), and Fukuta (supra), for more information on CHO transfections and genetic modifications.

The resultant PCR product amplified by these primers, was digested with HindIII and XhoI, and then cloned into a HindIII- and XhoI-cut pcDNA3.1(+) (Invitrogen) expression vector, containing a CMV promoter. The resulting construct is denoted as pcDNA3.1ST6Gal I. *Escherichia coli*TOP10 competent cells (Invitrogen) were transformed by the ligated product and insert containing colonies were identified by PCR screening. The positive clones were analyzed by restriction digests and insert containing plasmids were purified using the Plasmid Midiprep kit (Promega). The sequences of the purified plasmids were confirmed by sequence analysis.

B. Establish Stable CHO and Vero Cells that Express ST6Gal I

The pcDNA3.1ST6Gal I plasmid constructed in A. and containing a neomycin resistant gene, was transfected into CHO and Vero cells by using the Trans IT-LT1 transfection reagent (Mirus) according to the manufacturer's instructions. Briefly, on the day before transfection, CHO and Vero cells were plated at $5 \times 10^5$ cells/100-mm dish. On day 1, 10 µg of plasmid DNA was mixed with 20 µg of Trans IT-LT1 in 0.3 ml of OptiMEM (Invitrogen) and was incubated with these cells at 37° C. in 5% $CO_2$ overnight. On day 2, the transfection mixture was replaced with a complete medium that is modified Eagle's medium (MEM) supplemented with 5% newborn calf serum. The medium also contained 400 µg/ml of geneticin (Invitrogen), a broad spectrum antibiotic that is used to select mammalian cells expressing the neomycin protein.

When resistant cells began to grow in the selection medium, the medium was replaced with fresh selection medium and geneticin-resistant clones were isolated by limited dilution in TC-96 plates. These ST6Gal I transfected CHO and Vero cells will hereafter be referred to as CHO-2,6 and Vero-2,6 cells.

C. Flow Cytometric Analysis of 2,6-Linked Sialic Acid Expression on Cells

Integration sites of plasmid DNA into the host cell chromosomes are random, therefore, the expression levels of STGal I protein in individual cell clones can vary significantly. The effect of ST6Gal I expression in CHO-2,6 cell clones and Vero-2,6 cell clones were studied by testing the cells' reactivity with sialic acid linkage-specific lectins. The reactivity was determined by fluorescence-activated cell sorter (FACS) analysis. Each of the ST6Gal I expressing clonal populations were expected to produce varying amounts of sialic acid on their surfaces. We therefore tested the clones with linkage-specific lectins to determine their relative level of reactivity with each lectin.

To examine the relative levels of sialic acid linked to galactose on the cell surface by α2,3 linkage (SA α2,3Gal) and α2,6 linkage (SAα2,6Gal), we used two digoxigenin-labeled lectins. These include *Sambucus nigra* which is agglutinin specific for SAα-2,6Gal and *Maackia amurensis* which is agglutinin specific for SAα2,3Gal (digoxigenin-glycan differentiation kit, Roche). An anti-digoxigenin fluorescein-conjugated antibody (Roche) was used as a secondary antibody. Fluorescence was determined by using a FACSCalibur flow cytometer (Becton Dickinson) to measure the fluorescence of a minimum of 10,000 cells.

Approximately $10^6$ parental or clonal cells were washed twice with PBS containing 10 mM glycine and then washed once with buffer 1 (50 mM Tris-HCl, 0.15 M NaCl, 1 mM $MgCl_2$, 1 mM $MnCl_2$, 1 mM $CaCl_2$, pH 7.5). The cells were subjected to a blocking solution, provided in the digoxigenin kit, for 1 h on ice. They were then washed in the same manner as described above. After centrifugation, the cell pellet was incubated with digoxigenin-labeled lectins (1 µl of either *S. nigra* agglutinin or *M. amurensis* agglutinin) in 30 µl of buffer 1 for 1 h on ice. After two washes with PBS containing glycine and one with buffer 1, the cells were incubated with 1 µl of anti-digoxigenin-fluorescein conjugated antibody in 30 µl of buffer 1 for 1 h on ice. After another three washes with PBS, the fluorescence intensities were quantified by FACS analysis.

Based on the relative intensities of 2,6-linked sialic acid expression, three stable clones of CHO-2,6 and Vero-2,6 cells (i.e., a total of 6 clones) were selected that over-express the human α2,6 ST6Gal I gene. The reactivity with *S. nigra* agglutinin (α2,6 specific) was increased 1.2 fold to 140 fold compared to that measured in the parent cells. The modified CHO and Vero clones (i.e., CHO-2,6 and Vero-2,6 cells) that express the highest levels of 2,6 sialic acids will be investigated further in Aim 2 for their ability to yield increased virus titers.

Example 3

Quantitate Seasonal and Pandemic Influenza Virus Yields Following Infection of CHO 2,6

This example will test whether higher expression levels of α2,6-linked sialic acid on the cell surface of the modified cells (CHO-2,6 and Vero-2,6 cells) generated in the preceding Example increases the cell's susceptibility to human influenza virus infection. The α2,6-linked sialic acid is the cell receptor used by the HA glycoprotein on the influenza virus that permits viral attachment to the host cell and leads to infection. The parental and modified CHO and Vero cell lines will be infected with seasonal and pandemic human influenza virus isolates and evaluated for their ability to yield high titers of virus. Populations of all 4 cell lines will be infected with representative influenza viruses (H1N1, H3N2, type B, and H5N1) and growth curves will be generated for each strain. The H1N1, H3N2, and type B influenza viruses represent the different subtypes included in the seasonal influenza vaccine. The H5N1 isolates represent potential pandemic virus and provide a fourth HA lineage to test herein. Testing influenza viruses displaying a range of HA subtypes will allow comparative assessment of how susceptible the modified cells may be to these 4 isolates as well as to predict the global infectivity influenza viruses displaying other HA subtypes in those modified cells.

A. Infection of Parental and Modified CHO and Vero Cells with Seasonal and Pandemic Influenza Viruses Five different cell lines will be infected with representative seasonal and pandemic influenza viruses. CHO-2,6 and Vero- 2,6 cells will be maintained in selection media as described above until time of infection and will be passaged twice weekly. CHO, Vero, and MDCK cells will also be infected as comparators. Influenza viruses (A/Puerto Rico/8/34 (H1N1), A/Nanchang/933/95 (H3N2), A/Texas/36/91 (H1N1), B/Florida/4/06) will be purchased from Biodefense and Emerging Infections Research Resources Repository (BEI, Manassas, Va.), working stocks of the virus will be made in MDCK cells, and stored in-80° C. Standard protocols for influenza infection will be followed.

Briefly, viral stocks will be diluted in serum free media and used to inoculate each of the five cell lines. The cells will have been washed three times with PBS prior to infection at a multiplicity of infection (MOI) of 0.001 to 1. Virus will be adsorbed at 37° C. for 1 hour, followed by removal of the inoculum and three PBS washes of the monolayers. After addition of virus growth medium (VGM) consisting of serum-free EMEM containing 1 µg/ml trypsin treated with L-1-tosylamido-2-phenylethyl chloromethyl ketone [(TPCK)—Worthington Biochemical], supernatant aliquots will be collected at 12 h, 24 h, 48 h, 72 h post infection to determine viral growth curves in each of the 5 cell lines. The supernatant containing virus will be harvested and cell debris removed by centrifugation. The virus fractions will be stored in aliquots at −80° C. and subsequently assayed by using MDCK cells. Growth curves for select H5N1 pandemic influenza viruses (representing current H5N1 clades) will be conducted.

B. Plaque Assays in MDCK Cells

MDCK monolayers will be cultured in 6-well tissue culture plates the day before the assay. On the day of the assay, the confluent monolayers will be washed three times with PBS and infected with serial dilutions of each virus sample generated above and incubated for 60 min at 37° C. to allow virus attachment to the cells. The inoculum will then be removed and the cells washed three times with PBS. An agarose overlay (1% agarose in MEM) containing 1 μg/ml trypsin/TPCK will be added and the infected cells incubated at 37° C. Forty eight to 72 hours later, the overlays will be removed, and the cell monolayers will be stained with 0.1% crystal violet in 20% methanol. Individual plaques will be counted and titers recorded as plaque forming units per ml of inoculum (pfu/ml). The viral titers obtained from each of the cell lines will be tabulated and the cell line generating the highest titers for the panel of viruses will be selected to be qualified.

Example 4

Clinical Isolates of Human Influenza Viruses Grow Better in ST6GAL I-Expressing Cells than in the Parental MDCK Cells To test whether a higher expression level of α2,6-linked sialic acid on the cell surface affects the susceptibility of that cell to infection with human influenza viruses, a plaque assay using clinical isolates of influenza viruses was conducted. Among 20 clinical specimens (eight H3N2, seven H1N1, and five type B viruses), titers were appreciably higher in the ST6Gal I-expressing cells compared with those in the MDCK cells. Briefly, serial virus dilutions in modified Eagle's medium (MEM) containing 7.5% bovine serum albumin (BSA) were incubated with cells for 60 minutes at 37° C. The inoculum was then removed and the cells were washed once with BSA-MEM. Agarose overlay (7.5% BSA, 0.5 μg/ml trypsin, 1% agarose in MEM) was added to each TC-6 well plate. The infected cells were placed at 37° C. in 5% $CO_2$. Two to three days later, the overlays were removed, and the cell monolayers were stained with 0.1% crystal violet in 20% methanol.

MDCK cells modified to express higher levels of ST6Gal I and infected with 20 influenza virus isolates yielded higher titers of virus compared to the parental cell line infected with the same isolate. In several instances, the modified cells produced viral titers that were on the order of a log higher than those produced by the MDCK cells. Sample 9, a 2002 isolate characterized as A/New Calcdonia/20/99-like produced 110 pfu/ml when used to infect MDCK cells and produced 26,000 pfu/ml when used to infect the ST6Gal I modified MDCK cells; a 100-fold increase.

In the second series of experiments, 23 viruses (eight H3N2, eight H1N1, and seven type B viruses) that had been isolated from clinical samples and propagated in MDCK cells were tested. All of these viruses grew to higher titers (20 times higher in some instances) in ST6Gal I-expressing cells than in MDCK cells. In this experiment, the methods used to infect cells, purify virus and titrate the virus yields were similar to those described earlier. These results indicate that the ST6Gal I-expressing cells are superior to MDCK cells in the isolation of human influenza viruses from clinical samples. ([a]Clinical nasal or pharyngeal swabs shown to be influenza virus-positive by a rapid diagnosis kit were used for virus titration; [b]plaque forming units per ml of inoculum as determined by plaque assay).

These preliminary studies described demonstrated the feasibility to stably transfect the MDCK mammalian cell line with a ST6Gal I expression vector that encodes for α2,6 sialyltransferase 1 to generate higher levels of human influenza virus receptors. The presence of increased α2,6 receptors augments the cells susceptibility to infection with viral isolates such that cells stably transfected with ST6GAL I produce up to 100-fold increases in virus titer over that possible in the parental MDCK cells.

Example 5

Replication of Influenza Viruses in ST6 CHO Cells

Influenza isolates representing past seasonal vaccine candidates [A/Nanching/933/95 (H3N2), A/Texas/36/91 (H1N1), and B/Florida/4/2006] or the lab strain PR8 [(A/Puerto Rico/8/34 (H1N1)] were obtained from BEI Resources (Manassas, Va.). Replication of these viruses in ST6 CHO cells were compared relative to replication in MDCK (Madin Darbin Canine Kidney) cells, the standard cell line used for culturing influenza virus. TC-24 plates were seeded with $2\times10^5$ cells/well of ST6 CHO or MDCK cells. The following day, confluent monolayers were washed twice with PBS and infected with each of the viruses at a multiplicity of infection (MOI) of 0.1. After 1 hour adsorption, the inoculum was removed and monolayer was washed with PBS. Virus growth medium (VGM, 1×EMEM, 2 mM L-glutamine with 0.3% BSA) containing 1 μg/ml trypsin/TPCK for MDCK or 0.5 μg/ml trypsin/TPCK for ST6 CHO was added.

Daily aliquots from the virus supernatants were taken starting at 24 hours post-infection up to 96 hours post-infection and stored at −80° C. Virus production in ST6 CHO and MDCK cells were studied by scoring for plaque formation in MDCK cells inoculated with the virus supernatants.

MDCK cells were grown until 95% confluence in TC-6 plates in EMEM with 2 mM L-glutamine and 10% fetal calf serum (Omega Scientific, Tarzana, Calif.). Ten-fold serial dilutions of virus supernatants were adsorbed onto monolayers washed twice with PBS to remove any traces of serum.

After 1 h at 37° C., the inoculum was removed and cells were washed twice with PBS and overlaid with 2 ml of agarose overlay (0.9% agarose, 1×EMEM with 1 µg/ml trypsin/TPCK (Worthington Biochemical)). The infected cells were then incubated in a humid 5% $CO_2$ incubator at 37° C. for 2-3 days. Viral plaques were visually scored and stained with crystal violet as described previously. Viral titers (pfu/ml) were determined for each cell type at each time point as shown in FIG. 9.

The growth curves for the different influenza viruses demonstrate that ST6 CHO cells support efficient influenza virus replication and grow to titers equivalent to or within a log to MDCK cells depending on the influenza subtype. See FIG. 9 (A-D). These results suggest that CHO cells that over-express the α-2,6 sialyltransferase would be extremely useful in the production of vaccines against influenza.

Example 6

Producing Mutagenized CHO Cells with ICR 191

Generally, CHO cells were mutagenized with ICR191 (an acridine half-mustard that causes frameshifts); and then infected with avian virus, which binds 2,3-sialic acid receptors. The majority of these cells were killed by the avian virus. Some cells, however, survived, and these were isolated and cultured. The sialic acid linkages on the surviving, mutagenized CHO cells were evaluated by flow cytometry. It was found that the 2,3-sialic acid linkages had decreased in survivor cells relative to the parent CHO cell; and that 2,6-sialic acid linkages had increased relative to the parent CHO cell.

More specifically, CHO-K1 cells (ATCC CCL-61) were cultured in F-12 medium containing 10% fetal calf serum (Omega Sciences, Tarzana, Calif.). CHO-K1 cells have been shown to display a mutant phenotype with disruption of only one copy of a gene. Fresh solutions (1 mg/ml) of ICR-191 prepared in 0.01 NHCl were stored at −20° C. prior to use. CHO-K1 cells (1×10⁶) were chemically mutagenized by ICR-191 treatment at final concentration of 10 µg/ml. Dilutions of ICR-191 were made in Hank's balanced salt solution (HBSS). ICR-191 was added at time=0 and incubated for an additional 16 hours. The alkylating agent ICR-191 induces frameshift and small deletions which have a low reversion rate relative to point mutations. The cells were then washed with PBS three times and seeded into fresh 10 cm culture dishes to establish a monolayer for infection. CHO-K1 cells are known to have 2,3 sialic acid receptors on the cell surface.

The monolayer was then infected by an avian influenza virus, A/mallard/New York/78, that preferentially recognizes 2,3 sialic acid receptors on the surface of cells. After three days of infection, extensive cytopathic effect was observed. However, isolated surviving cells were observed in the dish, presumably because they did not contain 2,3 receptors. The supernatant was removed and dishes washed with PBS. Fresh complete media (F-12 medium with 10% FBS) was added to the dishes to allow for the surviving cells to grow into colonies. These clones derived from single cells were then analyzed for cell surface sialic acid content by reactivity with linkage specific agglutinins determined by fluorescence-activated cell sorter (FACS) analysis. To examine the relative levels of sialic acid linked to galactose on the cell surface by α2,3 linkage (SA α2,3Gal) and α2,6 linkage (SAα2,6Gal), two digoxigenin-labeled lectins were used. These include *Sambucus nigra* which is agglutinin specific for SAα2,6Gal and *Maackia amurensis* which is agglutinin specific for SAα2,3Gal (digoxigenin-glycan differentiation kit, Roche). An anti-digoxigenin fluorescein-conjugated antibody (Roche) was used as a secondary antibody. Fluorescence was determined by using a FACSCalibur flow cytometer (Becton Dickinson) to measure the fluorescence of a minimum of 10,000 cells.

Approximately $10^6$ parental or clonal cells (clone numbers 7, 11, 12, 13, 23, 24, 28, 30, 33, 35, 37, 38) were washed twice with PBS containing 10 mM glycine and then washed once with buffer 1 (50 mM Tris-HCl, 0.15 M NaCl, 1 mM $MgCl_2$, 1 mM $MnCl_2$, 1 mM $CaCl_2$, pH 7.5). The cells were subjected to a blocking solution, provided in the digoxigenin kit, for 1 h on ice. They were then washed in the same manner as described above. After centrifugation, the cell pellet was incubated with digoxigenin-labeled lectins (1 μl of either *S. nigra* agglutinin or *M. amurensis* agglutinin) in 30 μl of buffer 1 for 1 h on ice. After two washes with PBS containing glycine and one with buffer 1, the cells were incubated with 1 μl of anti-digoxigenin-fluorescein conjugated antibody in 30 μl of buffer 1 for 1 h on ice. After another three washes with PBS, the fluorescence intensities were quantified by FACS analysis.

The relative intensities of 2,3-linked sialic acid expression and of 2,6-linked sialic acid expression were as expected for the wildtype CHO, as depicted in FIG. 10. However, the mutagenized clones no longer expressed any detectable 2,3-linked sialic acid, but did have an increase in levels of 2,6 sialic acids. The mutagenized cells that survived A/Mallard/New York/1978 infection did so because they no longer expressed 2,3 sialic acids.

Example 7

Replication of A/Puerto Rico/8/1934 Influenza Virus in Mutagenized CHO Clone 12BC Representative clone (Clone 12BC) from the mutagenized cells prepared in Example 6 was selected for further analysis to assess whether it can support influenza virus replication and to confirm that lack of 2,3 sialic acids was the reason they survived an avian virus infection.

Influenza isolate PR8 [A/Puerto Rico/8/34 (H1N1)] was obtained from BEI Resources (Manassas, Va.). The ability of mutagenized CHO clone 12BC to undergo influenza virus infection was tested relative to wild-type CHO-K1 cells (WT).

TC-24 plates were seeded with 2×$10^5$ cells/well of Clone 12BC or WT cells. The following day, confluent monolayers were washed twice with PBS and infected with each of the viruses at a multiplicity of infection (MOI) of 0.1. After 1 hour adsorption, the inoculum was removed and monolayer was washed with PBS. Virus growth medium (VGM, 1×EMEM, 2 mM L-glutamine with 0.3% BSA) containing 0.5 μg/ml trypsin/TPCK was added.

Daily aliquots from the virus supernatants were taken starting at 24 hours post-infection up to 72 hours post-infection and stored at −80° C. Virus production was determined by scoring for plaque formation in MDCK cells inoculated with the virus supernatants.

MDCK cells were grown until 95% confluence in TC-6 plates in EMEM with 2 mM L-glutamine and 10% fetal calf serum (Omega Scientific, Tarzana, Calif.). Ten-fold serial dilutions of virus supernatants were adsorbed onto monolayers washed twice with PBS to remove any traces of serum. After 1 h at 37° C., the inoculum was removed and cells were washed twice with PBS and overlaid with 2 ml of agarose overlay (0.9% agarose, 1×EMEM with 1 μg/ml trypsin/TPCK (Worthington Biochemical)). The infected cells were then incubated in a humid 5% $CO_2$ incubator at 37° C. for 2-3 days. Viral plaques were visually scored and stained with crystal violet as described previously. Viral titers (pfu/ml) were determined for each cell type at each time point as shown in FIG. 11.

The viral titers at each time point demonstrate that CHO cells mutagenized by ICR191, such as Clone 12BC, support efficient influenza virus replication. Clone 12BC does not have any detectable 2,3 sialic acid receptors on the cell surface, resulting in viral titers less than the WT for viruses such as PR8 that use both 2,3 and 2,6 sialic acid receptors. These results suggest that cells that express the α2,6 sialyltransferase exclusively, such as Clone 12BC, would be useful in the propagation of primary clinical influenza isolates to use as virus seed in the production of vaccines.

Example 8

Producing Influenza Vaccine in ST6 CHO Cells

Disposable bioreactor systems have been developed for mammalian cells whose benefits include faster facility setup and reduced risk of cross-contamination. ST6 CHO cells can be grown up in disposable bags such as those from Stedim, Bioeaze bags from SAFC Biosciences, HybridBag™ from Cellexus Biosytems or single use bioreactors from HyClone or Celltainer from Lonza. Bioreactors can be 1 L, 10 L, 50 L, 250 L, 1000 L size formats. The cells are maintained in suspension in optimized serum free medium, free of animal products. The system can be a fed-batch system where a culture can be expanded in a single bag from 1 L to 10 L for example, or a perfusion system that allows for the constant supply of nutrients while simultaneously avoiding the accumulation of potentially toxic by-products in the culture medium. The cells are grown to a certain density, from $2 \times 10^6$ to $6 \times 10^7$ cells per ml. The cells are infected with influenza vaccine seed strain at an MOI of 0.0001. The pH of the culture maintained between 6.8 to 7.4 to prevent conformational changes in influenza HA during infection. Trypsin/TPCK or a suitable protease is added at a concentration from 0.5 µg/ml to 2 µg/ml. The virus harvest (for each influenza subtype that is part of the trivalent vaccine) is collected from the bioreactor. The influenza virus in the cell culture medium can be separated from the cells after maximum yields are achieved (4 days to 5 days post-infection) by low-speed centrifugation or filtration and purified by either zonal gradient centrifugation or affinity chromatography or ion exchange chromatography. The cells will be treated with Benzonase to destroy host cell DNA. The virus will be inactivated with ethyl ether or sodium dodecyl sulfate or formaldehyde or β-propiolactone as the vaccine in final form can be whole inactivated or 'split' vaccine. It is estimated that yield from 1000 L bioreactor for MDCK cells would be comparable to 30800 eggs, i.e., 30800 doses (Vaccine 19:3444-3450). ST6 CHO cells are comparable in yield to MDCK cells for certain influenza subtypes. ST6 CHO cells are maintained as suspension cells, therefore there is no need for the addition or presence of any solid support material such as expensive microcarrier beads. In addition the challenge of attachment to microcarriers in the presence of trypsin/TPCK necessary for influenza virus multicycle replication is removed for suspension ST6 CHO resulting in better performance during scale-up for commercial purposes.

Example 9

Preparing H1N1SW Influenza Vaccine in ST6 CHO Cells

The presently disclosed inventive ST6 CHO vaccine production process gains greater importance in view of an increasing risk of an influenza pandemic-like situation. A suitable vaccine against a novel influenza virus must be manufactured in the largest possible quantities as quickly as possible. CHO cells overexpressing the human α2,6 sialyltransferase can be used to prepare a vaccine against the novel "swine" influenza virus that started circulating in humans in 2009. Manufacture involving eggs is not sufficiently flexible to allow vaccine supplies to be rapidly expanded when unexpected epidemics of novel strains occur as with the 2009 "swine flu." The seed virus for the H1N1 sw vaccine could be derived directly from clinical specimens, clinical isolates or from reassortants provided by the CDC, ideally without any interim egg passage to reflect the clinical isolate. ST6 CHO cell culture can be initiated in a shaker culture flask in a small volume followed by gradual scale up of the cells to targeted fermenter or bioreactor size. The seed virus can be introduced once the desired cell density is reached. A perfusion system may be introduced to maximize both cell growth and viral replication in the process. Perfusion allows for the constant supply of nutrients while simultaneously providing a means of avoiding the accumulation of potentially toxic by-products in the culture medium. The influenza virus in the cell culture medium can be separated from the cells after maximum yields are achieved (4 days to 5 days post-infection) by low-speed centrifugation or filtration and purified by either zonal gradient centrifugation or affinity chromatography or ion exchange chromatography. The cells will be treated with Benzonase to destroy host cell DNA. The virus will be inactivated with ethyl ether or sodium dodecyl sulfate or formaldehyde or β-propiolactone as the vaccine in final form can be whole inactivated or "split" vaccine. Following additional purification steps, the finished bulk would then be formulated, filled, and packaged to be administered either intramuscularly or intradermally.

Example 10

Human α2,6 Sialyltransferase Gene Expression of in CHO Cells

Expression of the human α2,6-sialyltransferase gene in stably transfected CHO cells was determined by RT-PCR. Oligonucleotides were designed specifically to detect human α2,6-sialyltransferase gene without identifying the endogenous hamster α2,6-sialyltransferase gene. Primers were synthesized to flank at least one intron in order to eliminate any cross-reactivity with endogenous genomic α2,6-sialyltransferase sequences.

Primer sequences were as follows:

```
Human α2,6-sialyltransferase specific primers:
ST6for
                                              (SEQ ID NO: 5)
5' TGG TAT CAG AAG CCA GAC TAC 3'

ST6rev
                                              (SEQ ID NO: 6)
5' CCC TCA TTG AGA TGC TTC ACC 3' cDNA PCR product: 355 bp

Murine β-actin specific primers:
β-actin for
                                              (SEQ ID NO: 7)
5' TCA TGA AGT GTG ACG TTG ACA TCC GT 3'

β-actin rev
                                              (SEQ ID NO: 8)
5' CTT AGA AGC ATT AGC GGT GCA CGA TG 3'
```

-continued
```
cDNA PCR product: 285 bp

DNA PCR product: 396 bp
```

RNA was extracted from 1×10⁶ parent CHO or ST6 CHO cells using SV Total RNA Isolation System kit (Promega). Total RNA was made into cDNA using ImProm-II Reverse Transcription System kit (Promega) using random oligonucleotides. The cDNA was used as template in PCR reactions using Promega's PCR Master Mix to amplify gene specific fragments with human ST6 specific primers or β-actin specific primers. Thermocycling conditions were as follows: 5 min, 95° C. one cycle; followed by 40 cycles of [20 sec, 94° C.; 30 sec, 55° C.; 1 min, 72° C.]; 7 min, 72° C. one cycle; 4° C. hold.

The PCR products were analyzed by agarose gel electrophoresis as shown in FIG. 12. The human ST6 specific primers detect a 355 base pair PCR product, as predicted, that is not present in the parent CHO cells. Expression of the housekeeping gene control, β-actin, is detected in both the ST6 CHO and CHO cells as shown by the presence of the 285 base pair product. A conclusion therefore is that the increase in α2,6-receptors on the surface of ST6 CHO cells is due to expression of the transfected human α2,6-sialyltransferase gene and not the expression of the endogenous hamster α2,6-sialyltransferase gene.

There is no cross-reactivity between the hamster α2,6-sialyltransferase sequence and the human sequence as demonstrated by the absence of any PCR products when RNA is used as the template without being reverse transcribed into cDNA (no reverse transcriptase controls in figure). The "no reverse transcriptase controls" with the β-actin primers do detect a fragment of 396 base pairs suggesting that there is low level genomic DNA in the RNA. The size of this fragment is larger than the cDNA fragment due to the intron in the genome.

SEQUENCES

```
SEQ ID NO. 1: Nucleotide Sequence of ST6 cDNA
CGANCNCGTTACTTAGCTTGCCGCCCCATGATTCACACCAACCTGAAGAAAAAGTTCAGCTG

CTGCGTCCTGGTCTTTCTTCTGTTTGCAGTCATCTGTGTGTGGAAGGAAAAGAAGAAAGGGA

GTTACTATGATTCCTTTAAATTGCAAACCAAGGAATTCCAGGTGTTAAAGAGTCTGGGGAAA

TTGGCCATGGGGTCTGATTCCCAGTCTGTATCCTCAAGCAGCACCCAGGACCCCCACAGGGG

CCGCCAGACCCTCGGCAGTCTCAGAGGCCTAGCCAAGGCCAAACCAGAGGCCTCCTTCCAGG

TGTGGAACAAGGACAGCTCTTCCAAAAACCTTATCCCTAGGCTGCAAAAGATCTGGAAGAAT

TACCTAAGCATGAACAAGTACAAAGTGTCCTACAAGGGGCCAGGACCAGGCATCAAGTTCAG

TGCAGAGGCCCTGCGCTGCCACCTCCGGGACCATGTGAATGTATCCATGGTAGAGGTCACAG

ATTTTCCCTTCAATACCTCTGAATGGGAGGGTTATCTGCCCAAGGAGAGCATTAGGACCAAG

GCTGGGCCTTGGGGCAGGTGTGCTGTTGTGTCGTCAGCGGGATCTCTGAAGTCCTCCCAACT

AGGCAGAGAAATCGATGATCATGACGCAGTCCTGAGGTTTAATGGGGCACCCACAGCCAACT

TCCAACAAGATGTGGGCACAAAAACTACCATTCGCCTGATGAACTCTCAGTTGGTTACCACA

GAGAAGCGCTTCCTCAAAGACAGTTTGTACAATGAAGGAATCCTAATTGTATGGGACCCATC

TGTATACCACTCAGATATCCCAAAGTGGTACCAGAATCCGGATTATAATTTCTTTAACAACT

ACAAGACTTATCGTAAGCTGCACCCCAATCAGCCCTTTTACATCCTCAAGCCCCAGATGCCT

TGGGAGCTATGGGACATTCTTCAAGAAATCTCCCCAGAAGAGATTCAGCCAAACCCCCCATC

CTCTGGGATGCTTGGTATCATCATCATGATGACGCTGTGTGACCAGGTGGATATTTATGAGT

TCCTCCCATCCAAGCGCAAGACTGACGTGTGCTACTACTACCAGAAGTTCTTCGATAGTGCC

TGCACGATGGGTGCCTACCACCCGCTGCTCTATGAGAAGAATTTGGTGAAGCATCTCAACCA

GGGCACAGATGAGGACATCTACCTGCTTGGAAAAGCCACACTGCCTGGCTTCCGGACCATTC

ACTGCTAACTCGAGTCAGAGGCCGTAACNGCN

SEQ ID NO. 2: Primer
5'-AAGCTTGCCGCCACCATGATTCACACCAAC-3'

SEQ ID NO. 3: Primer
5'-CGGCGCCTCGAGTTAGCAGTGAATGGT-3'

SEQ ID NOS 4 and 9, respectively:
Amino Acid Sequence of Translated ST6 cDNA
R X R Y L A C R P Met I H T N L K K K F S C C V L V F L L F A

V I C V W K E K K K G S Y Y D S F K L Q T K E F Q V L K S L G

K L A M G S D S Q S V S S S S T Q D P H R G R Q T L G S L R G
```

-continued

```
L A K A K P E A S F Q V W N K D S S S K N L I P R L Q K I W K

N Y L S M N K Y K V S Y K G P G P G I K F S A E A L R C H L R

D H V N V S M V E V T D F P F N T S E W E G Y L P K E S I R T

K A G P W G R C A V V S S A G S L K S S Q L G R E I D D H D A

V L R F N G A P T A N F Q Q D V G T K T T I R L M N S Q L V T

T E K R F L K D S L Y N E G I L I V W D P S V Y H S D I P K W

Y Q N P D Y N F F N N Y K T Y R K L H P N Q P F Y I L K P Q M

P W E L W D I L Q E I S P E E I Q P N P P S S G M L G I I I M

M T L C D Q V D I Y E F L P S K R K T D V C Y Y Y Q K F F D S

A C T M G A Y H P L L Y E K N L V K H L N Q G T D E D I Y L L

G K A T L P S F R T I H C Stop L E S E A V X X
```

---

What is claimed is:

1. A cell culture-based method for producing influenza virus vaccine, comprising (A) infecting a Chinese Hamster Ovary cell (CHO) with a human influenza virus that binds to cell surface 2,6-linked sialic acids, and (B) isolating human influenza viruses produced from the CHO cell, and (C) formulating the isolated human influenza viruses into an influenza virus vaccine, wherein the CHO cell expresses a ST6GAL1 gene and comprises cell-surface bound 2,6-linked sialic acids, and wherein the susceptibility of the CHO cell to human influenza virus infection is greater than a CHO cell that does not express the ST6GAL 1 gene.

2. The cell culture-based method of claim 1, further comprising incubating the CHO cells with lectins against 2,3-sialic acid receptors.

3. The cell culture-based method of claim 1, wherein the generation time for producing the influenza vaccine is about 12 weeks from the time of viral infection of the CHO cells.

4. The cell culture-based method of claim 1, wherein 10 to 6,000 liters of CHO cells are infected with the human influenza virus.

5. The cell culture-based method of claim 1, wherein the human influenza virus is selected from the group consisting of H1N1, H2N2 and H3N2 influenza subtypes.

6. A cell culture-based method for producing influenza virus for making a human influenza vaccine, comprising infecting a CHO cell that expresses ST6GAL 1 with a human influenza virus that binds to cell surface 2,6-linked sialic acids, wherein the susceptibility of the CHO cell to human influenza virus infection is greater than a CHO cell that does not express the ST6GAL 1 gene, and wherein the CHO cell produces infectious human influenza viruses.

7. The cell culture-based method of claim 6, wherein the human influenza virus is selected from the group consisting of H1N1, H2N2 and H3N2 influenza subtypes.

8. The cell culture-based method of claim 6, further comprising incubating the CHO cells with lectins against 2,3-sialic acid receptors.

9. The cell culture-based method of claim 6, wherein the generation time for producing the influenza vaccine is about 12 weeks from the time of viral infection of the CHO cells.

10. The cell culture-based method of claim 6, wherein 10 to 6,000 liters of CHO cells are infected with the human influenza virus.

11. The cell culture-based method of claim 6, wherein the CHO cell has an increased cell surface expression of 2,6-linked sialic acids, compared to a wild-type CHO cell.

12. The cell culture-based method of claim 6, wherein the ST6GAL 1 gene is a human ST6GAL 1 gene.

13. The cell culture-based method of claim 6, wherein the CHO cell yields a pfu/ml titer of human influenza virus that is at least 2 times higher than the pfu/ml titer yield of a CHO cell which does not express the ST6GAL 1 gene.

14. The cell culture-based method of claim 6, further comprising isolating human influenza viruses produced from the CHO cell.

15. The cell culture-based method of claim 14, further comprising formulating the isolated human influenza viruses into a vaccine.

16. A cell culture-based method for producing influenza virus for making a human influenza vaccine, comprising (A)

infecting a Chinese Hamster Ovary cell (CHO) with a human influenza virus that binds to cell surface 2,6-linked sialic acids, wherein the CHO cell (i) expresses a 2,6-sialyltransferase gene (ST6GAL 1), and (ii) has an increased cell surface expression of 2,6-linked sialic acids, compared to a wild-type CHO cell; and (B) isolating human influenza viruses produced from the CHO cell, wherein the CHO cell yields a pfu/ml titer of human influenza virus that is at least 2 times higher than the pfu/ml titer yield of a CHO cell which does not express the ST6GAL 1 gene.

* * * * *